US010500198B2

(12) United States Patent
Roden et al.

(10) Patent No.: US 10,500,198 B2
(45) Date of Patent: *Dec. 10, 2019

(54) BIS-BENZYLIDINE PIPERIDONE PROTEASOME INHIBITOR WITH ANTICANCER ACTIVITY

(71) Applicant: The Johns Hopkins University, Baltimore, MD (US)

(72) Inventors: Richard B. Roden, Severna Park, MD (US); Ravi K. Anchoori, Elkridge, MD (US); Balasubramanyam Karanam, Auburn, AL (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/876,880

(22) Filed: Jan. 22, 2018

(65) Prior Publication Data

US 2019/0175572 A1  Jun. 13, 2019

Related U.S. Application Data

(62) Division of application No. 14/889,768, filed as application No. PCT/US2014/037031 on May 6, 2014, now Pat. No. 9,913,834.

(60) Provisional application No. 61/820,884, filed on May 8, 2013, provisional application No. 61/838,156, filed on Jun. 21, 2013.

(51) Int. Cl.
| | |
|---|---|
| *A61K 31/45* | (2006.01) |
| *C07D 401/06* | (2006.01) |
| *C07D 401/12* | (2006.01) |
| *C07D 451/06* | (2006.01) |
| *C07D 471/08* | (2006.01) |
| *C07D 487/04* | (2006.01) |
| *C07D 495/04* | (2006.01) |
| *C07D 213/68* | (2006.01) |
| *A61K 9/00* | (2006.01) |
| *A61K 31/439* | (2006.01) |
| *A61K 31/454* | (2006.01) |
| *A61K 31/4545* | (2006.01) |
| *A61K 31/497* | (2006.01) |
| *A61K 31/519* | (2006.01) |
| *A61K 38/05* | (2006.01) |
| *C07D 211/74* | (2006.01) |
| *C07D 475/04* | (2006.01) |

(52) U.S. Cl.
CPC ............ *A61K 31/45* (2013.01); *A61K 9/0014* (2013.01); *A61K 9/0053* (2013.01); *A61K 31/439* (2013.01); *A61K 31/454* (2013.01); *A61K 31/4545* (2013.01); *A61K 31/497* (2013.01); *A61K 31/519* (2013.01); *A61K 38/05* (2013.01); *C07D 211/74* (2013.01); *C07D 213/68* (2013.01); *C07D 401/06* (2013.01); *C07D 401/12* (2013.01); *C07D 451/06* (2013.01); *C07D 471/08* (2013.01); *C07D 475/04* (2013.01); *C07D 487/04* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 9,359,196 B2 | 6/2016 | Awasthi et al. | |
| 9,913,834 B2 * | 3/2018 | Roden ................ | A61K 31/497 |
| 2008/0234320 A1 | 9/2008 | Snyder et al. | |
| 2013/0079370 A1 | 3/2013 | Brnjic et al. | |
| 2016/0106725 A1 | 4/2016 | Roden et al. | |

FOREIGN PATENT DOCUMENTS

CN          101691353 A      4/2010

OTHER PUBLICATIONS

Adams, "The proteasome: a suitable antineoplastic target," Nat Rev Cancer 4, 349-360 (2004).
Al-Shami et al., "Regulators of the proteasome pathway, Uch37 and Rpn13, play distinct roles in mouse development," PLoS ONE 5, e13654 (2010).
Anchoori et al., "A bis-benzylidine piperidone targeting proteasome ubiquitin receptor RPN13/ADRM1 as a therapy for cancer," Cancer Cell, vol. 24, pp. 791-805 (2013).
Anchoori et al., "Stressing the ubiquitin-proteasome system without 20S proteolytic inhibition selectively kills cervical cancer cells," PLoS ONE 6, e23888 (2011).
Arastu-Kapur et al., "Nonproteasomal targets of the proteasome inhibitors bortezomib and cartilzomib: a link to clinical adverse events," Clin. Cancer Res. 17, 2734-2743 (2011).

(Continued)

*Primary Examiner* — Zinna Northington Davis
(74) *Attorney, Agent, or Firm* — Keith G. Haddaway; Miguel A. Lopez; Venable LLP

(57) ABSTRACT

We describe a bis-benzylidine piperidone, RA190, which covalently binds to the ubiquitin receptor RPN13 (ADRM1) in the 19S regulatory particle and inhibits proteasome function, triggering rapid accumulation of polyubiquitinated proteins. Multiple myeloma lines, even those resistant to bortezomib, were sensitive to RA190 via ER stress-related apoptosis. RA190 stabilized targets of human papillomavirus (HPV) E6 oncoprotein, and preferentially killed HPV-transformed cells. After p.o. or i.p. dosing of mice, RA190 distributed to plasma and major organs excepting brain, and potently inhibited proteasome function in skin and muscle. RA190 administration i.p. profoundly reduced growth of multiple myeloma and ovarian cancer xenografts, and oral RA190 treatment retarded HPV+ syngeneic mouse tumor growth, without impacting spontaneous HPV-specific CD8+ T cell responses, suggesting its therapeutic potential. The bis-benzylidine piperidone RA190 is a new orally-available proteasome inhibitor. Multiple myeloma, cervical and ovarian cancers are particularly sensitive to RA190.

17 Claims, 39 Drawing Sheets

(56) References Cited

OTHER PUBLICATIONS

Awasthi et al., "Antiproliferative compositions comprising curcumin analogs and methods of producing and using same," CA157:726232 (2012).
Bazzaro et al., "a,b-Unsaturated carbonyl system of chalcone-based derivatives is responsible for broad inhibition of proteasomal activity and preferential killing of human papilloma virus (HPV) positive cervical cancer cells," J. Med. Chem. 54, 449-456 (2011).
Bazzaro et al., "Ubiquitin-proteasome system stress sensitizes ovarian cancer to proteasome inhibitor-induced apoptosis," Cancer Res 66, 3754-3763 (2006).
Bedford et al., "Ubiquitin-like protein conjugation and the ubiquitin-proteasome system as drug targets," Nat Rev Drug Discov 10, 29-46 (2011).
Best et al., "Administration of HPV DNA vaccine via electroporation elicits the strongest CD8+ T cell immune responses compared to intramuscular injection and intradermal gene gun delivery," Vaccine 27, 5450-5459 (2009).
Bundgaard, "Design of prodrugs," pp. 27-32 (1985).
Chauhan et al., "A novel orally active proteasome inhibitor induces apoptosis in multiple myeloma cells with mechanisms distinct from Bortezomib," Cancer Cell 8, 407-419 (2005).
Chen, et al., "Genome-wide siRNA screen for modulators of cell death induced by proteasome inhibitor bortezomib," Cancer Res 70, 4318-4326 (2010).
Chen et al., "Structure of proteasome ubiquitin receptor hRpn13 and its activation by the scaffolding protein hRpn2," Mol Cell 38, 404-415 (2010).
Ciechanover, "The ubiquitin-proteasome pathway: on protein death and cell life," Embo. J., 17, 7151-7160 (1998).
Delaglio et al., "NMRPipe: a multidimensional spectral processing system based on UNIX pipes," J Biomol NMR, 6, 277-293 (1995).
Deveraux et al., "A 26 S protease subunit that binds ubiquitin conjugates," J. Biol. Chem., 269, 7059-7061 (1994).
Dominguez et al., "HADDOCK: a protein-protein docking approach based on biochemical or biophysical information," J Am Chem Soc,125, 1731-1737 (2003).
Dorwald, "Side Reactions in Organic Synthesis: A Guide to Successful Synthesis Design," p. ix (2005).
Extended European Search Report in European Patent Application No. 14795355.8, dated Sep. 21, 2016.
Gandhi et al., "Analysis of the human protein interactome and comparison with yeast,; worm and fly interaction datasets," Nat. Genet. 38, 285-293 (2006).
Hamazaki et al., "A novel proteasome interacting protein recruits the deubiquitinating enzyme UCH37 to 26S proteasomes," Embo J, 25, 4524-4536 (2006).
Howie et al., "Papillomavirus E6 proteins," Virology, 384, 324-334 (2009).
Husnjak et al., "Proteasome subunit Rpn13 is a novel ubiquitin receptor," Nature, 453, pp. 481-488 (2008).
International Preliminary Report on Patentability in PCT International Application No. PCT/US2014/037031 dated Nov. 10, 2015.
Ito et al., "A comprehensive two-hybrid analysis to explore the yeast protein interactome," Proc. Natl. Acad. Sci. USA 98, pp. 4569-4574 (2001).
Kia et al., "(3E, 5E)-3, 5-Dibenzylidene-1-[3-(piperidin-1-yl)propanoyl]piperidin-4-one," Acta Crystallographica Section E: Structure Reports Online, vol. 67, pp. o1299-o1300 (2011).
Koulich et al., "Relative structural and functional roles of multiple deubiquitylating proteins associated with mammalian 26S proteasome," Mol. Biol. Cell, 19, pp. 1072-1082 (2008).

Kuhn et al. "Targeting the insulin-like growth factor-1 receptor to overcome bortezomib resistance in preclinical models of multiple myeloma," Blood 120, 3260-3270 (2012).
Lagisetty et al., "CLEFMA—An anti-proliferative curcuminoid from structure-activity relationship studies on 3,5-bis (benzylidene)-4-piperidones," Bioorganic & Medicinal Chemistry, vol. 18, No. 16, Aug. 1, 2010 (Aug. 1, 2010), pp. 6109-6120.
Lin et al., "Combination of Proteasome and HDAC Inhibitors for Uterine Cervical Cancer Treatment," Clin Cancer Res 15, pp. 570-577 (2009).
Luker et al., "Imaging 26S proteasome activity and inhibition in living mice," Nat Med, 9, pp. 969-973 (2003).
Maki et al., "In vivo ubiquitination and proteasome-mediated degradation of p53(1)," Cancer Res 56, 2649-2654 (1996).
Moody et al., "Human papillomavirus oncoproteins: pathways to transformation," Nat Rev Cancer 10, pp. 550-560 (2010).
Pati et al., "Cytotoxic 3,5-bis(benzylidene)piperidin-4-ones and N-acyl analogs displaying selective toxicity for malignant cells," European Journal of Medicinal Chemistry, Editions Scientifique Elsevier, Paris, FR, vol. 43, No. 1, Jan. 1, 2008 (Jan. 1, 2008), pp. 1-7.
PubChem, CID 11134095 (Oct. 26, 2006).
Qiu et al., "hRpn13/ADRM1/GP110 is a novel proteasome subunit that binds the deubiquitinating enzyme, UCH37," EMBO J. 25, pp. 5742-5753 (2006).
Ri et al., "Bortezomib-resistant myeloma cell lines: a role for mutated PSMB5 in preventing the accumulation of unfolded proteins and fatal ER stress," Leukemia, 24, 1506-1512 (2010).
Ruschak et al., "Novel proteasome inhibitors to overcome bortezomib resistance," J Natl Cancer Inst, 103, pp. 1007-1017 (2011).
Sakata et al., "Localization of the proteasomal ubiquitin receptors Rpn10 and Rpn13 by electron cryomicroscopy," Proc Natl Acad Sci U S A, 109, 1479-1484 (2012).
Schreiner et al., "Ubiquitin docking at the proteasome through a novel pleckstrin-homology domain interaction," Nature 453, 548-552 (2008).
Schwartz et al., "Targeting proteins for destruction by the ubiquitin system: implications for human pathobiology," Annu Rev Pharmacol Toxicol, 49, pp. 73-96 (2009).
Silverman, "The Organic Chemistry of Drug Design and Drug Action," pp. 65-72 (1993).
Song et al., "Amino Acid Ester Prodrugs of the Anticancer Agent Gemcitabine: Synthesis, Bioconversion, Metabolic, Bioevasion, and hPEPT1-Mediated Transport," Molecular Pharmaceutics, 2(2): pp. 157-167 (2004).
Spisek et al., "Towards a better way to die with chemotherapy: role of heat shock protein exposure on dying tumor cells," Cell Cycle 6, 1962-1965 (2007).
Trimble et al., "Comparison of the CD8+ T cell responses and antitumor effects generated by DNA vaccine administered through gene gun, biojector, and syringe," Vaccine, 21, 4036-4042 (2003).
Vousden et al., "Live or let die: the cell's response to p53," Nat Rev Cancer 2, 594-604 (2002).
Welters et al., "Induction of tumor-specific CD4+ and CD8+ T-cell immunity in cervical cancer patients by a human papillomavirus type 16 E6 and E7 long peptides vaccine," Clin Cancer Res 14, 178-187 (2008).
Xu et al., "N-Boc-3, 5-(E)-diarylmethylene-4-piperidone and its application as antitumor agents," CA152:476964 (2010).
Yao et al., "Proteosome Recruitment and activation of the Uch37 debiquitinating enzyme by Adrm1," Nat. Cell Biol., 8, pp. 994-1002 (2006).

* cited by examiner

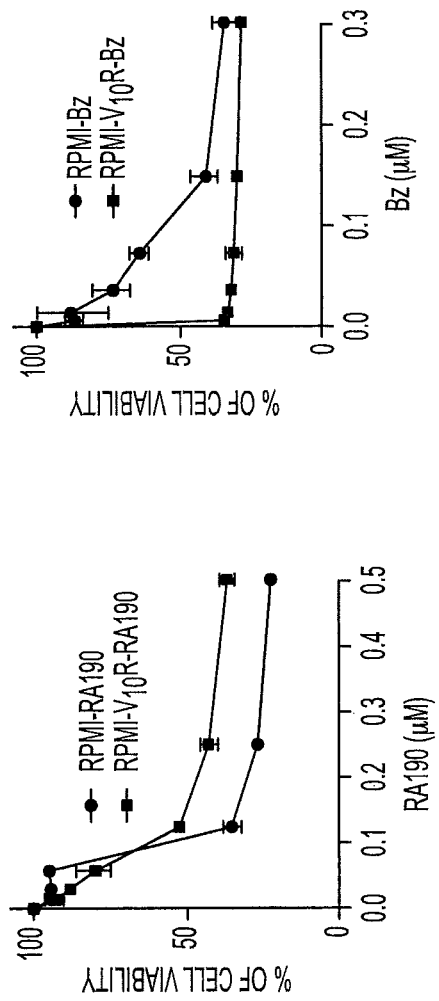
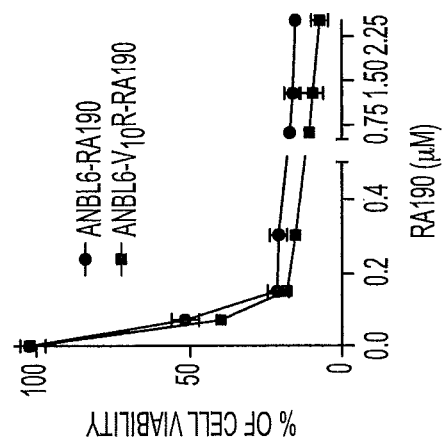
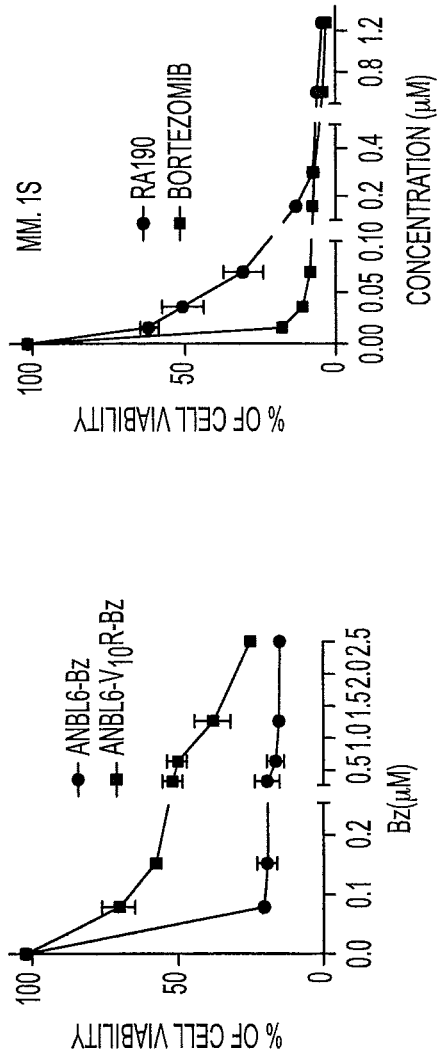
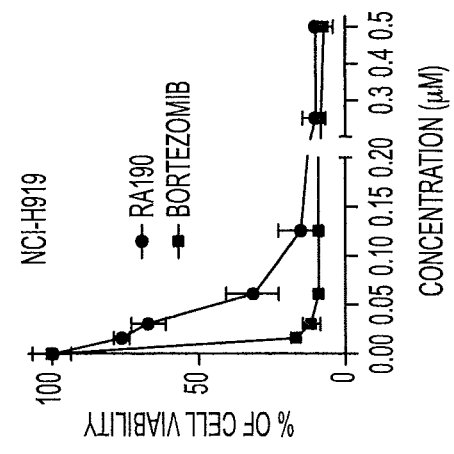
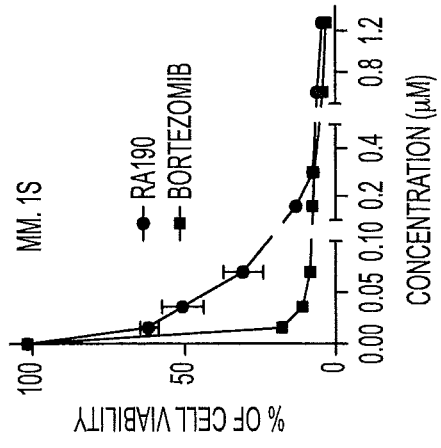

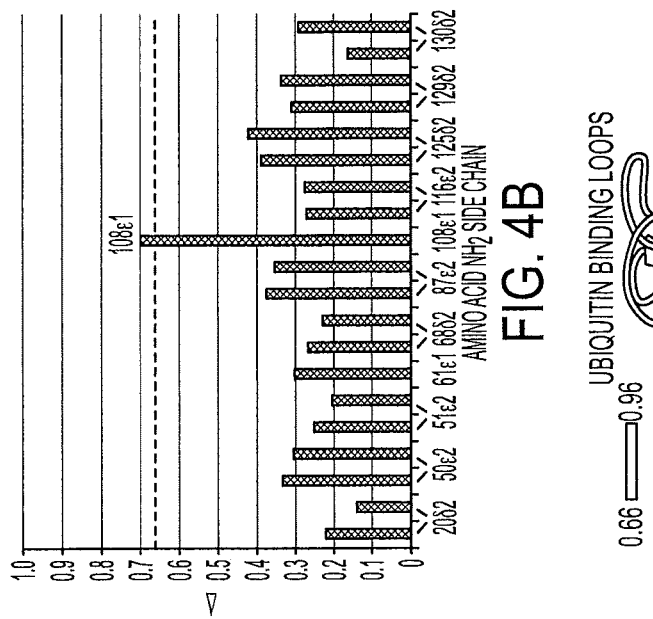
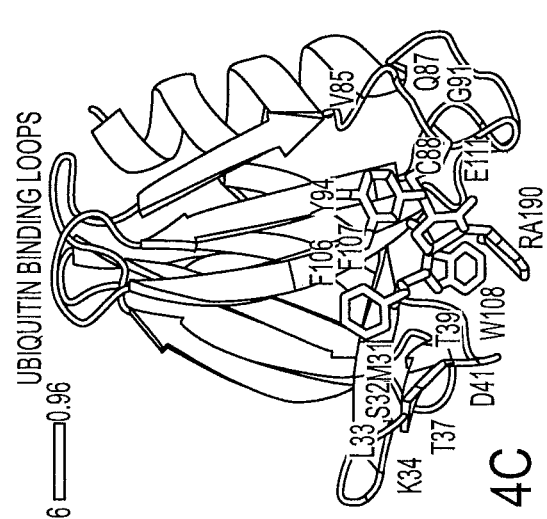
FIG. 4B
FIG. 4C
FIG. 4A

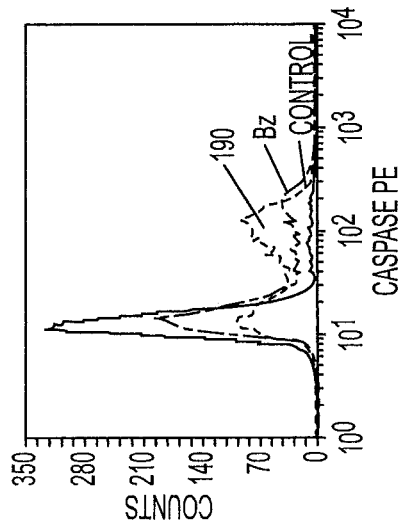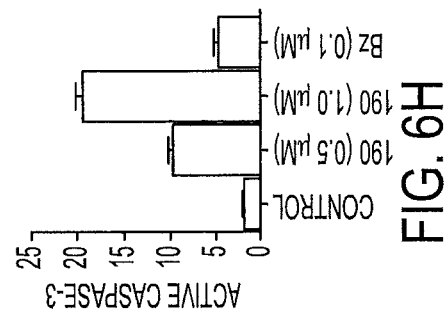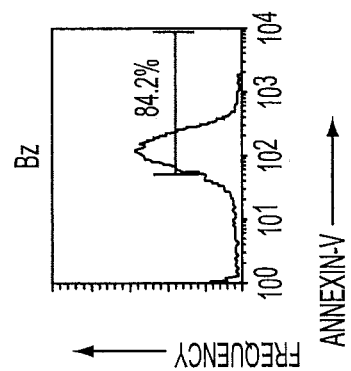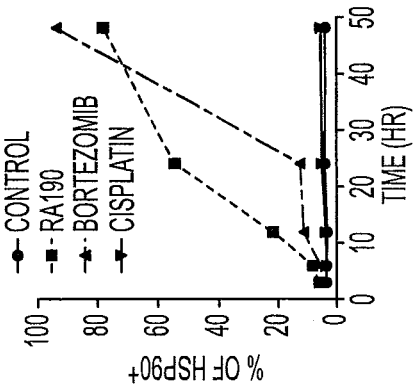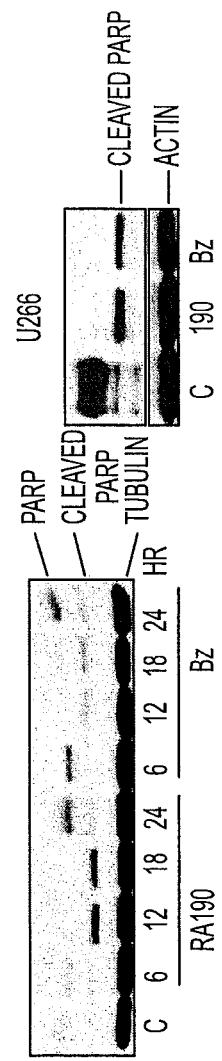

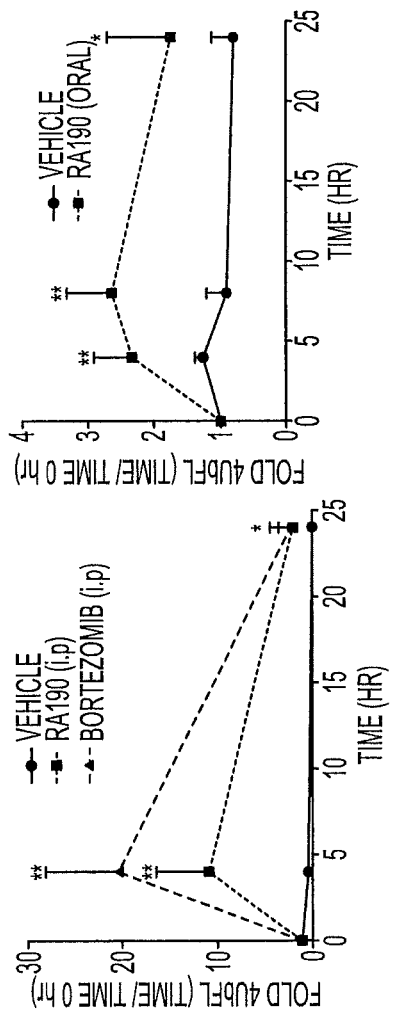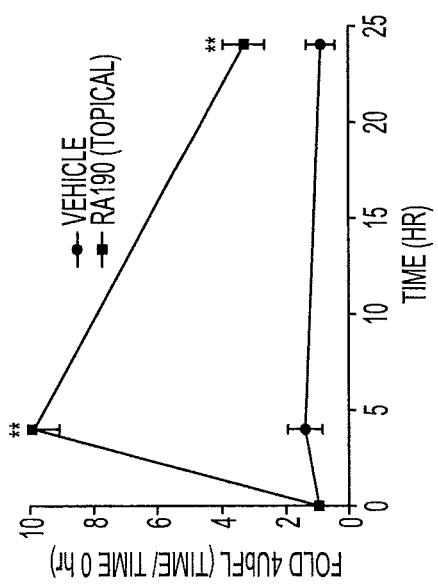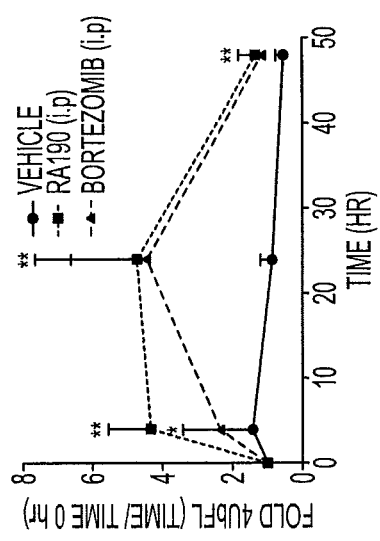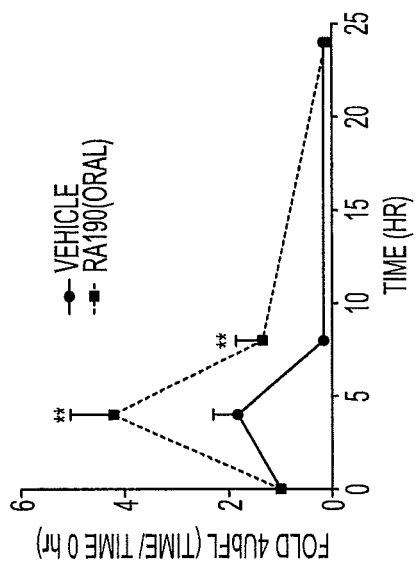
FIG. 7A  FIG. 7B  FIG. 7C  FIG. 7D  FIG. 7E

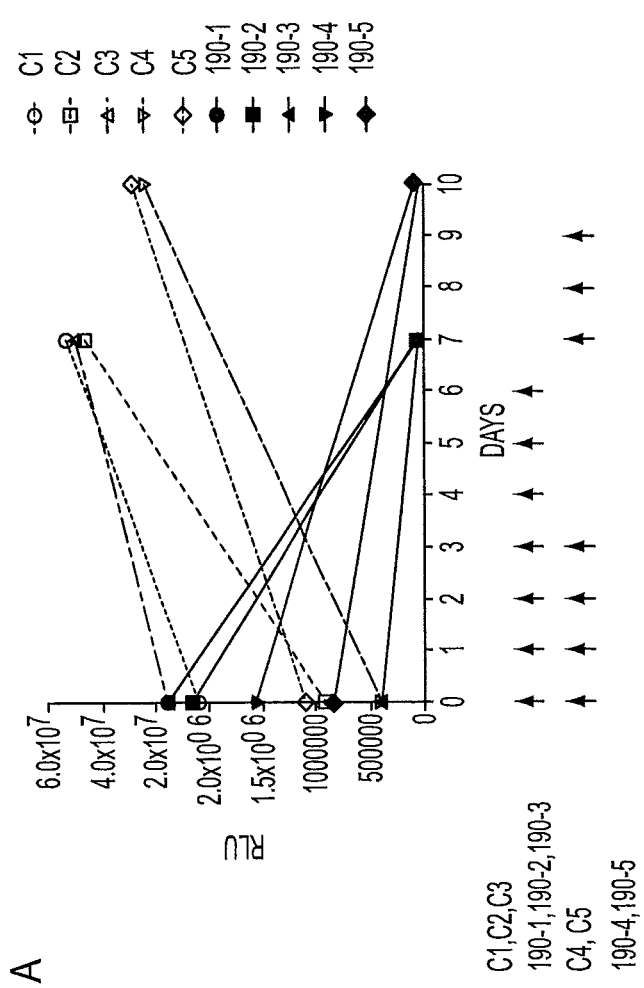
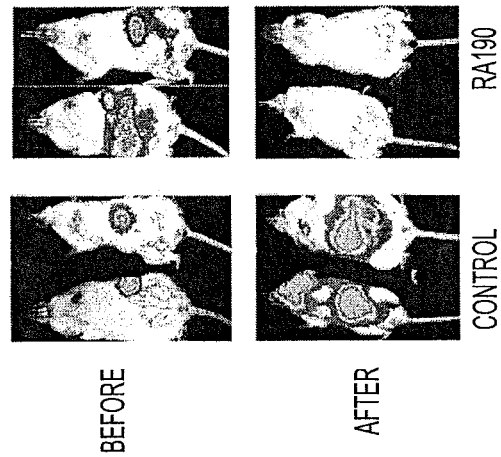
FIG. 8A
FIG. 8B

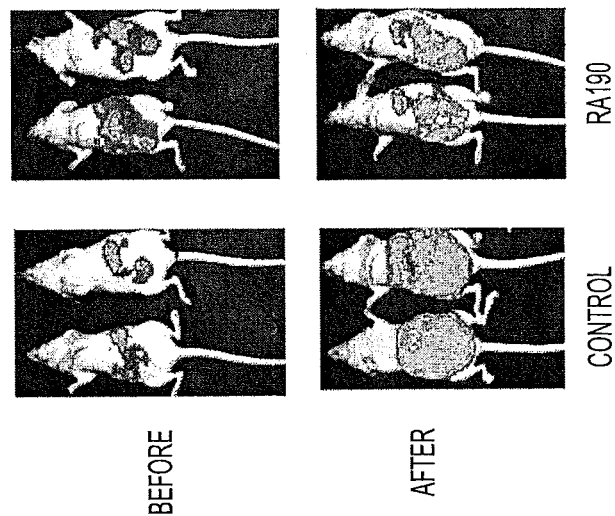
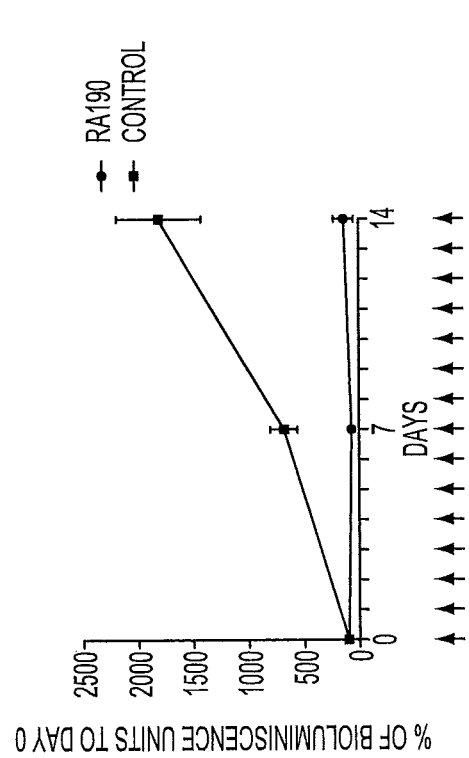
FIG. 8D
FIG. 8C

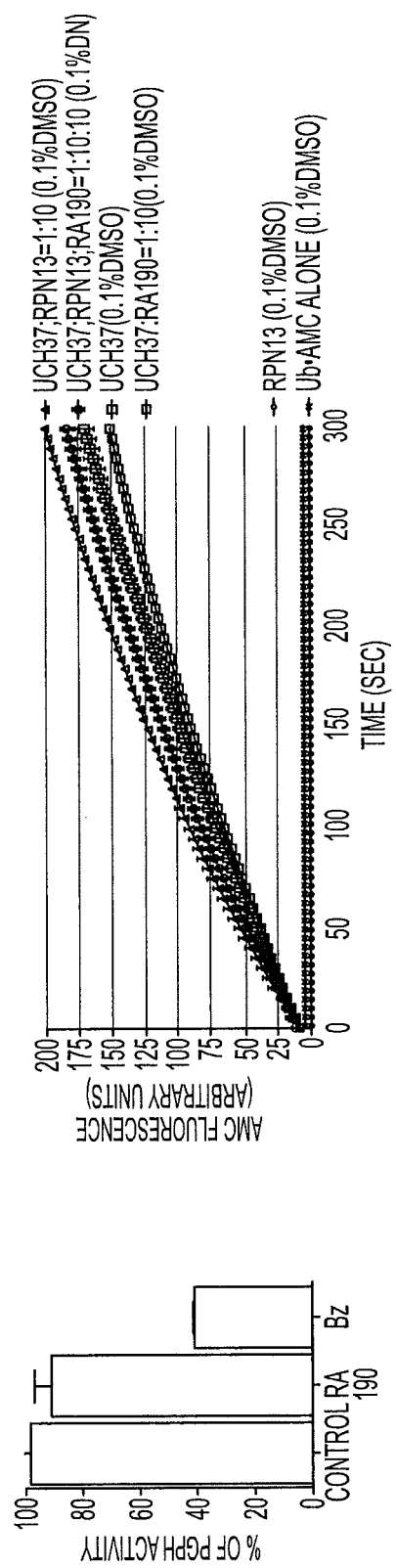
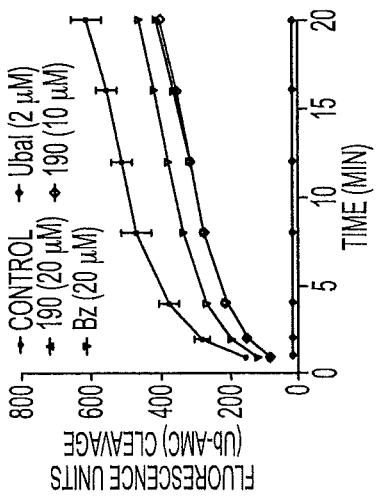
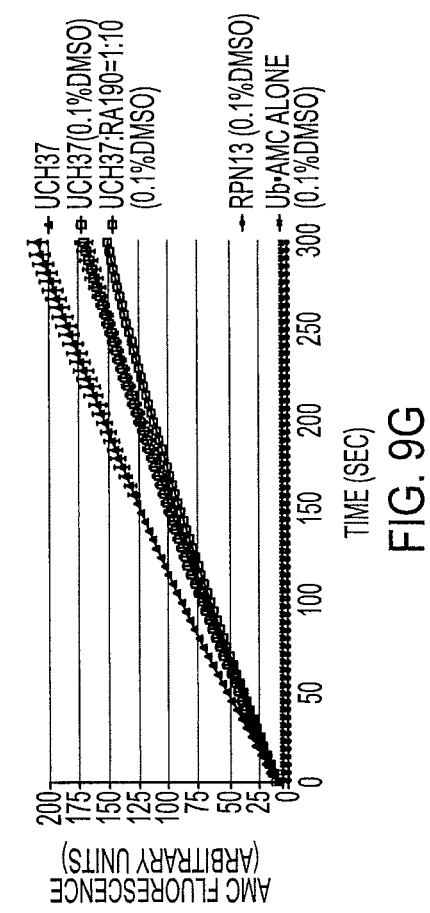
FIG. 9E
FIG. 9F
FIG. 9G
FIG. 9H

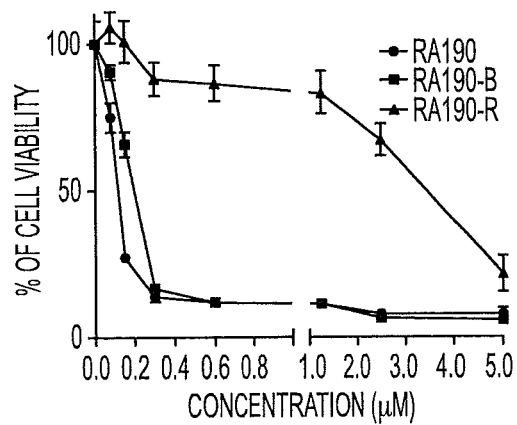
FIG. 10A
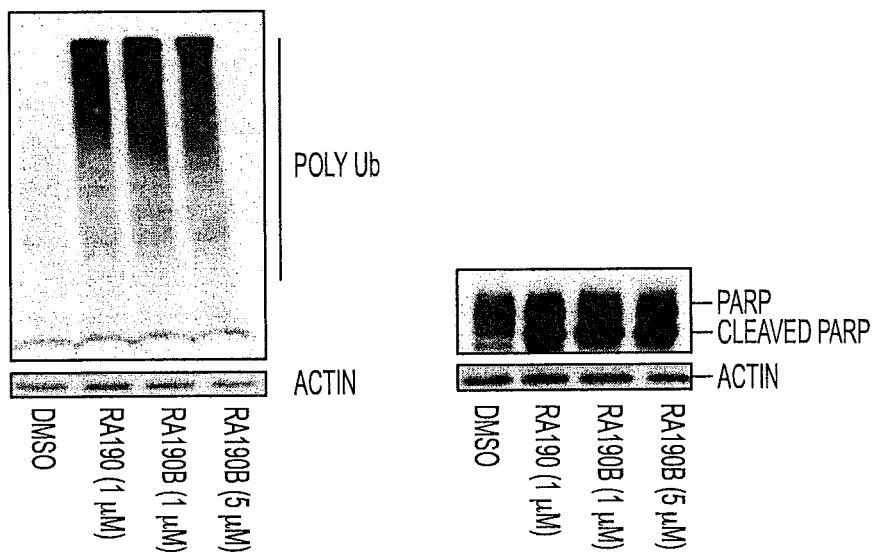
FIG. 10B
FIG. 10C

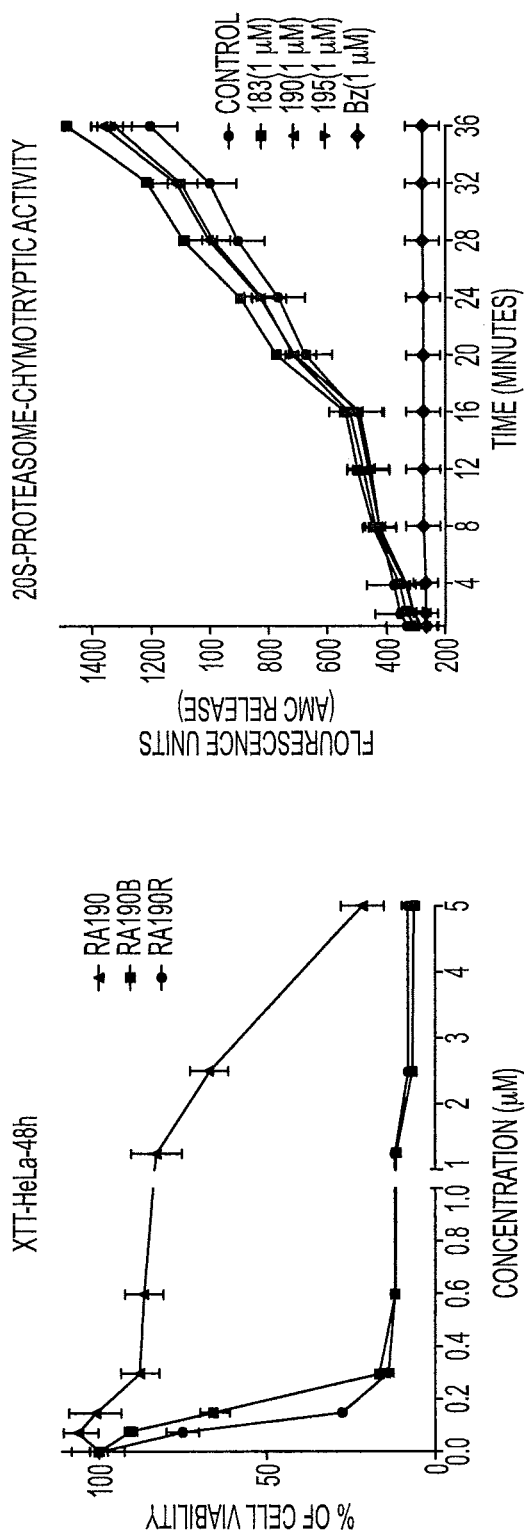
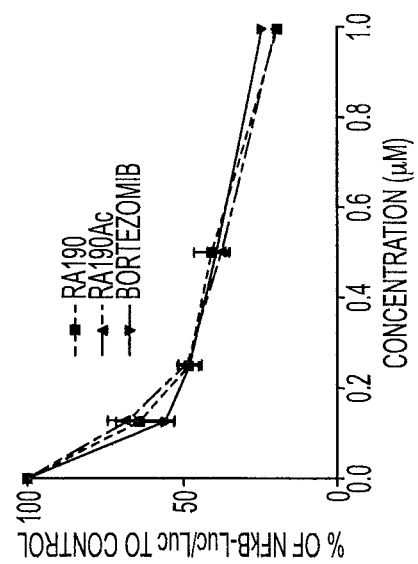
FIG. 19
FIG. 18
FIG. 20

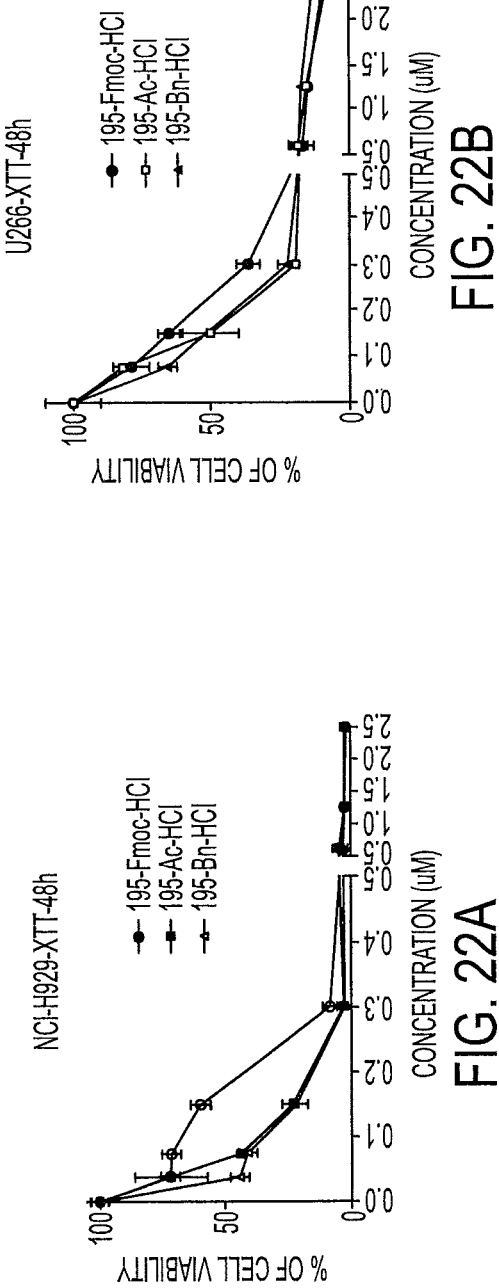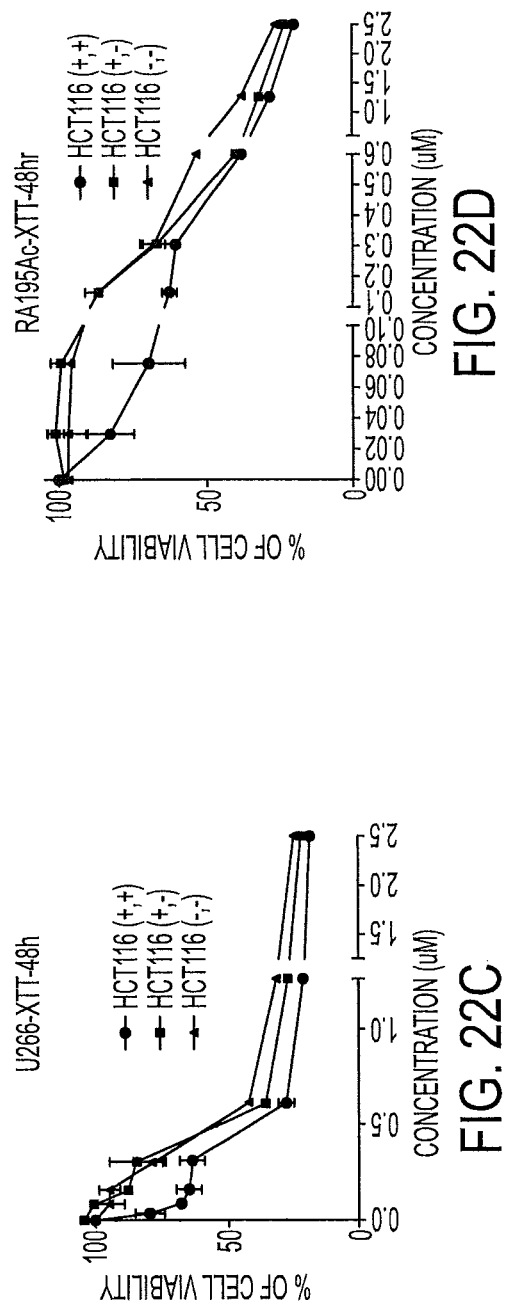

BIS-BENZYLIDINE PIPERIDONE PROTEASOME INHIBITOR WITH ANTICANCER ACTIVITY

CROSS-REFERENCE TO PRIOR APPLICATIONS

This application is a Divisional of U.S. patent application Ser. No. 14/889,768, now U.S. Pat. No. 9,913,834, filed Nov. 6, 2015, which is a U.S. National Stage Application of International Application No. PCT/US2014/037031, filed May 6, 2014, which claims the benefit and priority of U.S. Provisional Patent Applications Ser. Nos. 61/820,884 (filed 8 May 2013) and 61/838,156 (filed 21 Jun. 2013) which applications are incorporated herein by reference to the extent permitted by applicable statute and regulation.

U.S. GOVERNMENT SUPPORT

This invention was made with government support under grant number CA098252, awarded by the National Institutes of Health. The Government has certain rights in the invention.

BACKGROUND OF THE INVENTION

Area of the Art

The present invention relates to a class of novel molecules with Michael acceptors. These molecules are based from a bis-benzylidine piperidone backbone and can be used as therapeutic agents against various types of cancers. Specifically, these molecules work as proteasome inhibitors and bind to the RPN13 subunit of the 19S regulatory particle.

Description of the Background Art

Protein degradation is exquisitely regulated within the cell to maintain protein homeostasis and eliminate misfolded or damaged proteins.[32] Targeted degradation of regulatory proteins by the ubiquitin-proteasome system (UPS) is central to many signaling cascades including those that govern cell proliferation and is exploited by many infectious agents.[12] The degradation of a target protein is signaled by repeated covalent linkage of ubiquitin mediated by E3 ubiquitin ligases, of which hundreds have been described. Upon the attachment to the target of extended chains of ubiquitin, each conjugated via lysine 48, the poly-ubiquitinated proteins are recognized by two proteasome subunits, RPN10 and RPN13 within the 19S regulatory particle (RP).[19,30,31] The 19S RP recycles the ubiquitin by its removal from the target protein, and unfolds the target protein while passing it to the 20S core particle of the proteasome for degradation. RPN13 binds to both UCH37, enhancing its deubiquitinase activity[28], and to RPN2 that modulates the translocation and subsequent degradation of substrates by the 20S.[11] The 20S core particle contains three catalytic subunits, $\beta 1$, $\beta 2$ and $\beta 5$, with caspase, trypsin, and chymotrypsin-like activities respectively.[32] Degradation occurs progressively via nucleophilic attack of the substrate amide bond by a Threonine within the $\beta$-subunit active site. The inhibitors bortezomib and carfilzomib principally inhibit chymotrypsin-like proteolysis.[7]

The increased reliance upon proteasomal function in cancer cells can provide a therapeutic window.[17] Bortezomib was approved for the treatment of relapsed multiple myeloma (MM) and mantle cell lymphoma[7], and Carfilzomib was recently approved for patients with MM progression while on or after treatment with bortezomib and an immunomodulatory agent. The efficacy of these proteasome inhibitors has been attributed to the activation of the unfolded protein response (UPR) and endoplasmic reticulum stress due to toxic accumulation of protein aggregates, inhibition of NF-κB and TNFα signaling, increases in reactive oxygen species (ROS) and stabilization of tumor suppressors such as p53.[10] In human papillomavirus (HPV)-related cancers the E6 viral oncoprotein drives transformation by co-opting the cellular E3 ubiquitin ligase E6AP to polyubiquitinate target E6-binding proteins, notably tumor suppressors such as p53 and PDZ-family members including DLG-1, and trigger their rapid degradation.[18,25,26] Preclinical findings suggest that HPV-transformed cells are preferentially sensitive to bortezomib as it recovers their levels of E6-targetted tumor suppressor proteins, and triggers apoptosis.[23,32]

Unfortunately, bortezomib induces thrombocytopenia and neuropathy (associated with off-target activity,[4] and the emergence of disease resistance remains a clinically significant problem.[29] Carfilzomib has similar issues. New orally delivered drugs targeting distinct activities of the proteasome are needed to increase dosing flexibility, overcome resistance and reduce side effects.[9] Here we describe a new compound, RA190, which is orally bioavailable, which inhibits proteasomal degradation by binding to a novel proteasome target, the ubiquitin receptor RPN13, which and shows promising activity against bortezomib-resistant MM, ovarian and HPV-associated cancers.

SUMMARY OF THE INVENTION

The present invention relates to a class of novel molecules containing Michael acceptors. In some embodiments, these molecules can be based from a bis-benzylidine piperidone structure and can also be used as therapeutic agents against various types of cancers. The molecules described herein can bind to RPN13 cysteine 88 in the ubiquitin- and proteasome-binding Pru domain, rather than the UCH37-interaction domain, and inhibit proteosomal function. Furthermore, residues surrounding C88 can interact with the molecules of the invention. Molecules of the invention can bind sub-stoichiometrically to proteasome[27] and exist free of proteasome in cells. The molecules of this invention are potent proteasome inhibitors of a variety of cancer cells, especially those that are HPV$^+$ and/or those expressing high rates of protein synthesis such as ovarian and colon cancer and multiple myeloma.

In addition, the molecules of the invention comprise an enone moiety. Elimination of Michael acceptor properties by the addition of thiol or complete removal of the enone moiety nullify drug activity in cytotoxic and functional assays. In addition, substitution of L- for D-phenylalanine or conversion of the carboxyl moiety to oxime reduces the potency of the molecules.

In some embodiments, the molecules of the invention can be formulated in 20% (w/v) b-hydroxyisopropyl-cyclodextrin in water. In such cases, the oral availability was only approximately 7% that of the i.p. delivery but proved sufficient for significant antitumor effects and proteasomal inhibition in vivo. The molecules are also effective via topical administration at 4% in Cremophor, suggesting potential for treatment of HPV+ intraepithelial neoplasia for cancer prevention.

Another important feature of the molecules of the invention is their low toxicity. The side effects of bortezomib and carfilzomib, including neuropathy and thrombocytopenia, remain important clinical concerns.[29] RPN13 is one of two major ubiquitin receptors in the RP,[14,19,30,31] and Rpn13 knockout (KO) mice are viable, suggesting that molecules targeting RPN13 (such as those described in this invention) may have a favorable toxicity profile.[2] Indeed, oral treatment with at least one bis-benzylidine piperidone molecule was well tolerated, producing no significant difference in hematologic or clinical chemistry parameters as compared with vehicle, and it did not affect weight gain or compromise spontaneous antitumor immunity, further suggesting a promising safety profile. Additionally, unlike many other anticancer chemotherapeutic agents, the molecules of the invention described herein do not compromise immune function. Specifically, they do not compromise E7-specific CD8+ T cell response to TC-1 tumors thus implying that it may therefore be possible to combine treatment of cervical cancer with at least one molecule described herein (RA190) and therapeutic vaccines targeting HPV E6 and/or E7.[36]

In addition, in some embodiments, the molecules of the invention can be used synergistically with current cancer therapeutics that also target proteasome function (such as bortezomib). This can especially be the case in instances where the second therapeutic targets a distinct component of the proteasome and/or resistance to the second therapeutic has occurred.

DESCRIPTION OF THE FIGURES

FIG. 1A is a graph showing percent cell viability;
FIG. 1B is a graph showing percent cell viability;
FIG. 1C is a graph showing percent cell viability;
FIG. 1D is a graph showing percent cell viability;
FIG. 1E is a graph showing percent cell viability;
FIG. 1F is a graph showing percent cell viability;
FIG. 4A is a bar graph depicting the amino acid residues implicated in the RA190 and RPN13 interaction;
FIG. 4B is a bar graph depicting the amino acid residues implicated in the RA190 and RPN13 interaction;
FIG. 4C is a model showing the lowest energy modeled structure for human RPN13 Pru~RA190;
FIG. 6G is a graph showing Annexin-V expression in cells treated with Bz;
FIG. 6H is a bar graph showing the amount of active caspase-3 in cells;
FIG. 6I is a representative flow cytometry analysis of MM.1S cells treated as in (FIGS. 6E-6G) and stained for active caspase-3;
FIG. 6J is an immunoblot of lysates from HeLa cells either untreated (C) or treated with 1 µM RA190 (190) or bortezomib (Bz);
FIG. 6K is an immunoblot of lysates from MM1.S cells either untreated (C) or treated with 0.5 µM RA190 or bortezomib for 6 hr;
FIG. 6L is a graph showing expression of surface HSP90 on HeLa cells treated with 1 mM RA190, bortezomib, or cisplatin as a function of time.
FIG. 7A is a graph showing inhibition of protease function in mice following treatment with RA190;
FIG. 7B is a graph showing inhibition of protease function in mice following treatment with RA190;
FIG. 7C is a graph showing inhibition of protease function in mice following treatment with RA190;
FIG. 7D is a graph showing inhibition of protease function in mice following treatment with RA190;
FIG. 7E is a graph showing inhibition of protease function in mice following treatment with RA190;

FIG. 8A shows a graph showing inhibition of tumor growth and reduction of tumor size in mice carrying NCI-H929-GFP-luc human tumor cells as a function of treatment with RA190;

FIG. 8B shows representative bioluminescence images of mice in (FIG. 8A) before (top panel) and after (bottom panel) treatment;

FIG. 8C shows a graph showing decrease in bioluminescence of EΩ-luciferase tumor cells in mice treated with RA190;

FIG. 8D shows representative bioluminescence images of mice in (FIG. 8C) before (upper panel) and after (lower panel) treatment;

FIG. 9E shows a bar graph showing PGPH activity as a function of treatment with RA190 or bortezomib;

FIG. 9F shows a bar graph showing the degradation of Ub-AMC;

FIG. 9G shows a bar graph showing the degradation of Ub-AMC;

FIG. 9H shows the effects on the activity of 19S RP as a function of treatment with corresponding compounds;

FIG. 10A shows cell viability as a function of treatment with indicated compounds;

FIG. 10B is an immunoblot showing the proteasome activity of cells treated with the indicated compound;

FIG. 10C is an immunoblot showing the proteasome activity of cells treated with the indicated compound;

FIG. 18 shows a graph showing the effect of various compounds on HeLa cell viability;

FIG. 19 shows a graph showing a 20S proteasome inhibition assay;

FIG. 20 shows a graph showing the effect of various compounds on NF$_K$B;

FIGS. 22A-D show a series of data graphs showing the effect of indicated compounds on the viability of various cancer cell lines;

DETAILED DESCRIPTION OF THE INVENTION

Figure 1G:
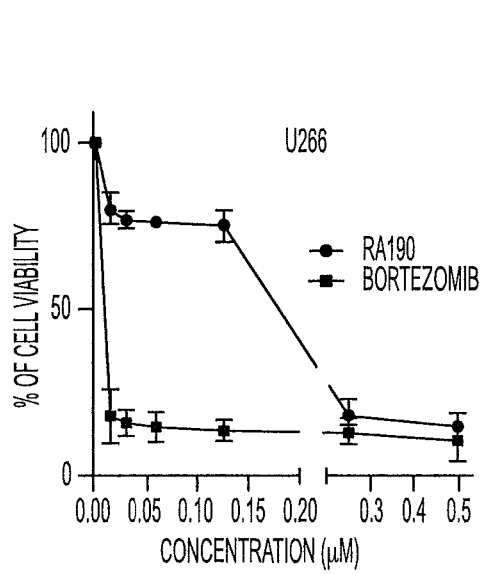
FIG. 1G is a graph showing percent cell viability.
Figure 1H:
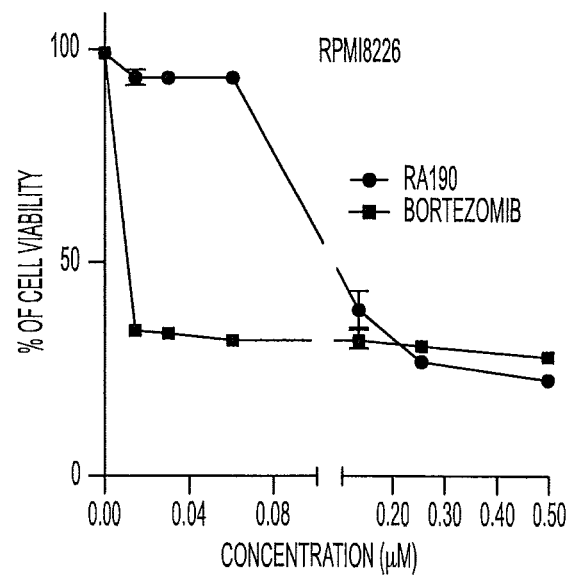
FIG. 1H is a graph showing percent cell viability.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide one example of one application of the invention.

Activity of Bis-Benzylidine Piperidone Derivatives

We recently described a series of 1,3-diphenylpropen-1-one (chalcone)-based derivatives bearing a variety of amino acid substitutions on the amino group of the 4-piperidone, including RA1, which inhibits ubiquitin-mediated protein degradation and preferentially kills cervical cancer cells.[6] The α,β ketone represents the minimal molecular determinant for inhibition, which occurs without affecting CP activity.[3] To improve activity and solubility, and to probe their pharmacophore, we generated a series of derivatives with varying substituents in the aromatic ring to modulate the acceptor character of the enone system including o- and p-halogens, and different amino acids at the amine functionality of 4-piperidone. Because our previous work suggested its importance for proteasome inhibitory activity[6], most RA compounds incorporated phenylalanine and/or substituted phenylalanine. To overcome the poor solubility and pharmacokinetics of our previous generation molecules, we employed an amide in lieu of a urea linkage between amino acids and 4-piperidone. We synthesized RA166 and RA201 with chlorine and fluorine at the ortho position of the aromatic rings and phenylalanine attached to the 4-piperidone, and additional compounds in which histidine or tyrosine (RA213) are substituted for phenylalanine, as well as RA181 with no substituent. Earlier studies suggested the value of two chlorine atoms on each phenyl moiety and thus we synthesized RA190 and RA190Ac, which differ in the phenylalanine and amide conjugation compared to the urea conjugation in our early generation molecule RA1.[6]

Using a variety of cancer cell lines, cell viability was determined with an 2,3-bis (2-methoxy-4-nitro-5-sulfophenyl)-5-[(phenylamino)carbonyl]-2H-tetrazolium hydroxide (XTT) assay after 48-hr treatment with titrations of each compound (Table 1). Activity against several cell lines known to be sensitive to proteasome inhibitors was observed, including those derived from cervical cancer (HeLa, CaSki, and SiHa), MM (ANBL6,MM.1S, NCI-H929, U266, and RPMI-8226), colon cancer (HCT116), and ovarian cancer (ES2 and OVCAR3; Table 1; FIGS. 1A through 1H). FIGS. 1A-H show that RA190 causes a toxic accumulation of polyubiquinated proteins. FIGS. 1 A-D show percent cell viability of RPMI-8226, ANBL6, and their respective in vitro selected bortezomib-resistant cell lines RPMI-8226-V$_{10}$R and ANBL6-V$_{10}$R as a function of 48 hr treatment with the indicated compounds. FIGS. 1 E-H show percent cell viability of indicated MM cell lines as a function of 48 hr treatment with the indicated compounds. Because RA190 consistently exhibited the most potent antiproliferative effects against MM lines (half maximal inhibitory concentration [IC50]≤0.1 μM) and HPV transformed cells (IC50≤0.3 μM), it was the focus for further analysis. RA190 was less efficacious against HPV− (IC50>5 μM for HT3 and C33A, Table 1) than HPV+ (HeLa, CaSki, and SiHa) cervical cancer cell lines. Likewise, the HPV16-immortalized oral keratinocyte line HOK-16B was more sensitive to RA190 than either HaCaT cells (HPV−, spontaneously immortalized keratinocytes) or FaDu (HPV− head and neck cancer cells).

TABLE 1

Impact of bis-benzylidine piperidone derivatives and proteasome inhibitors on the viability of cell lines (IC50 values in μM).

| Compound (RA-) | HeLa | CasKi | SiHa | HT3 | C33A | FaDu | HOK-16B | SKOV3 | OVCAR3 | ES-2 | MM.1S | NCI-H929 | RPMI8226 | HaCaT |
|---|---|---|---|---|---|---|---|---|---|---|---|---|---|---|
| 166 | 0.6 | 1.5 | 2.0 | >5 | >5 | >5 | >5 | >2.5 | >5 | NT | NT | NT | NT | >2.5 |
| 181 | 0.35 | 2.0 | 2.0 | >5 | >5 | >5 | >5 | >2.5 | >5 | NT | NT | NT | NT | >2.5 |
| 190 | 0.15 | 0.3 | 0.75 | >5 | >5 | >2.5 | 0.6 | >2.5 | 2.0 | 0.75 | 0.035 | 0.05 | 0.10 | >2.5 |
| 196 | 0.6 | 1.0 | 2.0 | >5 | >5 | >5 | 3.0 | >2.5 | 2.5 | NT | NT | NT | NT | >2.5 |

TABLE 1-continued

Impact of bis-benzylidine piperidone derivatives and proteasome inhibitors on the viability of cell lines (IC50 values in µM).

| Compound (RA-) | Cell Lines | | | | | | | | | | | | | | |
|---|---|---|---|---|---|---|---|---|---|---|---|---|---|---|---|
| | HeLa | CasKi | SiHa | HT3 | C33A | FaDu | HOK-16B | SKOV3 | OVCAR3 | ES-2 | MM.1S | NCI-H929 | RPMI8226 | HaCaT |
| 201 | 0.35 | 2.5 | 2.0 | >5 | >5 | >5 | 1.5 | >2.5 | >5 | NT | NT | NT | NT | >2.5 |
| 213 | 0.6 | 0.6 | 2.5 | >5 | >5 | >5 | 1.5 | >2.5 | >5 | NT | NT | NT | NT | >2.5 |
| 190Ac | 0.17 | 0.3 | 1.0 | >5 | >5 | >2.5 | 0.75 | >2.5 | 2.0 | NT | 0.05 | 0.075 | 0.15 | >2.5 |
| Bortezomib | 0.03 | 0.05 | 1.0 | <2.5 | <2.5 | <2.5 | 0.02 | <2.5 | <2.5 | 0.02 | 0.005 | 0.005 | 0.01 | <2.5 |
| MG132 | 0.75 | 0.5 | 2.0 | >5 | >5 | >2.5 | 0.7 | >2.5 | NT | NT | NT | NT | NT | >2.5 |

Figure 9B:
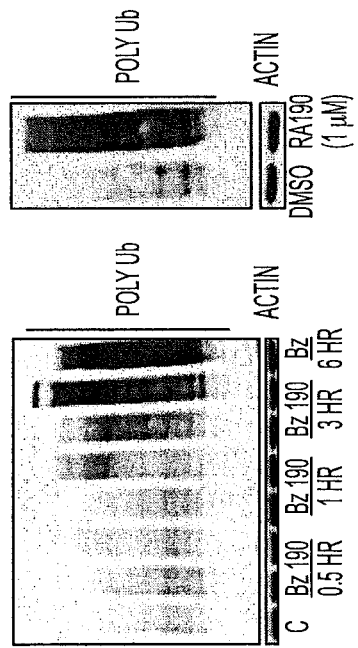
FIG. 9B shows an immunoblot of lysates from NCI-H929 cells treated with 0.5 μM RA190 (190) or 0.1 μM bortezomib (Bz)
Figure 9D:
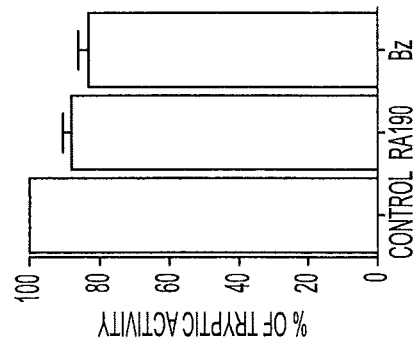
FIG. 9D shows a bar graph showing tryptic activity as a function of treatment with RA190 or bortezomib.
Figure 9A:
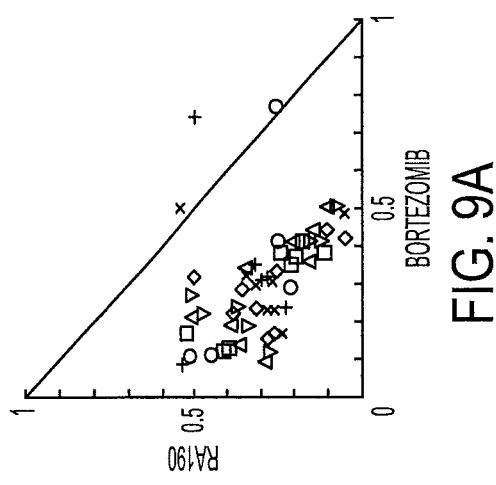
FIG. 9A shows an analysis of drug combination index (CI) for RA190 and bortezomib.

MM cells may acquire bortezomib resistance by several mechanisms.[22,28] We tested RA190 potency against two MM cell lines that developed resistance after extended culture in bortezomib,[22] and it was equally efficacious against both the bortezomib-resistant derivative lines and the parental lines, consistent with a mode of action distinct from bortezomib (FIGS. 1A-D). Furthermore, the combination of RA190 and bortezomib provides a synergistic effect on the loss of cervical cancer cell viability (FIG. 9A). In FIG. 9A, HeLa cells were treated with RA190 (0-300 nM) and/or bortezomib (0-30 nM) alone or in combination for 48 hr, and cell viability determined. The combination indices and a normalized isobologram were calculated using Compusyn software with IC50 of 184 nM for RA190 and 21.7 nM for bortezomib.

RA190 Triggers Accumulation of Polyubiquitinated Proteins

Figure 1I:
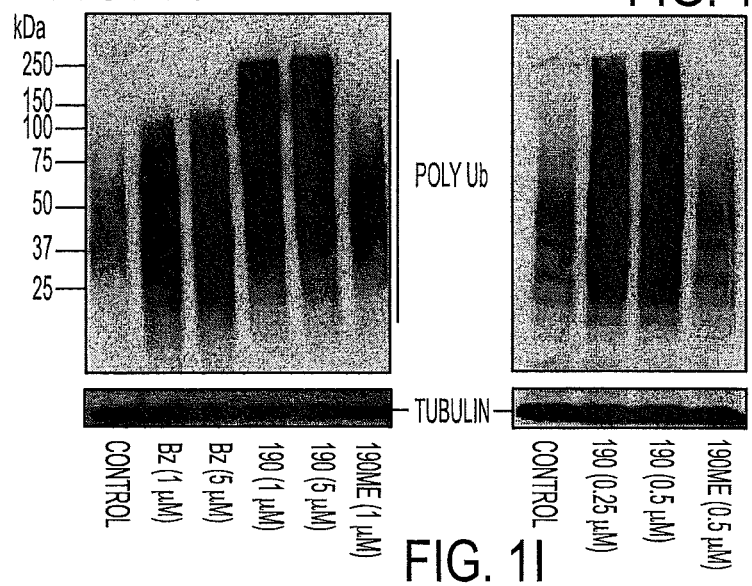
FIG. 1I is a western blot of lysates from HeLa cells treated with RA190 (190), RA190ME (190ME), or bortezomib (Bz) for 4 hr (left) or 12 hr (right) at the concentrations indicated.
Figure 1J:
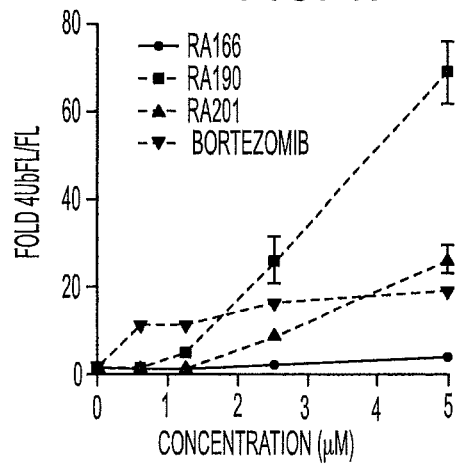
FIG. 1J shows luciferase activity of HeLa cells transiently transfected with either tetra-ubiquitin-fused firefly luciferase (4UbFL) or FL plasmids as a function of proteasome inhibition by various compounds.
Figure 9C:
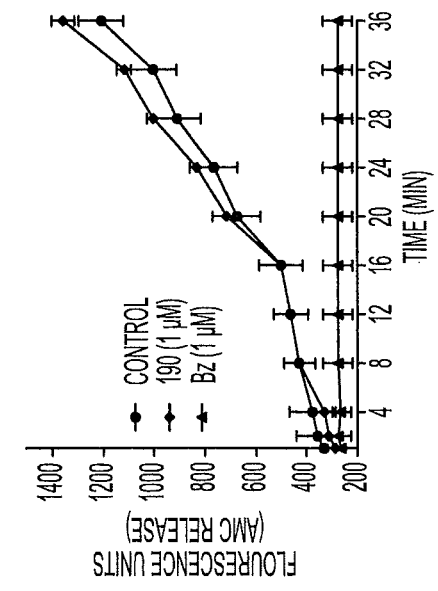
FIG. 9C shows a line chart showing proteasome activity as a function of treatment with RA190 or bortezomib.

FIGS. 1A-1F show that RA190 causes a toxic accumulation of polyubiquitinated proteins. FIGS. 1 A-D show percent cell viability of RPMI-8226, ANBL6, and their respective in vitro selected bortezomib-resistant cell lines RPMI-8226-$V_{10}$R and ANBL6-$V_{10}$R as a function of 48 hr treatment with the indicated compounds. FIGS. 1 E-H show percent cell viability of indicated MM cell lines as a function of 48 hr treatment with the indicated compounds. FIG. 1I is a western blot of lysates from HeLa cells treated with RA190 (190), RA190ME (190ME), or bortezomib (Bz) for 4 hr (left) or 12 hr (right) at the concentrations indicated. FIG. 1J shows luciferase activity of HeLa cells transiently transfected with either tetra-ubiquitin-fused firefly luciferase (4UbFL) or FL plasmids as a function of proteasome inhibition by various compounds. Because compounds related to RA190 are proteasome inhibitors,[3] we examined its impact on the levels of polyubiquitinated proteins in HeLa and CaSki cells by anti-K48-linked ubiquitin immunoblot analysis. RA190 treatment of HeLa cells (4 hr) dramatically increased the levels of K48-linked polyubiquitinated proteins similarly to bortezomib (FIG. 1I) and in a dose-dependent manner. However, accumulated K48 polyubiquitinated proteins observed following exposure to RA190 exhibited a higher molecular weight than that seen in bortezomib-treated cells (FIG. 1I) and occurred more rapidly (FIG. 9B). In FIG. 9B, lysates from NCI-H929 cells treated with 0.5 µM RA190 (190) or 0.1 µM bortezomib (Bz) for the indicated periods of time (left) or from CaSki cells treated with DMSO or RA190 for 12 hr (right) were subjected to immunoblot analysis using anti-Ubiquitin antibody. Actin was used as a loading control. These results suggest that the toxicity exerted by RA190 for cervical cancer cells is associated with a prior accumulation of high-molecular-weight polyubiquitinated proteins and occurs by a mechanism distinct to bortezomib. Indeed, unlike bortezomib, RA190 does not inhibit CP chymotryptic, tryptic, and PGPH activities (FIGS. 9C-E). In FIG. 9C-E, purified 20S proteasomes were treated for 30 min with or without compounds (1 µM) prior to the addition of the specific fluorogenic substrate for chymotryptic (9C), tryptic (9D) or PGPH (9E) hydrolytic proteasome capacities. Mean±SD fluorescence associated with AMC released from the substrate was measured at 45 min. Inhibition of RP deubiquitinase activity can produce a similar accumulation of high-molecular weight polyubiquitinated protein as seen for RA190.[21] However, the degradation of Ub-AMC by either purified recombinant UCH37 (with or without the addition of RPN13) or purified RP was minimally affected by RA190, suggesting that it does not inhibit the RP deubiquitinases (FIGS. 9F-H). In FIGS. 9F and 9G, hydrolysis of ubiquitin—AMC (0.5 µM) alone (grey), or with 20 nM RPN13 (brown), 2 nM UCH37 (black), a mixture of 2 nM UCH37 and 20 nM RA190 (blue), a mixture of 2 nM UCH37 and 20 nM RPN13 (red), and a mixture of 2 nM UCH37, 20 nM RPN13 and 20 nM RA190 (yellow) monitored by fluorescence (JASCO FP-6200 spectrofluorometer; λex=380 nm, λem=460 nm). DMSO was added to all samples to a final concentration of 0.1% (upper panel). The effect of DMSO is highlighted by including ubiquitin—AMC (0.5 µM) hydrolysis with 2 nM UCH37 lacking DMSO (orange, bottom panel). In FIG. 9H, purified 19S RP (500 nM) in buffer was treated with corresponding compounds 30 min at 37° C. and AMC cleavage was measured with a fluorometer for 20 min. Ubal was used as a positive control.

RA190 Stabilizes Tetraubiquitin-Fused Luciferin

A tetraubiquitin-firefly luciferase (4UbFL) reporter, in which four copies of ubiquitin (G76V) are genetically fused to the N terminus of firefly luciferase (FL), is rapidly degraded by the proteasome whereas FL alone has a much longer half-life. Importantly, treatment of cells expressing 4UbFL with proteasome inhibitors results in its stabilization and an increase in luciferase activity, providing a validated approach to assess proteasome function in live cells.[24] Two days after transfection with either 4UbFL or FL expression vectors, HeLa cells were treated for 4 hr with bortezomib and luciferase-driven bioluminescence was dramatically increased in cells expressing 4UbFL but not FL (FIG. 1J). Thus, the ratio of bioluminescence observed in cells transfected with 4UbFL versus FL was used to assess the proteasome inhibition by the active compounds in the series, revealing RA190 as more potent than others, including RA166 and RA201 (FIG. 1J).

RA190 Covalently Binds to the RP Subunit RPN13

Figure 9K:
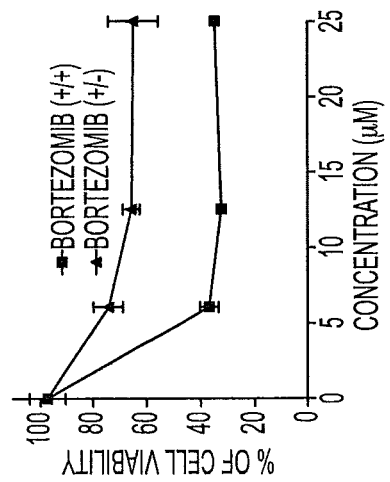
FIG. 9K is a graph showing cell viability.
Figure 9J:
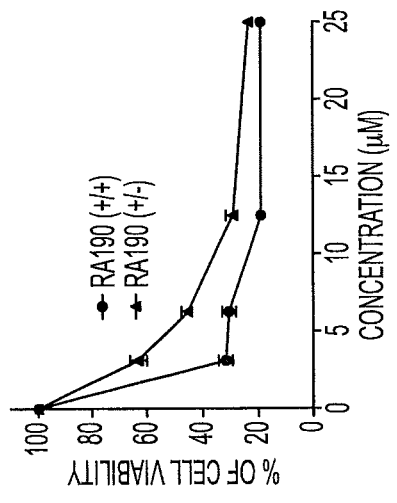
FIG. 9J is a graph showing cell viability.
Figure 9I:
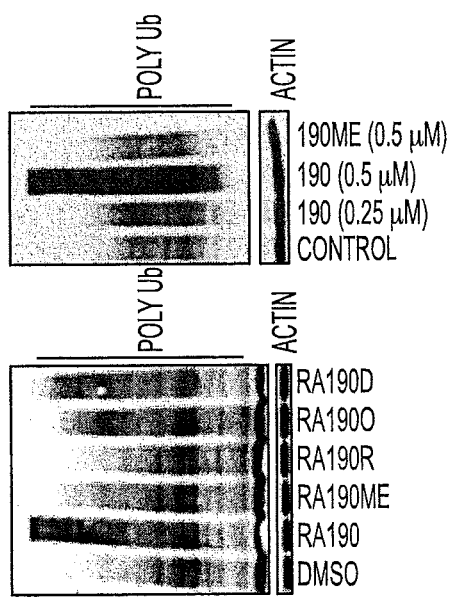
FIG. 9I shows an immunoblot showing the effect on proteasome activity by various compounds.

Removal of the olefin bond from RA190 by treatment with β-mercaptoethanol (forming RA190ME) significantly reduced its potency in both cell killing and polyubiquitin accumulation assays (FIGS. 1I and 9I), suggesting it is a Michael acceptor with olefin bonds that are susceptible to nucleophilic attack. In FIG. 9I, HeLa cells were treated with DMSO, RA190, RA190ME, RA190R, RA190O and RA190D at 1 μM concentration for the period of 4 hr and the cell lysate was subjected to immunoblot analysis with anti-Ubiquitin antibody (left panel). SiHa cells were treated with the indicated compounds for 12 hr and the lysate subjected to Western blot analysis with anti-Ubiquitin antibody (right panel). Actin was used as loading control. Elimination of the enone moiety (RA190R) or conversion of the carboxyl moiety to oxime (RA190O) dramatically reduced activity in cell killing and functional assays (FIG. 9I). Furthermore, washout studies are also consistent with RA190 acting as an irreversible inhibitor (FIGS. 9J and 9K). In FIGS. 9J and 9K, HeLa cells were either continuously incubated for 24 hr with bortezomib or RA190, (+/+), or after a 1 hr exposure period, incubated with fresh inhibitor-free medium for an additional 23 hr (+0, whereupon cell mean viability±SD was determined.

Figure 2A:
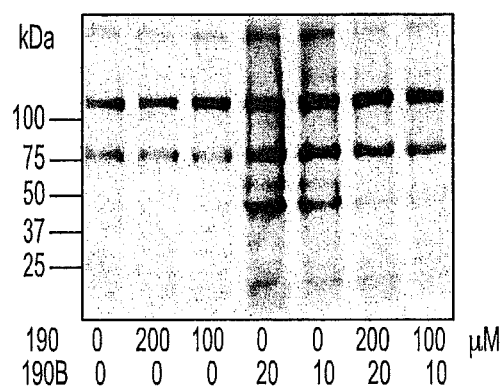
FIG. 2A is an image of a sodium dodecyl sulfate polyacrylamide gel electrophoresis (SDS-PAGE) assay.
Figure 2B:
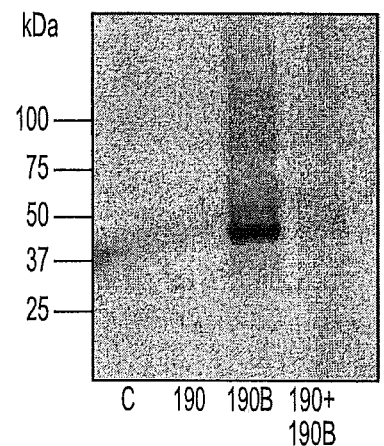
FIG. 2B is an image of an SDS-PAGE assay.

To identify its cellular target, biotin was covalently linked to RA190 via its free amine functionality (RA190B). Biotinylation of RA190 did not affect its potency in cell killing and functional assays (FIGS. 10A-10C). FIGS. 10 A-10E show a series of graphs and immunoblots showing the effects of several compounds on cell viability and proteasome activity. 10A shows cell viability as a function of treatment with indicated compounds. 10B and 10C show immunoblots of the proteasome activity of cell lines treated with the indicated compounds. 10D and 10E show immunoblots of lysates of 293 cells treated for 1 hr at 4° C. with control (DMSO, 10D) or RA190 (10E). In FIG. 10A, HeLa cells were treated with RA190, RA190B or RA190R for 48 hr and mean cell viability±SD was determined. IC50 values were determined in triplicate. In FIG. 10B, HeLa cells were treated for 12 hr and the cell lysate was subjected to immunoblot analysis with anti-Ubiquitin antibody. In FIG. 10C, SiHa cells were treated with the indicated compounds for 12 hr and the lysate subjected to Western blot analysis with anti-Ubiquitin antibody. HeLa cell lysate was treated with RA190B, subjected to SDS-PAGE, and probed with streptavidin-peroxidase following protein transfer to a polyvinylidene difluoride (PVDF) membrane. The streptavidin-peroxidase bound to biotinylated cellular proteins, but a striking new band at 42 kDa appeared in RA190B-treated samples (FIG. 2A). FIGS. 2A-2F show a series of SDS PAGE gels that demonstrate that RA190 covalently binds to RPN 13. 2A shows HeLa cell lysates labeled with RA 190B alone or in the presence of competitor RA190. 2B shows HeLa cell lysates labeled with 500 ng purified 19S proteasome, 10 mM RA190B (190B), and 100 mM RA190 (190). 2C shows cell lysates of 293TT cells transfected with plasmid expressing RPN13, RPN10, UCH37 or HHR23B, or luciferase as a control and labeled with RA190B (20 μM). 2D shows lysates of IPTG induced and uninduced bacteria transduced with expression vector for RPN13 or L2 were labeled with RA190B (20 μM). 2E shows Competition for labeling of RPN13 expressed in bacterial cell lysate with 200 μM RA190 (190), 20 μM RA190B (190B), or both. 2F shows the membrane from (2D) stripped and reprobed with RPN13 antibody. In FIG. 2A, HeLa cells were treated with RA190, RA190B or RA190R for 48 hr and mean cell viability±SD was determined. IC50 values were determined in triplicate. Importantly, RA190 was competitive for this interaction, suggesting specificity. RA190B bound to the 42 kDa protein in a purified RP preparation, and the interaction was similarly competed by RA190 (FIG. 2B).

Figure 2C:
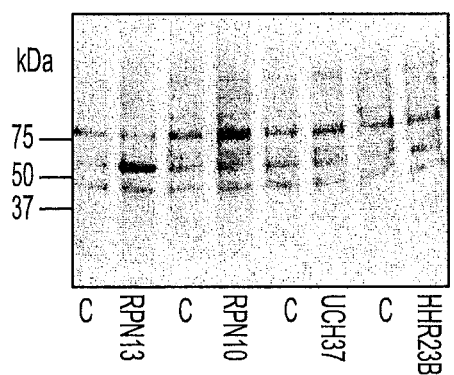
FIG. 2C is an image of an SDS-PAGE assay.

Within the RP there are four proteins (intrinsic ubiquitin receptors RPN10 and RPN13, deubiquitinase UCH37, and shuttling ubiquitin receptor HHR23B) with a molecular weight similar (37-45 kDa) to the cellular target of RA190. These proteins were overexpressed separately in 293TT cells, and the lysates labeled with RA190B and probed with streptavidin-peroxidase. Enhanced labeling of a specific band with RA190B was observed in cell lysates overexpressing RPN13, but not the others (FIG. 2C).

Figure 2D:
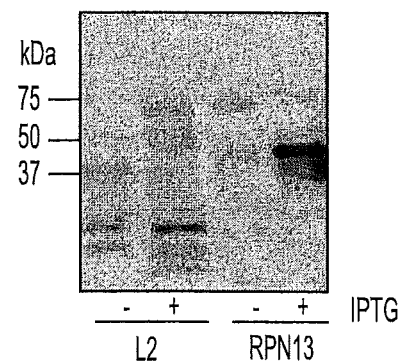
FIG. 2D is an image of an SDS-PAGE assay.
Figure 2E:
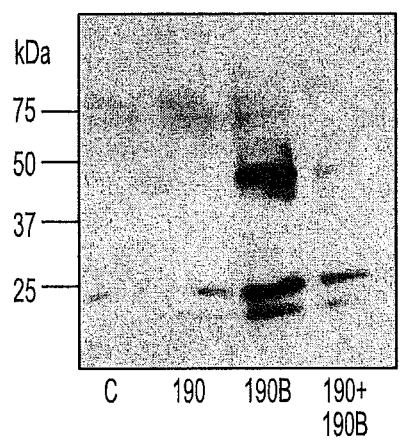
FIG. 2E is an image of an SDS-PAGE assay.
Figure 2F:
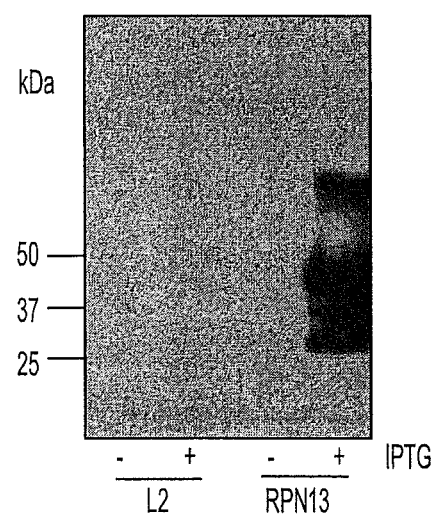
FIG. 2F is an image of an SDS-PAGE assay.
Figure 10D:
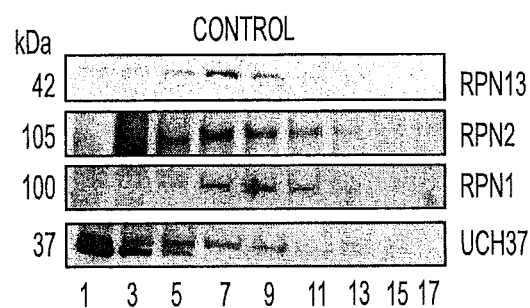
FIG. 10D is an immunoblot of lysates of control cells.
Figure 10E:
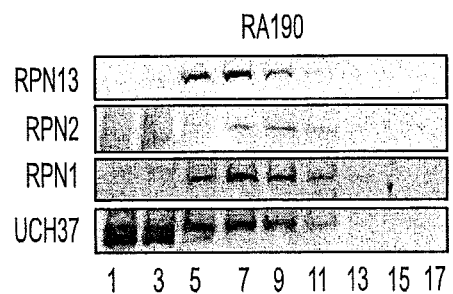
FIG. 10E is an immunoblot of lysates of cells treated with RA190.

To eliminate the possibility that another RP component was required for RA190B interaction, RPN13 or an irrelevant protein (L2) was overexpressed in bacteria. Cell lysate harvested from bacteria either with or without isopropylthio-Malactoside induction of ectopic protein expression was labeled with RA190B and probed by blotting with streptavidin-peroxidase. RA190B reacted strongly with a 42 kDa protein only in lysates of bacteria expressing RPN13 (FIG. 2D). Furthermore, this interaction was competed with by unlabeled RA190 and the presence of RPN13 was confirmed by western blot with RPN13-specific monoclonal antibody (FIGS. 2E and 2F). These findings suggest that RA190 covalently binds directly to RPN13. However, glycerol gradient separation studies indicate that RA190 does not displace RPN13 from proteasome (FIGS. 10D and E). In FIGS. 10D and 10E, lysates of 293 cells treated for 1 hr at 4° C. with control (DMSO, FIG. 10D) or 20 μM RA190 (FIG. 10E) were subjected to 10-40% (v/v) glycerol gradient centrifugation for 15 hr at 4° C. 800 μL fractions were collected and alternate fractions (1,3,5,7,9,11,13,15,17) were analyzed for the presence of proteasomal proteins (RPN13, RPN2, RPN1 and UCH37) by Western blot analysis.

RA190 Ligates to RPN13 Pru Domain

Figure 3A:
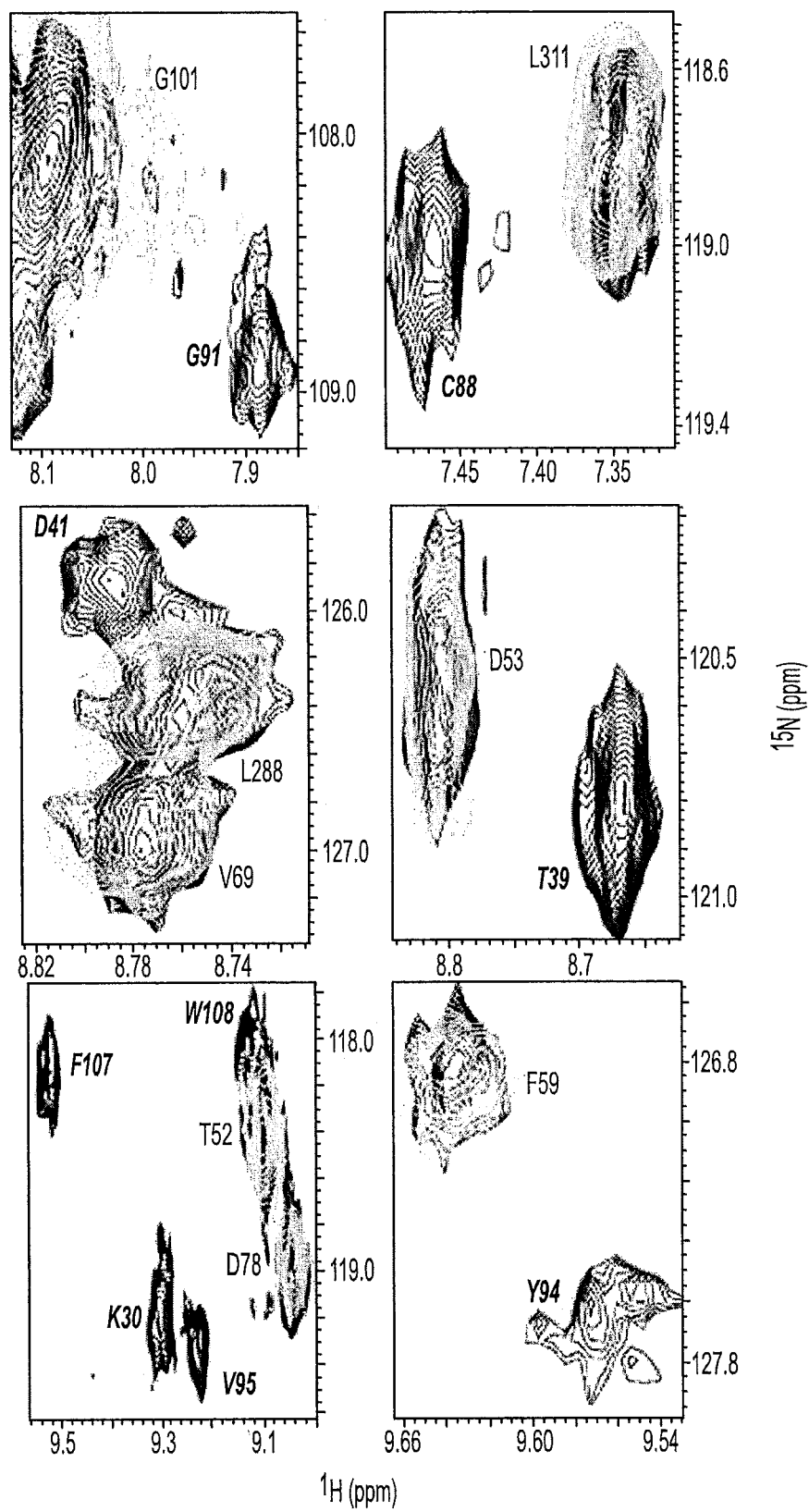
FIG. 3A is an image of a heteronuclear single quantum correlation (HSQC) experiment showing how RA190 interacts with RPN13.
Figure 11A:
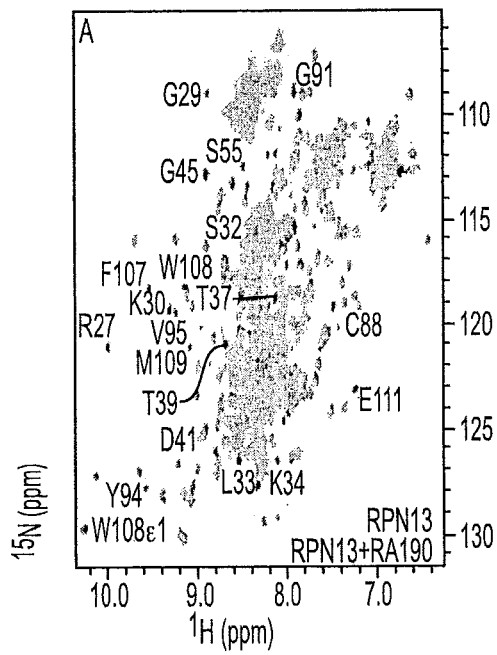
FIG. 11A shows $^1$H, $^{15}$N HSQC spectra of $^{15}$N labeled RPN13 and after incubation with RA190.
Figure 11B:
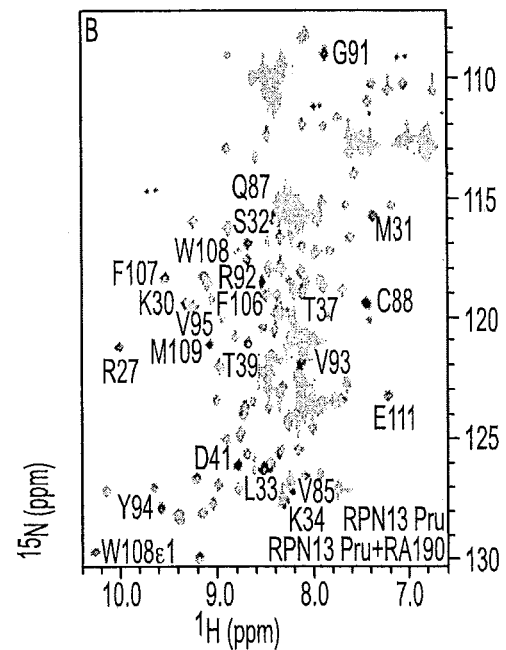
FIG. 11B shows $^1$H, $^{15}$N HSQC spectra of $^{15}$N labeled RPN13 Pru domain and after incubation with RA190.
Figure 11C:
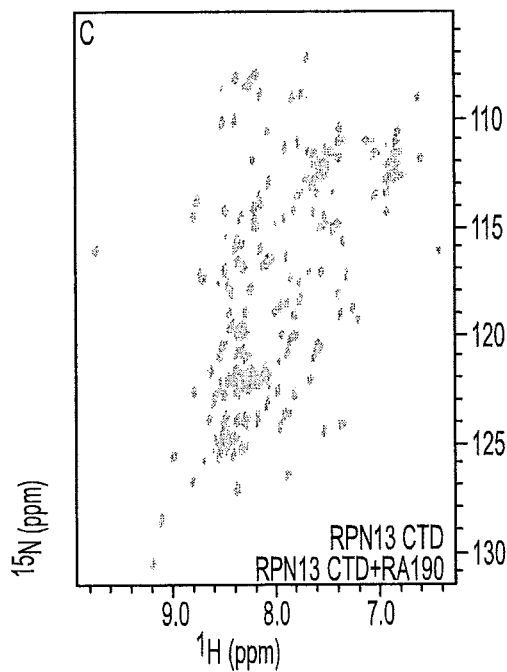
FIG. 11C shows $^{15}$N HSQC spectra of $^{15}$N labeled RPN13 UCH37-binding domain and after incubation with RA190.
Figure 11D:
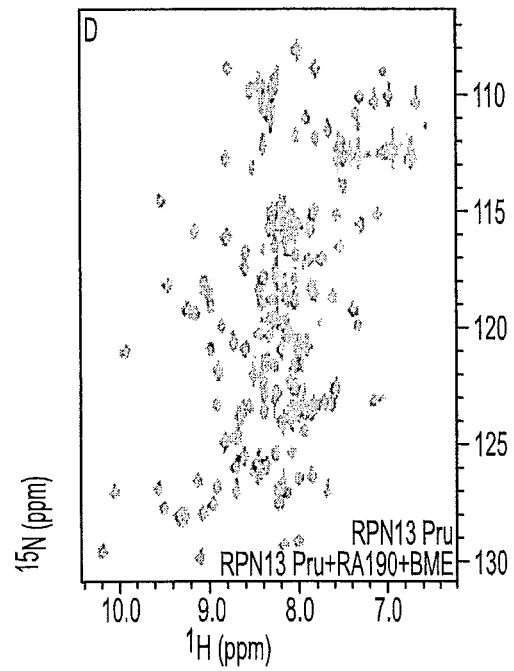
FIG. 11D shows $^1$H, $^{15}$N HSQC spectra of $^{15}$N-labeled RPN13 Pru and after incubation with RA190 and 5 mM β-mercaptoethanol.

RPN13 contains an N-terminal Pru (pleckstrin-like receptor for ubiquitin) domain that binds to ubiquitin[19,31] and the RP, [16,17,20,31] and a C-terminal domain that recruits UCH37 to the proteasome.[17,27,37] We used nuclear magnetic resonance (NMR) to determine whether RA190 targets a specific RPN13 functional domain. Unlabeled RA190 was incubated overnight at 10-fold molar excess and 4° C. with $^{15}$N-labeled RPN13; $^{15}$N-labeled RPN13 (1-150), which includes its Pru domain; or 15N-labeled RPN13 (253-407), which includes its UCH37-binding domain. Unreacted RA190 was removed by dialysis and heteronuclear single quantum coherence (HSQC) spectra were acquired to evaluate the effect of RA190 on the three RPN13 constructs. The spectrum acquired on full-length RPN13 after incubation with RA190 exhibited significant signal loss for specific amino acids in its Pru domain, but not its UCH37-binding domain (FIGS. 3A and 11A). Moreover, RA190 significantly affected NMR spectra recorded on the RPN13 Pru domain (FIGS. 3B and 11B), but not RPN13 (253-407; FIG. 11C). These data indicate that RA190 interacts with the RPN13 Pru domain. FIG. 3 FIGS. 3A-3G show a series of figures that demonstrate how RA190 interacts with the RPN13 Pru Domain. 3A and 3B show enlarged regions of HSQC spectra for $^{15}$N-labeled human RPN13 (3A, black) or RPN13 Pru domain (3B, black) and after RA190 incubation (3A and 3B, orange). 3C-3F shows graphs of LC-MS experiments for RPN13 Pru domain (3C) and RA190-exposed RPN13 (3D), RPN13 Pru domain (3E), and RPN13 Pru $C^{60,80,121}$ A (3F). 3G shows HSQC spectra of $^{15}$N-labeled RPN13 Pru $C^{60,80,121}$ A (black) and after RA190 incubation (orange). FIGS. 11A-11G show a series of spectra data showing that RA190 binds specifically to RPN13 Pru domain and requires its C88 and no reducing agent. 11A shows $^{1}$H, $^{15}$N HSQC spectra of $^{15}$N labeled RPN13 (black) and after incubation with RA190 (orange). 11B shows $^{1}$H, $^{15}$N HSQC spectra of $^{15}$N labeled RPN13 Pru domain (black), and after incubation with RA190 (orange). 11C shows $^{15}$N HSQC spectra of $^{15}$N labeled RPN13 UCH37-binding domain (black), and after incubation with RA190 (orange). 11D shows $^1$H, $^{15}$N HSQC spectra of $^{15}$N-labeled RPN13 Pru (black) and after incubation with RA190 and 5 mM β-mercaptoethanol (orange). 11E shows $^1$H, $^{15}$N HSQC spectra of $^{15}$N labeled RPN13 Pru domain with all of its native cysteines replaced with alanine (RPN13 Pru C/A, black) and following incubation with RA190 (orange). 11F shows $^1$H, $^{15}$N HSQC spectra of $^{15}$N labeled RPN13 Pru domain with C88 replaced with alanine (RPN13 Pru C88A, black) and following incubation with RA190 (orange). 11G shows a graph of a LC-MS experiment on RA190-exposed RPN13 Pru C88A.

β-mercaptoethanol prevented the effect of RA190 on the $^{15}$N-labeled RPN13 Pru domain (FIG. 11D). FIG. 11D shows $^1$H, $^{15}$N HSQC spectra of $^{15}$N-labeled RPN13 Pru (black) and after incubation with RA190 and 5 mM β-mercaptoethanol (orange). To test whether RA190 interacts covalently with the RPN13 Pru domain, we compared liquid chromatography high-resolution mass spectra acquired on our $^{15}$N-labeled RPN13 samples with and without RA190 incubation (FIGS. 3C-3F). Unmodified RPN13 was present in each of the samples exposed to RA190 along with an additional species at a molecular weight shifted by 561.4 Da for the full-length protein (FIG. 3D) and 559.8 Da for the RPN13 Pru domain (FIG. 3E); the expected molecular weight shift caused by RA190 attachment is 561.31 Da. Thus, one RA190 molecule adducted to the RPN13 Pru domain.

RA190 Adducts to RPN13 C88

Figure 11E:
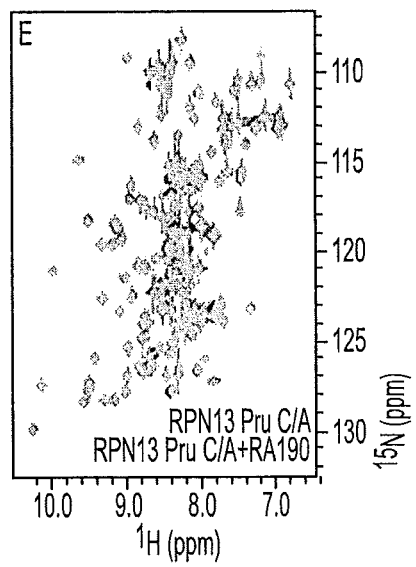
FIG. 11E shows $^1$H, $^{15}$N HSQC spectra of $^{15}$N labeled RPN13 Pru domain with all of its native cysteines replaced with alanine (RPN13 Pru C/A) and following incubation with RA190.
Figure 11F:
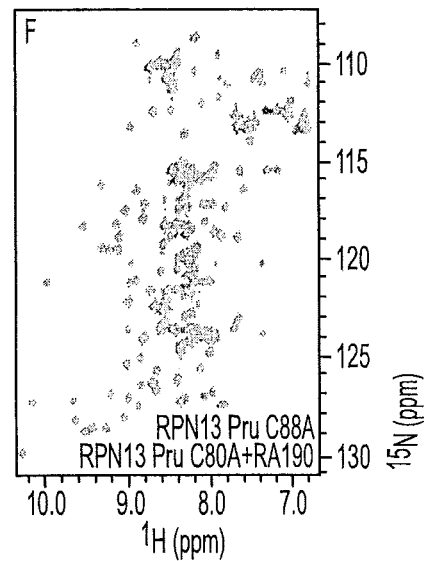
FIG. 11F shows $^1$H, $^{15}$N HSQC spectra of $^{15}$N labeled RPN13 Pru domain with C88 replaced with alanine (RPN13 Pru C88A) and following incubation with RA190.

We used site-directed mutagenesis and NMR to determine the site of RA190 ligation. RA190 no longer interacts with RPN13 Pru domain when its four native cysteines are replaced with alanine (RPN13 Pru C/A). $^{15}$N-labeled RPN13 Pru C/A incubated with RA190 exhibited no changes in HSQC experiments compared to RPN13 Pru C/A alone (FIG. 11E). FIG. 11E shows $^1$H, $^{15}$N HSQC spectra of $^{15}$N labeled RPN13 Pru domain with all of its native cysteines replaced with alanine (RPN13 Pru C/A, black) and following incubation with RA190 (orange).

Figure 11G:
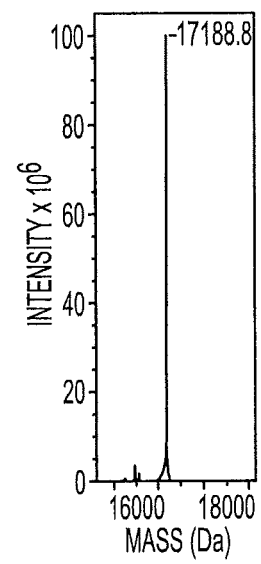
FIG. 11G shows a graph of a LC-MS experiment on RA190-exposed RPN13 Pru C88A.

Inspection of RPN13 NMR spectra acquired with and without RA190 revealed that C88 was significantly affected (FIGS. 3A and 3B), and we tested whether this cysteine is required for the interaction. RA190 did not cause changes to NMR spectra recorded on 15N-labeled RPN13 Pru C88A (FIG. 11F), and only one species of the correct molecular weight for RPN13 Pru C88A was observed by mass spectrometry (FIG. 11G). By contrast, RPN13 Pru $C^{60,80,121}$. A, in which only C88 was preserved, exhibited significant spectral changes upon incubation with RA190 (FIG. 3G) and a molecular weight shift of 559.9 Da by MS (FIG. 3F). These data indicate that RA190 ligates to RPN13 C88.

Model of RPN13 Pru Adducted with RA190

Figure 3B:
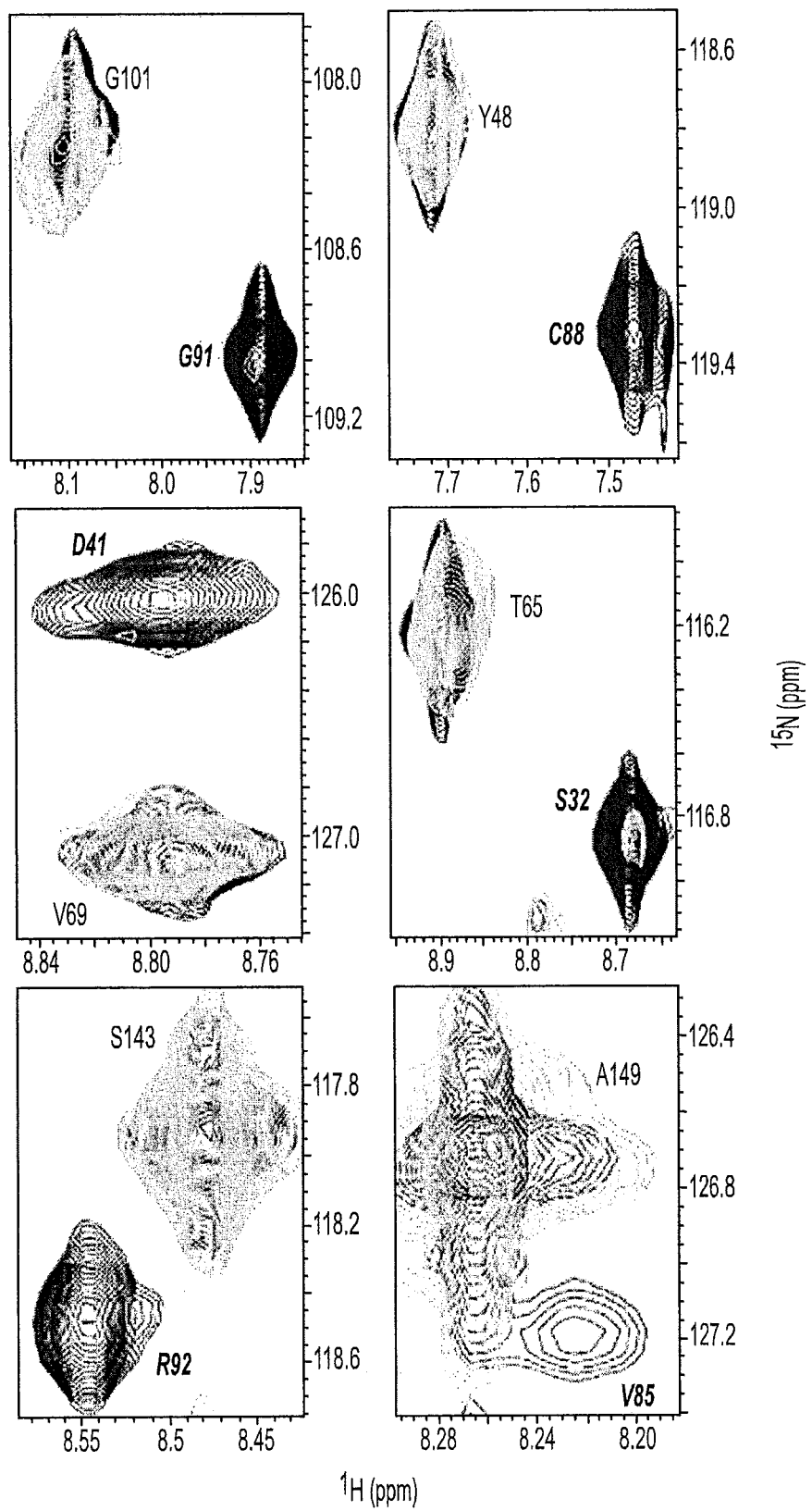
FIG. 3B is an image of a heteronuclear single quantum correlation (HSQC) experiment showing how RA190 interacts with RPN13.
Figure 3C:
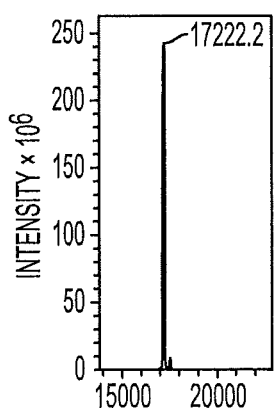
FIG. 3C is a graph of a Liquid Chromatography-mass spectrometry (LC-MS) experiment as indicated.
Figure 3D:
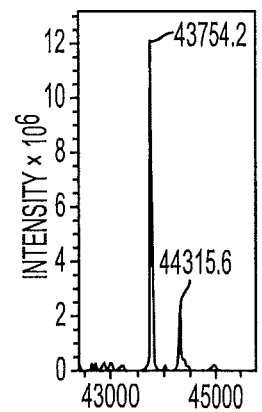
FIG. 3D is a graph of a Liquid Chromatography-mass spectrometry (LC-MS) experiment as indicated.
Figure 3E:
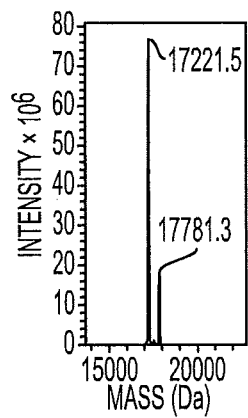
FIG. 3E is a graph of a Liquid Chromatography-mass spectrometry (LC-MS) experiment as indicated.
Figure 3F:
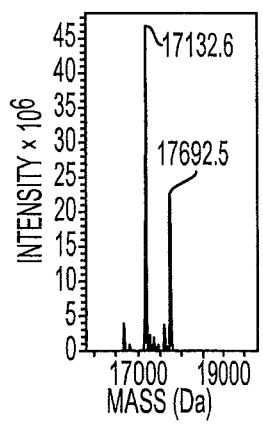
FIG. 3F is a graph of a Liquid Chromatography-mass spectrometry (LC-MS) experiment as indicated.
Figure 3G:
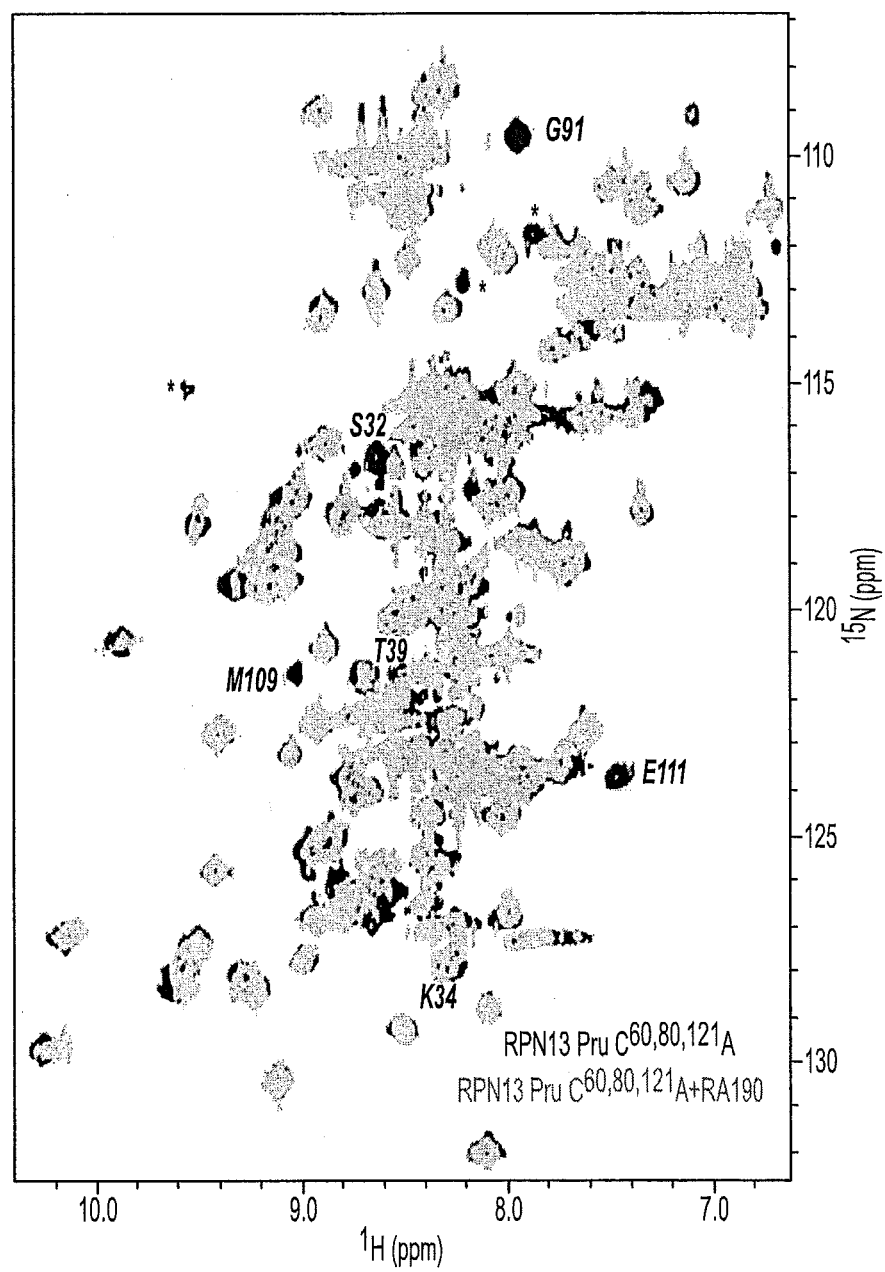
FIG. 3G is a graph showing HSQC spectra of $^{15}$N-labeled RPN13 Pru C[60,80,121] A and after RA190 incubation.
Figure 12C:
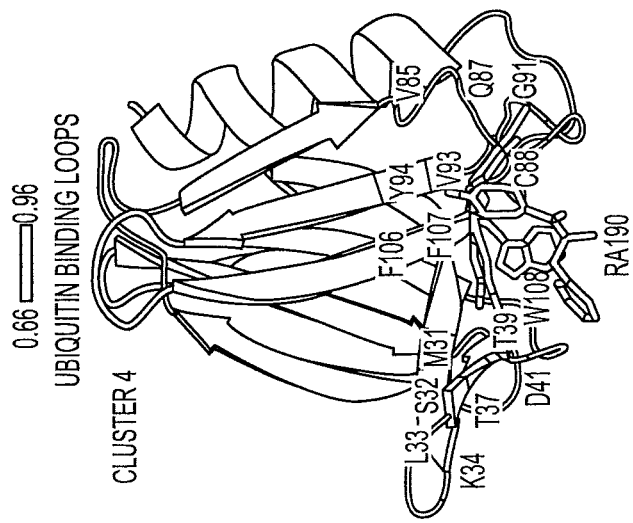
FIG. 12C shows a third model of the human RPN13 Pru~RA190 interaction.
Figure 12B:
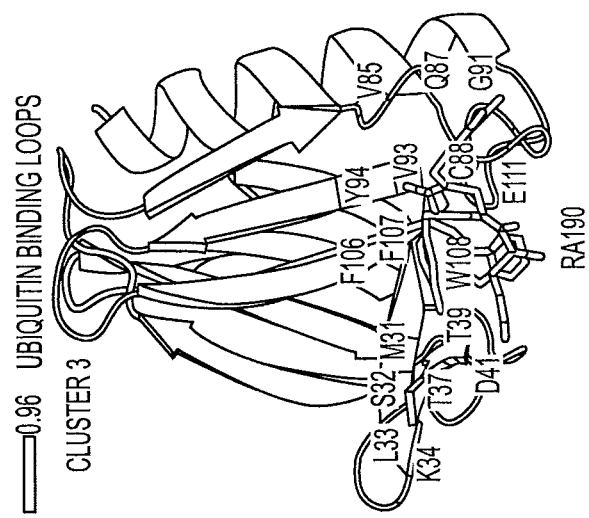
FIG. 12B shows a second model of the human RPN13 Pru~RA190 interaction.
Figure 12A:
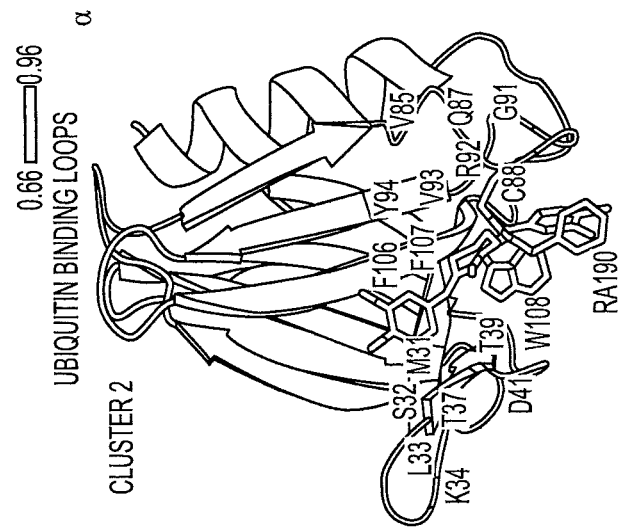
FIG. 12A shows a first model of the human RPN13 Pru~RA190 interaction.
Figure 12D:
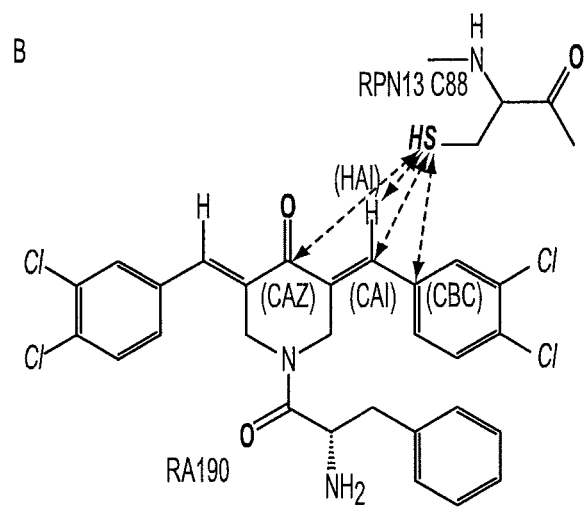
FIG. 12D shows a chemical structure of RA190 and RPN13 C88 side chain.
Figure 12E:
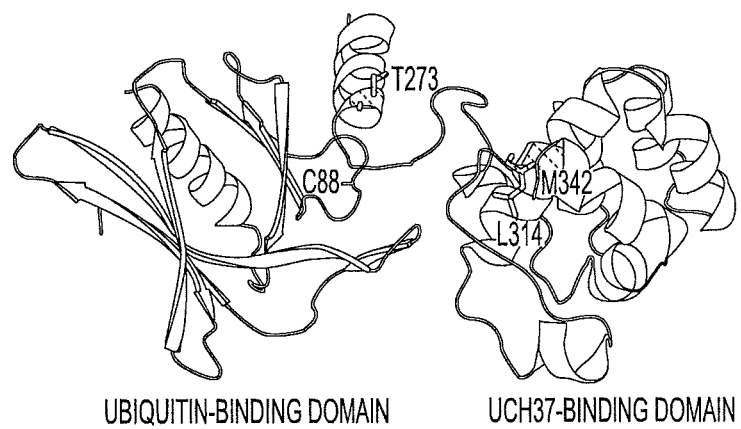
FIG. 12E shows a model of the RPN13 structure highlighting the amino acids from (12F) that shift after RA190 incubation (T273, L314 and M342) in green and C88 in yellow.
Figure 12F:
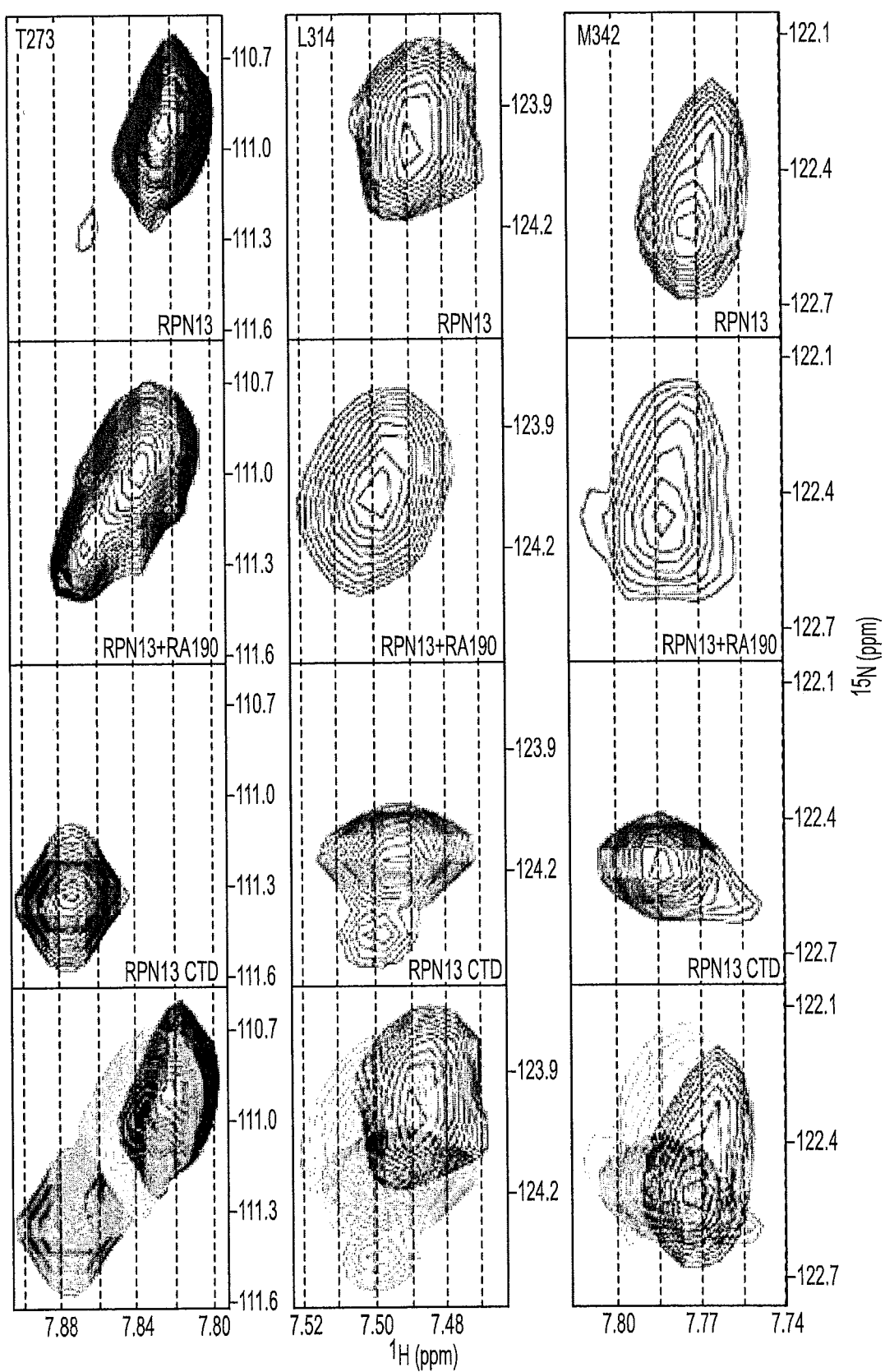
FIG. 12F shows expanded regions of HSQC spectra recorded on RPN13 (top panels) and after incubation with 10-fold molar excess RA190 (second panels) and of RPN13 (253-407, 'RPN13 CTD', third panels). A merger of the three upper panels is displayed in the bottom panels.

We quantified the RA190 effect on RPN13 Pru by integrating the NMR signal of spectra acquired on free and RA190-adducted RPN13 Pru (FIGS. 3B and 11B). The ratio of these values was plotted for each backbone (FIG. 4A) and side chain (FIG. 4B) amide group. FIGS. 4A-4C show a pair of bar graphs and a model showing the amino acid residues implicated in the RA190 and RPN13 interaction. 4A and 4B show graphs of normalized peak intensity attenuation of RPN13 Pru domain backbone (4A) and side chain (4B) amide groups upon binding RA190. 4C shows the lowest energy modeled structure for human RPN13 Pru~RA190. In FIGS. 4A and 4B, the dashed line indicates one SD above average. Unassigned, overlapping, or proline groups are excluded from this analysis and indicated (*). This analysis highlighted RPN13 Pru amino groups that are significantly affected by RA190 and was used to generate model structures of RPN13 Pru adducted with RA190 in HADDOCK.[15] The amino acids most affected by RA190 map to a region opposite RPN13 ubiquitin binding loops that includes C88. Despite its small size and covalent attachment, RA190 addition to RPN13 led to signal loss (FIGS. 3A and 3B), which suggests that it may adopt multiple configurations when adducted to RPN13. Our structure calculations yielded four major RA190 conformations when adducted to RPN13 C88 Sg (FIGS. 4C and 12A-12C). FIGS. 12A-12F show a series of models and graphs showing detailing the interaction between RA190 and RPN13. 12A-12C show models of the human RPN13 Pru~RA190 interaction. 12D shows a chemical structure of RA190 and RPN13 C88 side chain. 12E shows a model of the RPN13 structure highlighting the amino acids from (12F) that shift after RA190 incubation (T273, L314 and M342) in green and C88 in yellow. 12F shows expanded regions of HSQC spectra recorded on RPN13 (top panels) and after incubation with 10-fold molar excess RA190 (second panels) and of RPN13 (253-407, 'RPN13 CTD', third panels). A merger of the three upper panels is displayed in the bottom panels with RPN13, RPN13 with RA190, and RPN13 (253-407) in black, orange, and blue respectively. In FIG. 4C and FIGS. 12A-12C, amino acids most affected by RA190 are highlighted in darkest red. RA190 carbon, nitrogen, oxygen, and chlorine atoms are colored light blue, indigo, red, and green, respectively. For depiction, we selected the lowest energy structure (FIG. 4C), which was also most consistent with our NMR data (FIGS. 4A and 4B). Rpn13 UCH37-binding domain abuts the Pru domain,[11] and the region targeted by RA190 is within the interdomain contact surface (FIG. 12D). In FIG. 12F, four distance restraints defined between RPN13 C88 Sγ and RA190 CAI, HAI, CAZ, and CBC atoms are highlighted with arrows and were used in the structure calculations. An NMR spectrum from a mixture of RA190-modified and unmodified RPN13 provides evidence that the RPN13 interdomain interactions are abrogated by RA190 (FIG. 12F). FIG. 12F shows expanded regions of HSQC spectra recorded on RPN13 (top panels) and after incubation with 10-fold molar excess RA190 (second panels) and of RPN13 (253-407, 'RPN13 CTD', third panels). A merger of the three upper panels is displayed in the bottom panels with RPN13, RPN13 with RA190, and RPN13 (253-407) in black, orange, and blue respectively.

RA190 Causes Endoplasmic Reticulum Stress

Figure 5A:
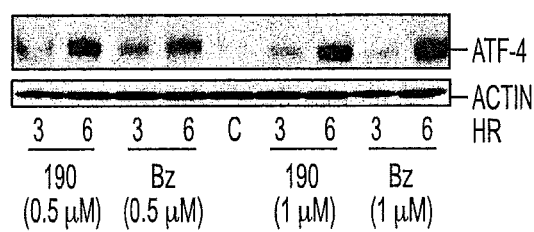
FIG. 5A shows an immunoblot analysis for ATF-4 and actin in MM.1S cells either untreated (C), or treated with RA190 (190) or bortezomib (Bz) for the indicated times.
Figure 5B:
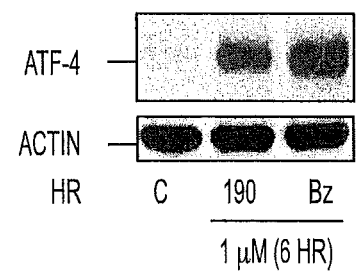
FIG. 5B shows an immunoblot analysis for ATF-4 in HeLa cells either untreated (C), or treated with 1 µM of RA190 (190) or 1 µM bortezomib (Bz) for 6 hr.
Figure 5C:
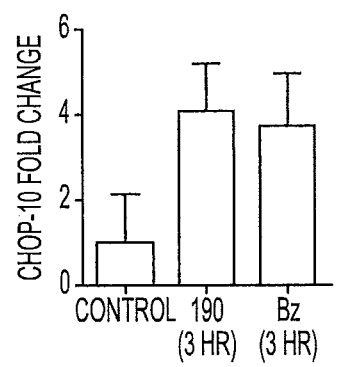
FIG. 5C is a graph showing mRNA levels of CHOP-10 expression.
Figure 5D:
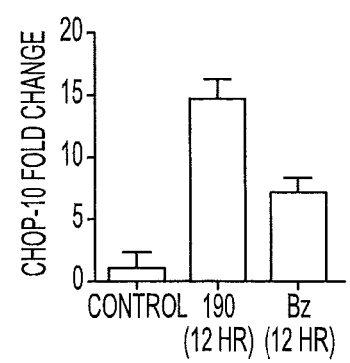
FIG. 5D is a graph showing mRNA levels of CHOP-10 expression.
Figure 5E:
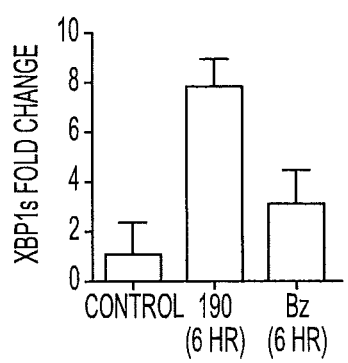
FIG. 5E is a graph showing mRNA levels of XBP1 expression.
Figure 5F:
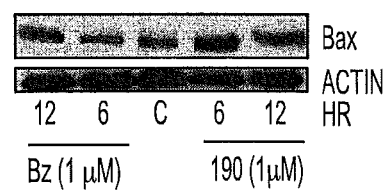
FIG. 5F is an immunoblot analysis showing Bax protein levels in MM.1S cells treated as in FIG. 5A.
Figure 13A:
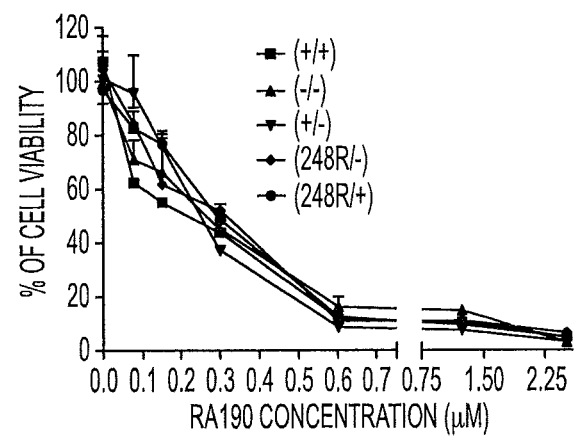
FIG. 13A shows the viability of cells with two, one or no alleles of TP53 or with mutations to TP53 following treatment with varying concentrations of RA190.
Figure 13B:
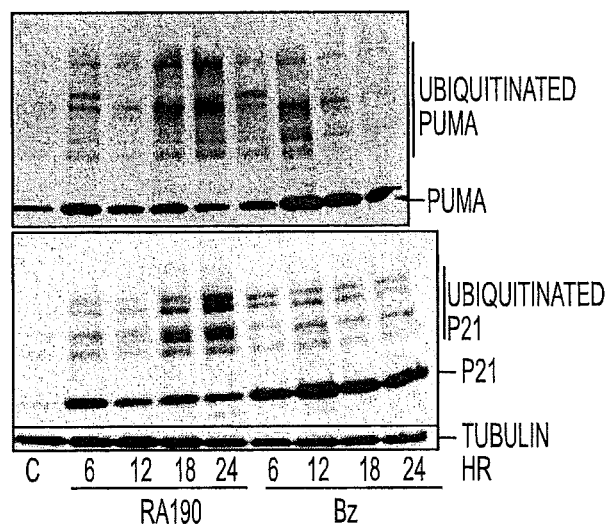
FIG. 13B shows a western blot analysis of lysates from HeLa cells treated with RA190 or bortezomib. Blots were stained with antibodies against p21 and Puma.

The accumulation of unfolded proteins in the endoplasmic reticulum triggers the UPR, which attempts to restore homeostasis by translation attenuation and upregulation of chaperones. However when the UPR fails to restore homeostasis, it promotes apoptosis. Proteasome inhibition creates endoplasmic reticulum stress by blocking the removal of misfolded proteins, enhancing IRE1a-mediated splicing of the mRNA coding for active transcription factor XBP1, one of the main UPR branches, and elevating expression of activating transcription factor-4 (ATF-4) and C/EBP-homologous protein (CHOP)-10, both transcription factors driving apoptosis. Treatment of MM.1S and HeLa cells with RA190 caused upregulation of ATF-4 protein levels and CHOP-10 and XBP1s mRNA levels prior to apoptosis (FIGS. 5A-5E). FIGS. 5A-5H show a series of immunoblot assays showing that RA190 u[regulates UPR and targets of HPV E6. 5A shows an immunoblot analysis for ATF-4 and actin in MM.1S cells either untreated (C), or treated with RA190 (190) or bortezomib (Bz) for the indicated times. 5B shows an immunoblot analysis for ATF-4 in HeLa cells either untreated (C), or treated with 1 μM of RA190 (190)

or 1 µM bortezomib (Bz) for 6 hr. 5C and 5D show mRNA levels of CHOP-10 expression in ATF-4 HeLa cells as a function of a 3 hr (5C) or 12 hr (5D) treatment with RA190 or bortezomib. 5E shows mRNA levels of XBP1 expression in ATF-4 HeLa cells as a function of treatment with RA190 or bortezomib. 5F shows an immunoblot analysis for Bax protein levels in MM.1S cells treated as in 5A. 5G shows immunoblot analysis for p53 and β-tubulin in the indicated cell line either untreated (C) or treated with 1 µM RA190 (190) or Bortezomib (Bz) for 24 hr (top panel) or for the indicated times (bottom panel). 5H shows immunoblot assays for p21, Puma, Bax, Bak, and hDLG-1 at the time points indicated. Specifically, FIG. 5A shows an immunoblot analysis for ATF-4 and actin in MM.1S cells either untreated (C), or treated with RA190 (190) or bortezomib (Bz) for the indicated times. FIG. 5B shows an immunoblot analysis for ATF-4 in HeLa cells either untreated (C), or treated with 1 µM of RA190 (190) or 1 µM bortezomib (Bz) for 6 hr. FIGS. 5C and 5D show mRNA levels of CHOP-10 expression in ATF-4 HeLa cells as a function of a 3 hr (5C) or 12 hr (5D) treatment with RA190 or bortezomib. FIG. 5E shows mRNA levels of XBP1 expression in ATF-4 HeLa cells as a function of treatment with RA190 or bortezomib. Bax is a critical element in the induction of apoptosis by UPR, and RA190 treatment of MM.1S cells significantly elevated Bax protein levels (FIG. 5F). Conversely, UPR induced cell death is typically p53-independent. Isogenic HCT116 cells in which both alleles of wild-type TP53 had been eliminated by homologous recombination, or HCT-116 cells into which mutant p53 was introduced, exhibited similar sensitivity to bortezomib and RA190 as the parental line (FIG. 13A), consistent with p53-independent cell death in response to an unresolved UPR. In FIG. 13A, HCT116 cells containing two WT TP53 alleles (+/+), one WT TP53 allele (+/−), or neither (−/−), or a mutant TP53 248R allele with one (248R1+) or no WT TP53 allele (248R1-) were cultured for 48 hr in the presence of the concentrations of RA190 indicated and their mean viability±SD was determined. FIGS. 13A-13B show a graph and immunoblot showing cell viability as a function of the presence, absence or mutations of TP53 and the effect of indicated compounds on cellular activities, respectively. 13A shows the viability of cells with two, one or no alleles of TP53 or with mutations to TP53 following treatment with varying concentrations of RA190. 13B shows a western blot analysis of lysates from HeLa cells treated with RA190 or bortezomib. Blots were stained with antibodies against p21 and Puma.

RA190 Elevates p53 and p53-Regulated Genes in Cervical Cancer Cells

Figure 5G:
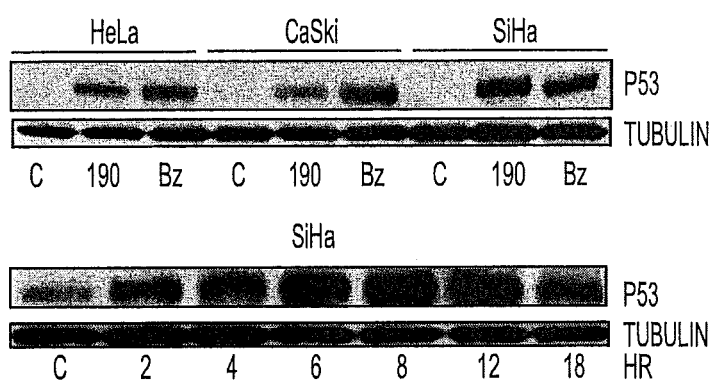
FIG. 5G is an immunoblot analysis for p53 and β-tubulin in the indicated cell line either untreated (C) or treated with 1 µM RA190 (190) or Bortezomib (Bz) for 24 hr (top panel) or for the indicated times (bottom panel)
Figure 5H:
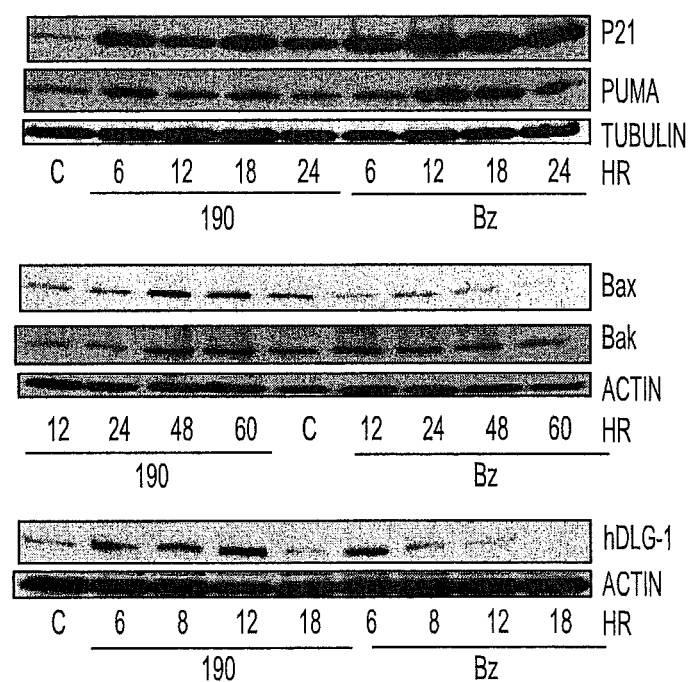
FIG. 5H is an immunoblot assays for p21, Puma, Bax, Bak, and hDLG-1 at the time points indicated.
Figure 6A:
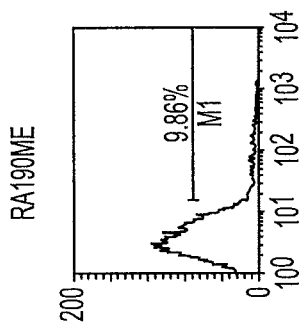
FIG. 6A is a graph showing Annexin-V expression in untreated cells.
Figure 6B:
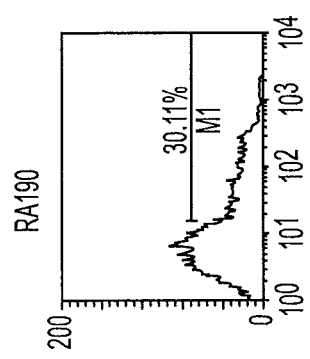
FIG. 6B is a graph showing Annexin-V expression in cells treated with RA190.
Figure 6C:
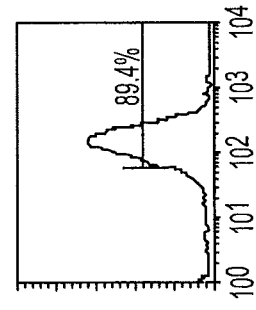
FIG. 6C is a graph showing Annexin-V expression in cells treated with RA190ME.
Figure 6D:
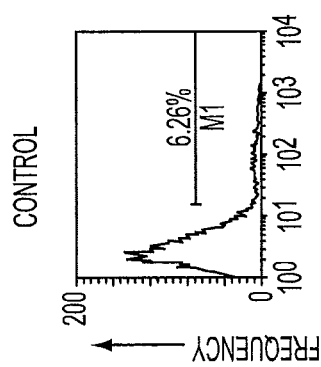
FIG. 6D is a graph showing Annexin-V expression in cells treated with Bz.
Figure 6E:
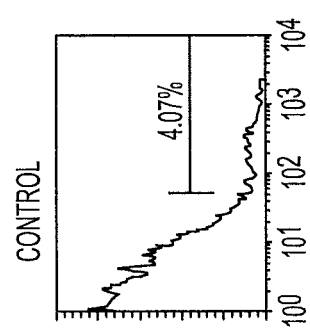
FIG. 6E is a graph showing Annexin-V expression in untreated cells.
Figure 6F:
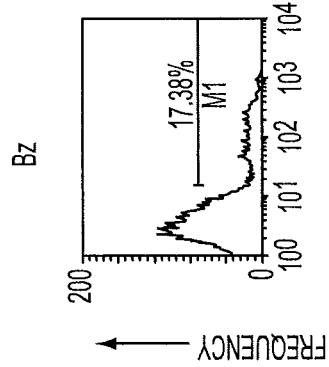
FIG. 6F is a graph showing Annexin-V expression in cells treated with RA190.

HPV E6-mediated degradation of p53 and other targets via the proteasome is a hallmark of high-risk HPV types and critical to transformation,[10,31] suggesting that stabilization of E6 targets and consequent pro-apoptotic signaling may account for the greater sensitivity of HPV-transformed cells to RA190. However, combination of RA190 and bortezomib was synergistic (CI=0.4) for killing of HeLa cells in vitro, suggesting distinct targets (FIG. 9A). We therefore investigated whether RA190, like bortezomib, could restore the levels of wild-type p53 in HPV-transformed cervical cancer cells.[23] Treatment of HeLa, CaSki, and SiHa cells for 24 hr with RA190 elevated p53 levels as with bortezomib (FIG. 5G, top panel). Rapid and time-dependent recovery of p53 levels was observed within 2 hr of RA190 treatment, reaching maximal levels by 6 hr (FIG. 5G, bottom panel). p53-targets p21 and Puma,[35] including their ubiquitinated forms, were also increased in a time-dependent manner (FIGS. 5H and 13B). In FIG. 13B, HeLa cells were treated with RA190 (1 µM) or Bortezomib (1 µM) for the indicated time periods and the cell lysate was subjected to Western blot analysis and probed with anti-p21 and anti-Puma antibody. Tubulin was used as a loading control. Treatment of HeLa cells with RA190 or bortezomib increased levels of pro-apoptotic factors targeted by E6 for degradation,[26] notably and Bak (FIG. 5H), and the tumor suppressor hDLG-1 in HeLa (FIG. 5H) and CaSki cells (not shown). Thus RA190 stabilizes multiple E6 targets, [26] including pro-apoptotic and tumor suppressor proteins, through proteasome inhibition.

RA190 Induces Apoptosis and Display of HSP90 on the Surface of Dying Tumor Cells The rapid upregulation of pro-apoptotic factors and loss of viability upon RA190 treatment may reflect apoptosis. Annexin-V flow cytometric measurements made 12 hr after treating MM and HeLa cells indicate that RA190 and bortezomib trigger extensive apoptosis (FIGS. 6A-6D and 6E-6G). FIGS. 6A-G show a series of immunoblots and graphs showing that RA190 triggers apoptosis and cell surface presentation of HSP90. 6A-6D show graphs showing Annexin-V expression in HeLa cells untreated (6A) or treated with RA190 (6B), RA190ME (6C) or bortezomib (6D). 6E-6G show graphs showing Annexin-V expression in MM.1S cells untreated (6E) or treated with RA190 (6F) or bortezomib (6G). 6H shows the amount of active caspase-3 in HeLa as a function of treatment with varying concentrations of RA190 or bortezomib. 6I is a representative flow cytometry analysis of MM.1S cells treated as in (6E-6G) and stained for active caspase-3. 6J is an immunoblot of lysates from HeLa cells either untreated (C) or treated with 1 µM RA190 (190) or bortezomib (Bz). 6K is an immunoblot of lysates from MM1.S cells either untreated (C) or treated with 0.5 µM RA190 or bortezomib for 6 hr. 6L is a graph showing expression of surface HSP90 on HeLa cells treated with 1 mM RA190, bortezomib, or cisplatin as a function of time. Activation of ICE family members such as caspase-3 and -7 results in cleavage of poly ADP ribose polymerase (PARP) to 85 kDa and 25 kDa fragments and drives apoptosis. The ability of RA190 to trigger caspase-3 activity (FIGS. 6H and 6I) and PARP cleavage (FIGS. 6J and 6K) in MM lines and cervical cancer is consistent with induction of apoptotic cell death.

Bortezomib treatment of MM cells elevates expression and surface exposure of HSP90 in association with "immunogenic" cell death.[33] HeLa and CasKi cells were treated with RA190 or bortezomib and cell surface HSP90 detected by flow cytometry. RA190 treatment of HeLa cells for 24 hr produced cell-surface HSP90 on 54.2% of cells, whereas 12.8% of bortezomib-treated cells and only 3% of control cells displayed HSP90, demonstrating that this phenomenon is not restricted to MM cells. Notably, cisplatin did not induce surface display of HSP90, suggesting that not all types of killing affect cells in this way (FIG. 6L). A time course experiment in HeLa cells demonstrated initiation of surface HSP90 by 6 hr and strong upregulation by 12 hr following RA190 treatment (FIG. 6L), indicating a similar time course to Annexin V-staining (not shown), and more rapid onset than that for bortezomib treatment.

Pharmacokinetics and Safety of RA190

Figure 14:
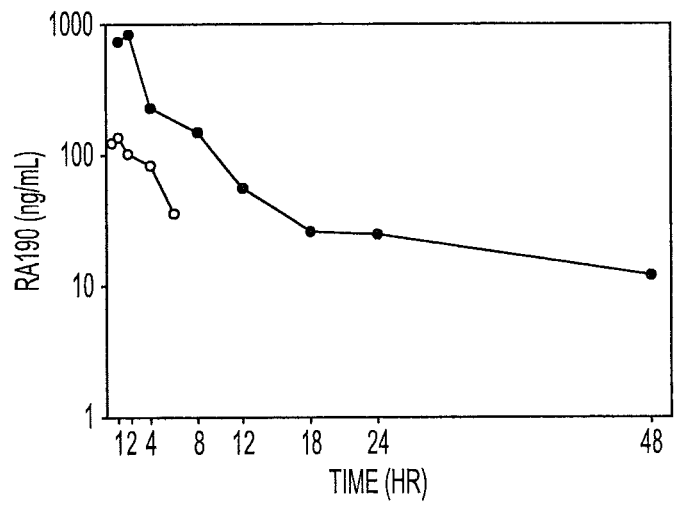
FIG. 14 shows a graph showing the pharmacokinetics of RA190 given to mice i.p. or orally.

Upon formulation in 20% (w/v) β-hydroxyisopropyl-cyclodextrin in water, mice were treated with various single oral (p.o.) and intraperitoneal (i.p.) doses of RA190. With i.p. administration of 10 mg/kg RA190, peak plasma levels (Cmax) were observed in 2 hr, and then declined multi-exponentially with distribution ($T_{1/2, \alpha}$) and terminal ($T_{1/2, \beta}$) half-lives of 4.2 and 25.5 hr, respectively (FIG. 14). After p.o. administration of 20 mg/kg, RA190 plasma concentrations rose rapidly during the first hour and then declined exponentially with a T112, R of 2.6 hr. Based on the RA190 AUC values, the bioavailability of RA190 delivered p.o. relative to i.p. was 7.2%. RA190 was detected in kidney (0.61 µg/g), liver (0.57 µg/g), lung (0.66 µg/g), and spleen (0.59 µg/g), but not brain 48 hr after the mice were given a single i.p. dose of 10 mg/kg RA190. More specifically, FIG. 14 shows mean RA190 plasma concentration versus time curves from non-tumor bearing mice (BALB/c mice, 4-6 weeks old) treated with 10 mg/kg intraperitoneally (•) or 20 mg/kg orally (○). The non-compartmental pharmacokinetic analysis identified the following parameters; for the 10 mg/kg i.p dose, a Cmax of 808 ng/mL, an AUC of 4393 ng*hr/mL, $T_{1/2},\alpha^b$ of 4.2 hr, a $T_{1/2}\beta^b$ of 25.5 hr, a Ud/F of 83.61 L/kg, a Cl/F of 2.3 L/hr/kg; for the 20 mg/kg oral dose, a Cmax of 133 ng/mL, an AUC of 634 ng*hr/mL, an $F_a$ of 7.2%, a $T_{1/2}\beta b$ of 2.6 hr, a Ud/F of 117.3 L/kg, and a Cl/F of 31.6 L/hr/kg.

To examine its safety/toxicity profile, mice were given three doses of 40 mg/kg RA190 p.o. or vehicle alone every third day and euthanized on day 12. Blood was harvested and blood chemistry and hematologic analyses performed (Table 2). No significant difference between the panels of tests was observed between the vehicle and RA190-treated groups, except for a small reduction in triglycerides. The histopathology of the lungs, kidney, spleen, and liver was unremarkable in both the vehicle and RA190-treated animals. Similar studies performed in mice bearing TC-1 tumors and treated with either RA190 or bortezomib also suggest that RA190 has a promising safety profile (Table 3).

TABLE 2

Complete blood counts and blood chemistry of healthy Balb/C mice treated with 3 doses of RA190 (40 mg/kg p.o. every third day) for a period of 9 days.

| Complete Blood Counts | Vehicle (mean ± SD, n = 3) | RA190 (mean ± SD, n = 3) | Normal Range |
|---|---|---|---|
| Leukocytes | | | |
| WBC(White Blood Cells) | 9.03 ± 3.85 | 7.88 ± 3.42 | 1.8-10.7 |
| NE(Neutrophils) | 2.37 ± 1.47 | 2.43 ± 0.94 | 0.1-2.4 |
| LY(Lymphocytes) | 5.92 ± 1.91 | 4.78 ± 1.89 | 0.9-9.3 |
| MO(Monocytes) | 0.42 ± 0.20 | 0.34 ± 0.28 | 0.0-0.4 |
| EO (Eosinophils) | 0.24 ± 0.22 | 0.24 ± 0.23 | 0.0-0.2 |
| BA(Basophils) | 0.07 ± 0.04 | 0.06 ± 0.07 | 0.0-0.2 |
| Erythrocytes | | | |
| RBC (red Blood Cells) | 10.53 ± 0.46 | 10.38 ± 0.26 | 6.36-9.42 |
| Hb (Hemoglobin) | 15.26 ± 0.35 | 14.63 ± 0.15 | 11.0-15.1 |
| HCT (Hematocrit) | 58.30 ± 1.83 | 55.66 ± 1.70 | 35.1-45.4 |
| MCV (Mean corpuscular Volume) | 55.36 ± 0.72 | 53.60 ± 0.26 | 45.4-60.3 |
| MCH (Mean corpuscular hemoglobin) | 14.50 ± 0.4 | 14.10 ± 0.2 | 14.1-19.3 |
| MCHC (mean corpuscular hemoglobin concentration) | 26.20 ± 0.43 | 26.33 ± 0.55 | 30.2-34.2 |
| RDW (Red Blood Cell Distribution Width) | 17.40 ± 0.55 | 17.23 ± 0.30 | 12.4-27.0 |
| Thrombocytes | | | |
| PLT (Platelet) | 605.33 ± 81.64 | 533 ± 61.65 | 592-2972 |
| MPV (Mean Platelet Volume) | 5.13 ± 0.25 | 5.06 ± 0.37 | 5.0-20.0 |
| Blood Chemistry Panel | | | |
| CHOL (Cholesterol) | 121.33 ± 13.01 | 114 ± 12.12 | 60-165 |
| TRIG (Triglycerides) | 156.33 ± 14.74 | 107.33 ± 22.40 | 109-172 |
| UA (Uric Acid) | 1.466 ± 0.11 | 1.5 ± 0.26 | |
| CK_NEW (Creatinine Kinase) | 89.66 ± 36.6 | 55.66 ± 25.48 | |
| GGTNEW (Gamma-Glutamyl Transferase) | 3.66 ± 0.57 | 4.33 ± 0.57 | |
| ALTNEW (Alanine Aminotransferase) | 35.33 ± 2.08 | 39.66 ± 4.04 | 20-80 |
| ASTNEW (Aspartate aminotransferase) | 51 ± 3.0 | 62.66 ± 11.01 | 50-300 |
| AMYL (Amylase) | 890.66 ± 59.1 | 743 ± 29.4 | 1063-1400 |
| ALPNEW (Alkaline Phosphatase) | 82.66 ± 10.69 | 84.33 ± 7.57 | 28-96 |
| TBIL1 (Total bilirubin) | 0.26 ± 0.05 | 0.26 ± 0.05 | 0.1-0.9 |
| GLU (Glucose) | 175.66 ± 4.04 | 175.33 ± 20.5 | 62-175 |
| TPROT (Total protein) | 5.2 ± 0.26 | 5.16 ± 0.05 | 3.5-7.2 |
| CA (Calcium) | 8.96 ± 0.23 | 9 ± 0.2 | 9.0-13.0 |
| BUNNEW (Blood Urea Nitrogen) | 18.66 ± 1.52 | 20 ± 2.64 | 17-31 |
| CREAT (Creatinine) | 0.33 ± 0.05 | 0.36 ± 0.05 | 0.3-1.0 |
| ALBNEW (Albumin) | 3.06 ± 0.15 | 3.03 ± 0.05 | 2.5-4.8 |
| HDLNEW (High Density Lipoprotein) | 51 ± 4.0 | 49 ± 5.29 | 45-96 |
| LDH (lactate Dehydrogenase) | 164.66 ± 18.5 | 160 ± 37.51 | |
| Na (Sodium) | 148.5 ± 2.12 | 147.5 ± 0.70 | |
| K (Potassium) | 6.1 ± 0.14 | 6.05 ± 0.21 | |

TABLE 3

Complete blood counts and blood chemistry of C57BL/6 black mice carrying TC-1 tumor treated with nine doses of RA190 (40 mg/kg p.o. every third day) and Bortezomib (1.5 mg/kg i.p. every third day).

| CBC (Complete Blood Counts) | Vehicle (mean ± SD, n = 3) | RA190 (mean ± SD, n = 3) | Bortezomib (mean ± SD, n = 3) | Normal Range |
|---|---|---|---|---|
| Leukocytes | | | | |
| WBC(White Blood Cells) | 13.56 ± 4.21 | 7.62 ± 4.17 | 24.85 ± 23.94 | 1.8-10.7 |
| NE(Neutrophils) | 9.72 ± 5.42 | 2.69 ± 0.45 | 24.06 ± 15.07 | 0.1-2.4 |

TABLE 3-continued

Complete blood counts and blood chemistry of C57BL/6 black mice carrying TC-1 tumor treated with nine doses of RA190 (40 mg/kg p.o. every third day) and Bortezomib (1.5 mg/kg i.p. every third day).

| CBC (Complete Blood Counts) | Vehicle (mean ± SD, n = 3) | RA190 (mean ± SD, n = 3) | Bortezomib (mean ± SD, n = 3) | Normal Range |
|---|---|---|---|---|
| LY(Lymphocytes) | 3.14 ± 1.34 | 1.87 ± 0.69 | 2.12 ± 1.83 | 0.9-9.3 |
| MO(Monocytes) | 0.38 ± 0.09 | 0.25 ± 0.07 | 0.20 ± 0.13 | 0.0-0.4 |
| EO (Eosinophils) | 0.27 ± 0.15 | 0.10 ± 0.01 | 0.64 ± 0.48 | 0.0-0.2 |
| BA(Basophils) | 0.04 ± 0.00 | 0.023 ± 0.011 | 0.07 ± 0.06 | 0.0-0.2 |
| Erythrocytes | | | | |
| RBC (red Blood Cells) | 8.84 ± 0.24 | 9.77 ± 0.76 | 7.63 ± 1.01 | 6.36-9.42 |
| Hb (Hemoglobin) | 12.56 ± 0.68 | 13.26 ± 1.00 | 11.3 ± 0.70 | 11.0-15.1 |
| HCT(Hematocrit) | 45.46 ± 0.55 | 50.36 ± 2.45 | 42.36 ± 4.15 | 35.1-45.4 |
| MCV (Mean corpuscular Volume) | 51.40 ± 0.81 | 51.66 ± 2.63 | 55.66 ± 1.72 | 45.4-60.3 |
| MCH (Mean corpuscular hemoglobin) | 14.23 ± 0.90 | 13.60 ± 0.53 | 14.90 ± 1.05 | 14.1-19.3 |
| MCHC (mean corpuscular hemoglobin concentration) | 27.63 ± 1.65 | 26.33 ± 0.75 | 26.73 ± 1.16 | 30.2-34.2 |
| RDW (Red Blood Cell Distribution Width) | 18.63 ± 1.12 | 18.00 ± 0.52 | 20.13 ± 0.61 | 12.4-27.0 |
| Thrombocytes | | | | |
| PLT (Platelet) | 886.33 ± 128.0 | 907 ± 45.92 | 1346 ± 87.5 | 592-2972 |
| MPV (Mean Platelet Volume) | 5.50 ± 0.2 | 5.36 ± 0.06 | 5.40 ± 0.10 | 5.0-20.0 |
| Blood Chemistry Panel | | | | |
| CHOL (Cholesterol) | 77 ± 11.31 | 67 ± 4.58 | 69 ± 7.93 | 60-165 |
| TRIG (Triglycerides) | 54 ± 4.24 | 61.33 ± 1.15 | 56.66 ± 15.88 | 109-172 |
| UA (Uric Acid) | 2.25 ± 0.21 | 2.86 ± 0.41 | 2.73 ± 0.87 | |
| CK_NEW (Creatinine Kinase) | 110 ± 24.04 | 131 ± 65.50 | 93.66 ± 3.52 | |
| GGTNEW (Gamma-Glutamyl Transferase) | 5.5 ± 0.70 | 5.33 ± 0.57 | 5.00 ± 0.67 | |
| ALTNEW (Alanine Aminotransferase) | 27.5 ± 0.7 | 31.33 ± 2.30 | 26.33 ± 2.51 | 20-80 |
| ASTNEW (Aspartate aminotransferase) | 47 ± 5.66 | 50.33 ± 4.93 | 53 ± 18.52 | 50-300 |
| AMYL (Amylase) | 417 ± 74.95 | 621.33 ± 127 | 473 ± 57.86 | 1063-1400 |
| ALPNEW (Alkaline Phosphatase) | 34.50 ± 10.60 | 55.33 ± 6.50 | 49 ± 5.29 | 28-96 |
| TBIL1 (Total bilirubin) | 0.2 ± 0.0 | 0.233 ± 0.057 | 0.26 ± 0.05 | 0.1-0.9 |
| GLU (Glucose) | 154.50 ± 28.99 | 170.66 ± 6.11 | 128 ± 20.29 | 62-175 |
| TPROT (Total protein) | 4.25 ± 0.07 | 4.46 ± 0.11 | 4.40 ± 0.26 | 3.5-7.2 |
| CA (Calcium) | 8.60 ± 0.28 | 8.56 ± 0.23 | 8.83 ± 0.60 | 9.0-13.0 |
| BUNNEW (Blood Urea Nitrogen) | 19.0 ± 4.24 | 26 ± 5.29 | 22.66 ± 5.13 | 17-31 |
| CREAT (Creatinine) | 0.25 ± 0.07 | 0.46 ± 0.057 | 0.33 ± 0.05 | 0.3-1.0 |
| ALBNEW (Albumin) | 2.35 ± 0.07 | 2.76 ± 0.23 | 2.50 ± 0.10 | 2.5-4.8 |
| HDLNEW (High Density Lipoprotein) | 31.5 ± 3.53 | 40.33 ± 4.72 | 28.33 ± 4.61 | 45-96 |
| LDH (lactate Dehydrogenase) | 215 ± 63.63 | 172.06 ± 14.29 | 245.33 ± 96 | |

Proteasome Inhibition In Vivo by RA190

Naked 4UbFL reporter plasmid DNA was delivered either by gene gun into the skin or in vivo electroporation in muscle (FIG. 7), and the level of luciferase in the mouse was assessed before and after drug treatment by bioluminescence imaging. FIGS. 7A-7E show a series of graphs showing inhibition of protease function in mice following treatment with RA190 as seen by an increase in the amount of 4UbFL. In 7A, mice received 4UbFL DNA via electroporation and were orally administered RA190 and bortezomib. In 7B, mice received 4UbFL DNA intradermally and were administered RA190 and bortezomib by i.p. In 7C, mice received 4UbFL DNA via electroporation and were orally administered RA190. In 7D, mice received 4UbFL intradermally and were orally administered RA190. In 7E, mice received 4UbFL DNA intradermally and were RA190 was topically administered. To examine whether RA190 was able to inhibit proteasome function in vivo, mice (ten per group) were injected i.p. with RA190 (40 mg/kg), bortezomib (1.5 mg/kg), or vehicle 1 day after intramuscular (i.m.) electroporation with 4UbFL reporter plasmid (FIG. 7A). At 4 hr after treatment, mice treated with RA190 exhibited 4-fold higher levels of bioluminescence compared to vehicle alone, whereas bortezomib elevated it only 2-fold. One day post-treatment, both RA190 and bortezomib-treated animals exhibited a similar 4-fold increase in bioluminescence, suggesting continued inhibition of proteasome function (FIG. 7A). The level of bioluminescence observed in the vehicle-treated mice decreased steadily over 48 hr, suggesting a slow loss of transfected cells. At 48 hr after RA190 treatment, the mice still showed a significant increase in bioluminescence despite the short half-life of RA190 in blood (FIG. 7A), possibly reflecting slow regeneration of new proteasomes or the continued presence of RA190 or active metabolites in tissues. Because papillomavirus infections are typically restricted to skin and mucosa, the 4UbFL reporter plasmid was delivered into the skin by gene gun.[8,34] Similar stabilization of the 4UbFL reporter was observed, albeit of shorter duration, suggesting that both RA190 and bortezomib were also active in skin (FIG. 7B).

Oral administration of RA190 increased the bioluminescence produced by mice transduced with 4UbFL plasmid either i.m. by electroporation (FIG. 7C) or in skin via gene gun (FIG. 7D). Again, the elevation of bioluminescence in skin was of shorter duration than that for the i.m. studies, possibly reflecting a more rapid turnover of skin cells, as compared to transduced muscle cells of electroporated animals. Topical administration of RA190 at 4% in Cremophor-EL also stabilized the 4UbFL reporter in skin (FIG. 7E). In FIGS. 7A-7E, the transduced mice were treated with vehicle, RA190, or bortezomib (ten mice per group) respectively. After the indicated time points of treatment, bioluminescence was measured by injection of luciferin and imaging with an IVIS 200 (fold change±SD, *p<0.05, **p<0.01). RA190 was given i.p. (7A and 7B) or orally (7C and 7D) at 40 mg/kg; bortezomib was given i.p. at 1.5 mg/kg dose (7A and 7B). In FIG. 7E, RA190 was given 4% in Cremophor-EL topically.

RA190 Treatment Inhibits Tumor Growth in Mice

Figure 8F:
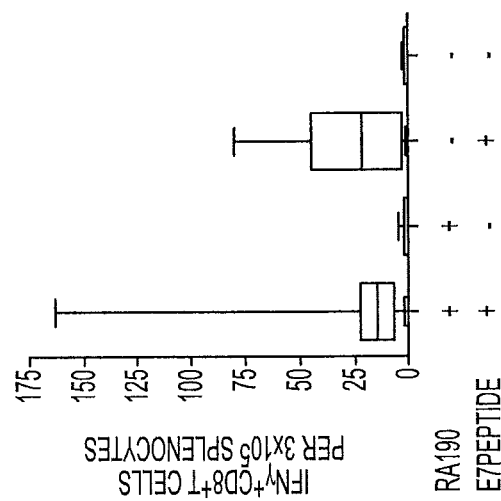
FIG. 8F is a graph showing the mean number±SD of IFNγ$^+$ CD8$^+$ T cells per $3\times10^5$ splenocytes elicited with or without E7 following treatment with RA190.

NOG (NOD/Shi-scid/IL-2Rγnull) mice carrying an NCI-H929 MM line that expresses luciferase received RA190 or vehicle 20 mg/kg/day i.p. daily for 7 days. Prior to and at the end of the treatment, mice were imaged for bioluminescence. RA190 showed potent antitumor activity, even with a 3-day break in the middle of treatment (FIGS. 8A and 8B). FIGS. 8A-D show the effects of RA190 on tumor growth in mice. 8A shows a graph showing inhibition of tumor growth and reduction of tumor size in mice carrying NCI-H929-GFP-luc human tumor cells as a function of treatment with RA190. 8B shows representative bioluminescence images of mice in (8A) before (top panel) and after (bottom panel) treatment. 8C shows a graph showing decrease in bioluminescence of ES2-luciferase tumor cells in mice treated with RA190. 8D shows representative bioluminescence images of mice in (8C) before (upper panel) and after (lower panel) treatment. 8D shows a graph of tumor volume reduction in mice treated with RA190. 8F is a graph showing the mean number±SD of IFNγ+ CD8+ T cells per $3 \times 10^5$ splenocytes elicited with or without E7 following treatment with RA190. The mice were imaged before and at the end of the treatment for bioluminescence levels. We have previously described the susceptibility of human ovarian cancer lines to proteasome inhibition. Nude mice carrying ES2-luciferase tumor i.p. were treated with RA190 or vehicle for 14 days and bioluminescence was imaged weekly. Treatment with RA190 significantly inhibited the ES2 tumor growth (FIGS. 8C and 8D). Specifically, FIG. 8C shows percentage change of bioluminescence±SD in nude mice bearing ES2-luciferase tumor cells (tumor cells injected i.p.) receiving 10 mg/kg RA190 (i.p.) or vehicle alone (n=8) every day. Prior to and 7 and 14 days after initiation of treatment, the mice were imaged for luciferase activity.

Figure 8E:
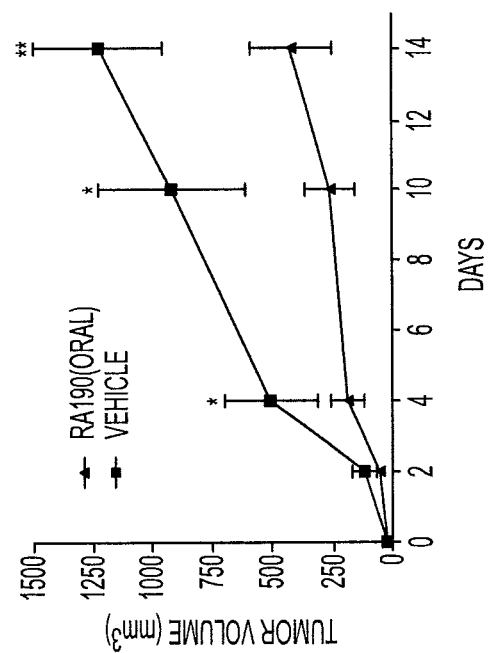
FIG. 8E is a graph showing TC-1 tumor growth in mice treated with RA190 as compared to treatment with vehicle alone.
Figure 15A:
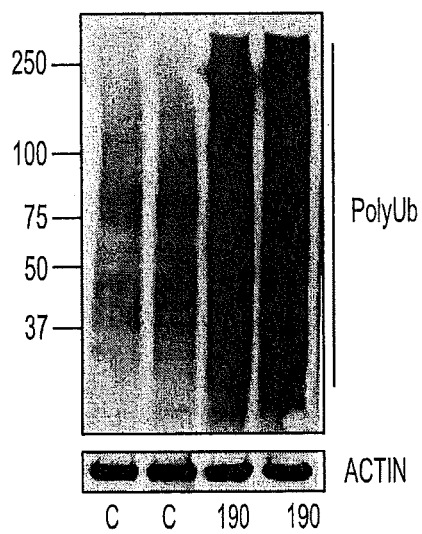
FIG. 15A shows a western blot showing levels of poly-ubiquitinated proteins in lysates of tumor cells from mice treated with RA190.
Figure 15B:
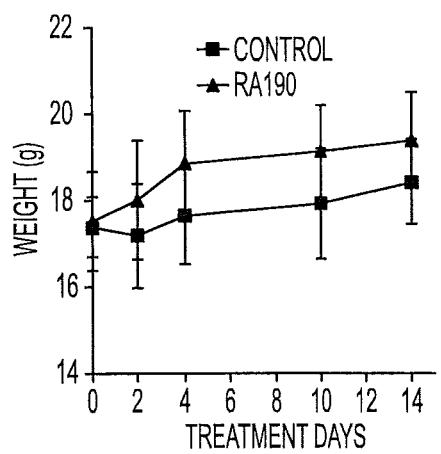
FIG. 15B shows a graph showing the weight of mice as function of treatment with RA190.
Figure 16A:
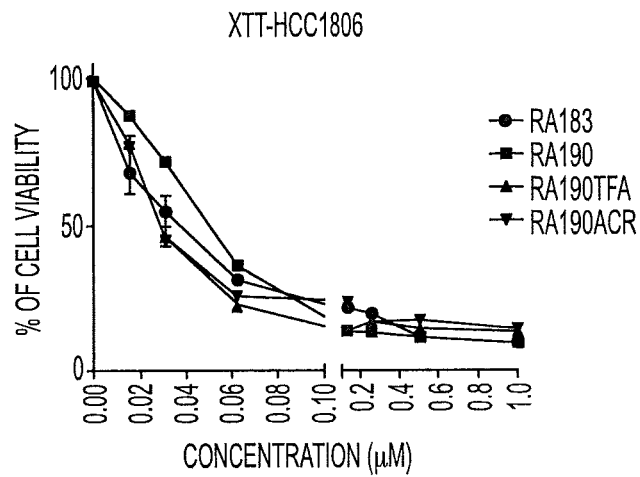
FIG. 16A shows the efficacy of select compounds against HC1806 breast cancer cells.
Figure 16B:
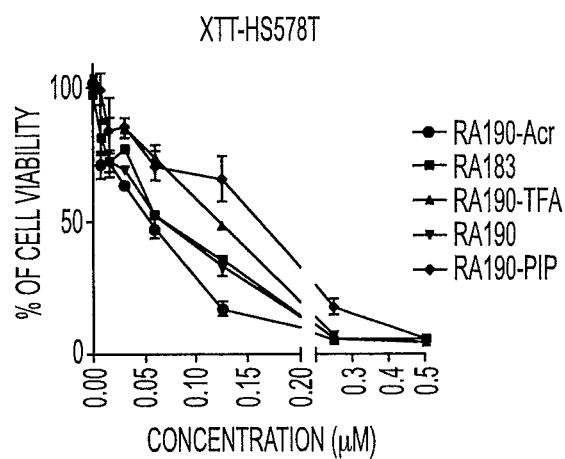
FIG. 16B shows the efficacy of select compounds against HS578T breast cancer cells.
Figure 16C:
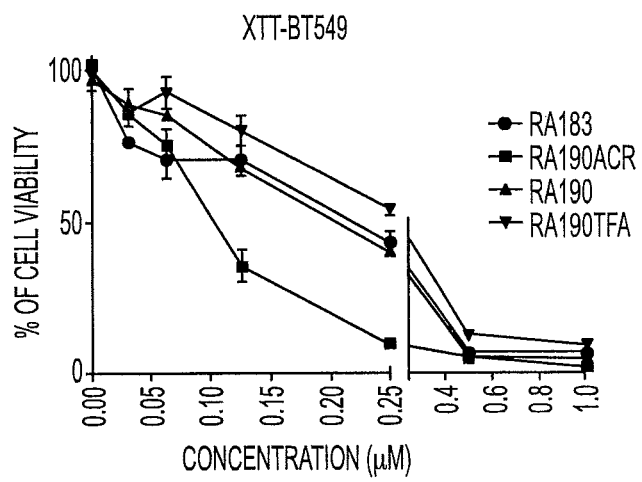
FIG. 16C shows the efficacy of select compounds against BT549 breast cancer cells.
Figure 16D:
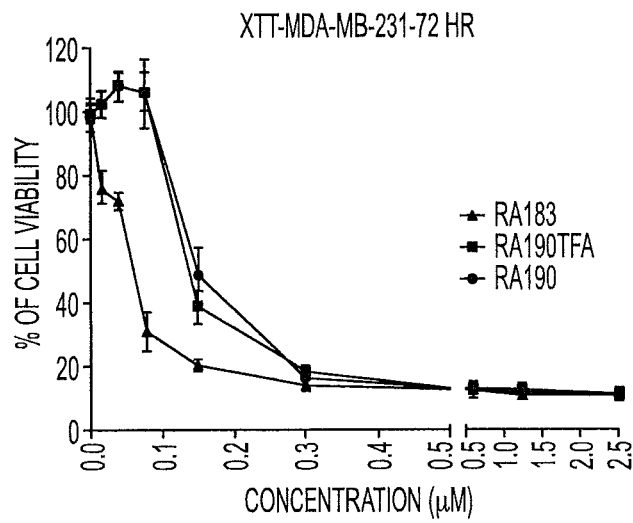
FIG. 16D shows the efficacy of select compounds against MB-231 breast cancer cells.
Figure 16E:
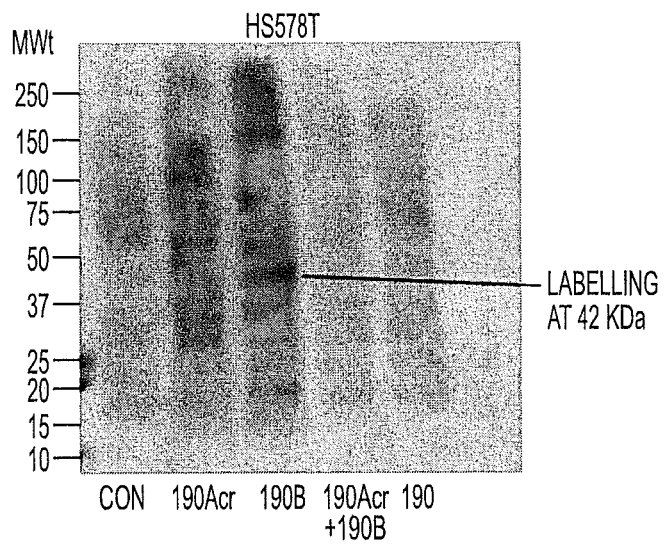
FIG. 16E shows streptavidin peroxidase-probed blot in which RA190Acr competes the binding of RA190B to RPN13 in Triple Negative Breast Cancer (HS578T) cell lysate.

C57BL6 mice carrying HPV16 E6 and E7-transformed and syngeneic tumor TC-1, which spontaneously induces E7-specific CD8+ T cell responses, were treated with either RA190 (i.p., 20 mg/kg) or vehicle daily for 7 days and the tumors were harvested. Tumor lysates probed by western blot for polyubiquitinated proteins were dramatically elevated in the RA190 treatment group, suggesting RA190 can access solid tumor to block proteasome function (FIG. 15A). Oral administration to tumor-bearing mice of RA190 (40 mg/kg every third day) significantly inhibited (p<0.001) TC-1 tumor growth as compared to treatment with vehicle alone (FIG. 8E). The final tumor weights after the 14-day treatment period were 1,873±180 mg in vehicle treated mice and 727±101 mg in the RA190-treated mice (p<0.001). Weight gain and the spontaneous E7-specific CD8+ T cell response did not differ significantly between the vehicle and RA190-treated mice (FIG. 8F; FIG. 15B). FIGS. 15A-15B show an immunoblot and data graph showing the effect of RA190 on levels of polyubiquitination in tumor cells and the effect of RA190 on the overall weight of mice, respectively. 15A shows a western blot showing levels of poly-ubiquitinated proteins in lysates of tumor cells from mice treated with RA190. 15B shows a graph showing the weight of mice as function of treatment with RA190.

Compounds Efficacy Against Triple Negative Breast Cancer

To test the efficacy of various RA compound derivatives on the viability of breast cancer cells, breast cancer cell lines were treated in vitro with varying concentrations of selected compounds. As seen in FIGS. 16A-16D, the viability of HCC 1806, HS578T, BT549 and MB-231 breast cancer cells, respectively, was severely compromised following treatment with various concentrations of indicated compounds for 48 hours, suggesting that Ttriple negative breast cancer cell lines are highly sensitive to proteasome inhibition by these compounds. In addition, FIG. 16E also demonstrates that RA190 analog RA190Acr competes the binding of RA190B to RPN13 in HS578T cell lysate, as detected after SDS-PAGE, blotting to a PVDF membrane and probing with streptavidin-peroxidase. FIGS. 16A-16E are a series of data graphs and a western blot showing the efficacy of select compounds against various breast cancer cell lines. 16A shows the efficacy of select compounds against HC1806 breast cancer cells. 16B shows the efficacy of select compounds against HS578T breast cancer cells. 16C shows the efficacy of select compounds against BT549 breast cancer cells. 16D shows the efficacy of select compounds against MB-231 breast cancer cells. 16E shows streptavidin peroxidase-probed blot in which RA190Acr competes the binding of RA190B to RPN13 in Triple Negative Breast Cancer (HS578T) cell lysate. RA190Acr is another analog of RA190 and showed potency similar to RA190. Briefly HS578T cell lysate was incubated with corresponding compounds for the period of 1 hr at 4 C and subjected to Western blot analysis and probed for HRP-Streptavidin. A new band at 42 KDa indicates that Biotinylated compound binds to RPN13 and the band disappears when the cell lysate is pretreated with the same non-biotinylated compound.

Methods

Chemistry:

All reagents and solvents were obtained from Aldrich. Anhydrous solvents were used as received. Reaction progress was monitored with analytical thin-layer chromatography (TLC) plates carried out on 0.25 mm Merck F-254 silica gel glass plates. Visualization was achieved using UV illumination. $^1$H NMR spectra were obtained at 400 MHz on a Bruker Avance spectrometer and are reported in parts per million downfield relative to tetramethysilane (TMS). EI-MS profiles were obtained using a Bruker Esquire 3000 plus. Crude compounds were purified by semi-preparative reversed phase HPLC using a Water Delta Prep 4000 system with a Phenomenex column C18 (30×4 cm, 300 A, 15 µm spherical particle size column).

Construction of RPN13 Expression Plasmid:

The human RPN13 cDNA was obtained from OriGene™ (ARDM1, NM_175563) and subcloned into pET28a(+) vector (Novagen™) at the BamH1 and Xho1 restriction sites after PCR using forward and reverse primers to yield RPN13-pet28a (+) which expresses a recombinant RPN13 with a hexahistidine-tag at both the N and C terminus. RPN13 is a 42 kDa protein however, because of the additional sequences on the pET28a (+) vector, inclusive of the hexahistidine tags at both ends, the overall molecular weight of recombinant tagged RPN13 was ~49 kDa.

Recombinant RPN13 Preparation:

Human RPN13 full length, RPN13 (1-150), RPN13 (253-407), and His-tagged UCH37 were prepared as described.[31]

Bacterial Strains and Expression of RPN13:

For protein expression, briefly, RPN13-pET28a (+) was transformed into *E. coli* 2 (DE3) cells (Rosetta 2 Cells, Novagen™). Single colonies of transformed cells were picked, suspended into 10 mL of Superbroth and grown aerobically at 250 rpm, 37° C. overnight in 15 mL round bottom tubes (BD Falcon). The next day, 1 mL of the culture was collected and suspended in a new 15 mL round-bottom tube containing 5 mL of fresh Superbroth. The culture was then grown again aerobically at 250 rpm, 370C and monitored for log phase. When the bacteria reached the middle of log phase (OD600=~0.6), 1 mM of isopropylthio-β-D-galactoside (IPTG) was added to induce RPN13 protein expression. In general, it took 2 hr for O.D600 to reach ~0.6. The culture was induced for 3 hr, and 500 µL of the culture was centrifuged. The cells collected were suspended in 100 µL of PBS and 10 µL of the suspension was then collected and analyzed by Tris-Glycine SDS-PAGE.

Plasmid Overexpression Studies:

RPN13, RPN10 plasmids were obtained from Origene™. UCH37 (plasmid 19415) and RAD23/HHR23B (plasmid 13054) plasmids were obtained from Addgene. pCMV-FL plasmid was a kind gift from Dr. David Piwnica Worms. 293TT cells were transfected with the above plasmids with TransIT-2020 transfection reagent for 48 hr per the manufacturer's recommendation (Mirus Bio LLC). Cells were lysed with MPER lysis buffer and subjected to Western blot analysis for biotin recognition studies as described in the biotin labeling assay section.

Cell Culture:

All cell lines were obtained from American Type Culture Collection (Manassas, Va.) except 293TT cells from Dr. C. Buck (NCI, NIH), and were cultured in specified medium supplemented with 10% fetal bovine serum, 100 IU/mL penicillin, and 100 µg/mL streptomycin at 5% CO2. 293, 293 TT, HeLa, SiHa, ME180, HT3 and C33A were grown in DMEM, CaSki, ES2, NCI-H929, MM.1S, RPMI-8226, U266, ANBL6 and Bortezomib resistant lines in RPMI-1640, and SKOV3 and HCT116 cell lines in McCoys 5A Medium. 293TT cells were transfected with RPN13, RPN10 (Origene), UCH37, and HHR23B (Addgene) expression vectors using TransIT-2020 transfection reagent per Mirus Bio's instructions.

Cell Viability Assays:

Cell viability was assayed using CellTiter 960 AQueous One Solution Reagent (Promega, Madison, Wis.). Cells seeded at the concentration of 1,000 cells/well for HeLa, 5,000 cells/well for ES2 and HCT116 and 10,000-20,000 cells/well for other cell lines in 100 µL medium in 96-well plate were treated with RA series compounds at specified concentrations. After the indicated periods, cells were incubated according to the manufacturer's protocol with the MTS labeling mixture for 1-2 hr and absorbance at 490 nm measured using a Benchmark Plus microplate spectrophotometer (BIO-RAD).

Quantitative PCR to Measure mRNA Levels.

Quantitative PCR was performed per the manufacturer's instructions (Applied Biosystems), according to the Livak method and normalized to reference gene GAPDH.s described elsewhere.[3,6] Total RNA was isolated from cells using the RNeasy mini kit (Qiagen). Extracted RNA was normalized for concentration and reverse transcribed using iScript cDNA synthesis kit (Bio-Rad). CHOP-10 expression levels were measured by Taqman gene expression assays with Taqman gene expression master mix (Applied Biosystems) and run with the standard thermal cycling protocol. Spliced XBP1 mRNA was assayed with SsoFast EvaGreen Supermix (Bio-rad) following the protocol for the iCycler System. Calculations were done according to the Livak method and normalized to reference gene GAPDH. Each condition was replicated three times; each sample was run in triplicate.

Flow Cytometry.

An annexin V-PE apoptosis detection kit I (BD PharMingen) was used according to the manufacturer's protocol. Cell surface HSP90 was stained with anti-HSP90 mAb (Stressgen), followed by PE-conjugated anti-mouse IgG1. The data were acquired with a FACSCalibur and analyzed using CellQuest software.

Determination of Apoptotic Cells by Flow Cytometry:

Induction of apoptosis was determined using Annexin V-PE Apoptosis Detection Kit I (BD Pharmingen, San Diego, Calif.) according to the manufacturer's protocol. Briefly, 1×10$^5$ cells were re-suspended in binding buffer, 5 µL of Annexin V-PE and 5 µL of 7-AAD were then added into the cells, which were then incubated at room temperature for 15 min and analyzed by flow cytometry as above.

Antibodies and Western Blot Analysis.

Total cellular protein (10-20 µg) from each sample was subjected to SDS-PAGE, transferred to PVDF membranes and analyzed by Western blot. Antibodies for Western blot analysis were obtained by the following commercial sources: anti-ubiquitin, anti-p53 (FL393), anti-p21(WAF1), anti-hDLG-1(2D11), anti-Puma, Bak, Bax (Cell Signaling Technology, Danvers, Mass.), anti-IκB-α (C-15), anti-ATF-4 (SC-200) (Santa Cruz Biotechnology, Santa Cruz, Calif.), anti-PARP (BD Pharmingen, San Diego, Calif.), anti HSP90 (Stressgen Corp, Victoria BC, Canada), anti-tubulin (Sigma, St. Louis, Mo.), anti-Actin, anti-ADRM1 (anti-RPN13), anti-RPN2 (anti-PSMD1) (Sigma-Aldrich), anti-RPN10, UCH37 (Cell-signaling), anti-RPN1 (proteasome 19S subunit anti-S2) (Thermo Scientific), streptavidin Dyna beads (Invitrogen), HRP-streptavidin (Invitrogen), peroxidase-linked anti-mouse Immunoglobulin G and anti-rabbit IgG (GE Healthcare UK Ltd, UK) and utilized at the concentration recommended by the manufacturer.

Enzymatic Assays.

Reaction mixtures contained 500 nM of the purified 19S RP (R&D Systems) in 19S enzyme assay buffer and 1 µM Ub-AMC. Release of free AMC by the enzyme reaction was determined by measuring its fluorescence at 380 nm (excitation) and 440 nm (emission). The 20S proteolytic activity assays were performed as described elsewhere (Bazzaro et al., 2011).

Biotin Labeling Assay:

Human cells ($5 \times 10^6$ HeLa or 293TT cells) were lysed using MPER (Pierce) lysis buffer (500 µL). RPN13 or HPV L2 transformed bacterial cells (500 µL of culture) were centrifuged to harvest the cells which were re-suspended in 500 µL BPER (Pierce). Cell lysates were centrifuged at 10,000 rpm briefly (2 min) at 4° C. to remove cell debris. Lysate supernatant (200 µL) was pre cleared with streptavidin dyna beads (20 µL) for 1 h at 4° C. to remove non-specific biotin binding and incubated with compounds (indicated concentrations or 20 µM) at 4° C. for 1 hr. An equal amount of each sample (20 µL of lysate) was mixed with an equal volume of Laemmli sample buffer (20 µL) (BioRad) and was boiled for 5 min. The proteins were separated using 4-15% Bio-Rad Mini-PROTEAN SDS-PAGE gel (1 hr at 100 V) and transferred to the membrane overnight at 4° C. (24 V). Membrane was blocked with 5% BSA in PBST for 1 hr at room temperature and washed for 20 min (3×PBST). Then the membrane was probed with HRP-streptavidin (1:10,000 in PBST) for 1 hr at room temperature and washed for 30 min (3×PBST) and developed using HyGLO chemiluminescent detection reagent (Denville) for biotin recognition. For the purified enzyme assay, 19S purified proteasome (R&D Systems, Cat. No. E-366) (500 ng) in 19S buffer (20 mM HEPES, 20 mM NaCl, 1 mM DTT, 15% Glycerol) was incubated with compounds (20 µM) for 1 hr at room temperature and mixed with an equal volume of Laemmli sample buffer (20 µL) (BioRad) and was boiled for 5 min. Each sample was loaded onto gel and followed the western blot protocol mentioned above.

Drug Combination Index Assay:

HeLa cells seeded at 5,000 cells/well in 100 µL medium in 96-well plate were treated with RA190 (0-300 nM) and/or bortezomib (0-30 nM) alone or in combination. After 48 hr, cells were incubated according to the manufacturer's protocol with the MTS labeling mixture (CellTiter 960 AQueous One Solution Reagent, Promega, Madison, Wis.) for 1 hr and absorbance at 490 nm measured using a Benchmark Plus microplate spectrophotometer (BIO-RAD). The combination indices and a normalized isobologram were calculated using Compusyn software (www.combosyn.com).

Cell Surface HSP90 Staining:

Cell surface HSP90 was detected by staining with purified anti-HSP90 mAb (Stressgen), followed by PE-conjugated anti-mouse IgG1. The data were acquired with a FACSCalibur and analyzed using CellQuest software.

Glycerol-Gradient Purification:

293 cells ($20 \times 10^6$) were lysed in MPER lysis buffer (2 mL) using manufacturer recommended protocol (Pierce). Lysate was precleared at 9,000 rpm using table top centrifuge at 4° C. for 2 min. Supernatant were collected and 1 mL of lysate was incubated with RA190 (20 µM) at 4° C. for 1.5 hr and another 1 mL was incubated with DMSO as a control. Both samples were loaded separately on top of a 10-40% (v/v) glycerol gradient (13 mL) and centrifuged at 27,000 rpm for 15 hr at 4° C. in a Beckman SW 40 Ti rotor. Fractions (0.8 mL) were collected from the top of the gradient and analyzed for proteasomal proteins by Western blot analysis.

19S Ub-AMC Assay:

Proteasomes retain high levels of ubiquitin-AMC (Ub-AMC) hydrolyzing activity, which is presumably dependent on 19S RP subunits USP14 and UCH37. To identify whether RA190 has any influence on these enzymes, we performed an in vitro assay with 19S RP. Reaction mixtures contained 500 nM of the purified 19S RP in 19S enzyme assay buffer and 1 µM Ub-AMC. After incubation of the mixtures with corresponding compounds for various concentrations and time periods at 37° C., release of free AMC by the enzyme reaction was determined by measuring its fluorescence at 380 nm (excitation) and 440 nm (emission). The graphs shown are representative of at least two independent determinations and each data point is the mean of ±SD of triplicate determinations.

20S Proteolytic Activity Assay:

Purified 20S proteasomes were treated for 30 min with or without compounds (1 µM) or Bortezomib (1 µM) prior to the addition of the specific fluorogenic substrate for chymotrypsin (Suc-LLVY-AMC), tryptic (Boc-LRR-AMC) or PGPH (Ac-YVAD-AMC) hydrolytic proteasome capacities. Release of free AMC by the enzyme reaction was determined by measuring its fluorescence at 380 nm (excitation) and 440 nm (emission). The graphs shown are representative of at least three independent determinations and each data point is the mean of ±SD of triplicate determinations.

NMR spectroscopy:

NMR spectra were acquired at 25° C. or 10° C. on Bruker NMR spectrometers operating at 850 or 900 MHz and equipped with cryogenically cooled probes. Processing was performed in NMRPipe[13] and the resulting spectra visualized with XEASY.[3] Protein concentrations were calculated by extinction coefficients based on amino acid composition and absorbance at 280 nm for protein dissolved in 6 M guanidine-HCl. Buffer A (20 mM NaPO4, pH 6.5, 50 mM NaCl, 2 mM DTT, 0.1% NaN3, and 5% D20) was used for all NMR samples except those containing RA190, which were performed in Buffer B (Buffer A with no DTT present). 10-fold molar excess RA190 (5 mM stock in DMSO) was incubated with RPN13 protein at 4° C. overnight and unreacted RA190 removed by dialysis.

LC High Resolution Mass Spectrometry:

RPN13 Pru domain and RA190-exposed RPN13, RPN13 Pru domain, RPN13 Pru C60,80,121A, and RPN13 Pru C88A at protein concentrations of 1 µg/µL were treated with formic acid and injected onto a Nano2D-LC HPLC system (Eksigent, Dublin, Calif.) equipped with an Agilent Zorbax 300SB C8 column (3 mm ID, 10 cm length, 3.5 µm particle size). The samples were subjected to 10 min of incubation in 98% H2O:2% CH3CN, a 20 min linear gradient at 10 µL/min flow rate to 75% H2O:25% CH3CN followed by a 12 min linear gradient to 5% H2O:95% CH3CN and then a 2 min hold. Analysis was conducted by positive ionization electrospray with an LTQ-Orbitrap Velos instrument (Thermo Scientific, Waltham, Mass.) and adducts were quantified utilizing the Orbitrap detector with a resolution of 100,000 at a scan range of 400-2000 m/z.

RPN13 Pru~RA190 Complex Calculation:

The RPN13 Pru~RA190 complexes were generated by using HADDOCK 2.1 (High Ambiguity Driven protein-protein DOCKing)[15] in combination with CNS (Brunger et al., 1998). A homology model of RPN13 Pru domain was generated by Schrödinger based on the atomic coordinates of murine RPN13 Pru domain (PDB entry 2R2Y).[34] Four distance restraints were defined between C88 Sγ of RPN13 and four atoms of RA190 to recapitulate the sulfur-carbon bond (FIG. 12D and Table 4); HADDOCK requires two distinct molecules for docking. The ratio of peak intensity values (Δ) were plotted for each RPN13 backbone (FIG. 4A) and side chain (FIG. 4B) amide group according to Equation 1, in which*I* represents peak intensity and 0.588 is a scaling factor derived by setting the randomly coiled N and C terminal ends of RPN13 Pru domain as unaffected by RA190.

$$\Delta = 1 - (0.588 \times I_{RPN13\ Pru\text{-}RA190}/I_{RPN13\ Pru})$$ Equation 1:

TABLE 4

Unambiguous distance restraints used in HADDOCK to define RA190 attachment to RPN13 C88 Sγ.

| RPN 13 Pru | RA190 | Distance (in Angstroms) |
|---|---|---|
| C88Sγ | CAI | 1.829 |
| C88Sγ | HAI | 2.384 |
| C88Sγ | CAZ | 2.854 |
| C88Sγ | CBC | 2.735 |

RPN13 Pru residues with Δ values greater than one standard deviation value above average were defined as "active" and their neighbors as "passive" provided they have >40% accessibility. Ambiguous Interaction Restraints (AIRs) were imposed to restrict hRPN13 Pru active residues to be within 2.0 Å of any RA190 atom (Dominguez et al., 2003). 1000 structures were subjected to rigid-body energy minimization and the 250 lowest energy structures chosen for semi-flexible simulated annealing in torsion angle space followed by refinement in explicit water. During semi-flexible simulated annealing, atoms at the interface were allowed to move, but constrained by the AIRs and unambiguous distance constraints defining the sulfur-carbon bond. After water refinement, the RMSD of RA190 in the resulting 250 structures was 3.81±0.60 Å and these were sorted into four clusters by using a 1.5 Å cut-off criterion. The lowest energy structure of each cluster was energy minimized by Schrödinger after the explicit introduction of a covalent bond between RPN13 C88 Sγ and RA190 reacted carbon.

TABLE 5

Statistics for human RPN13~RA190 structures sorted into four clusters by using a 1.5 Å cut-off criterion.

| Cluster No. | Number of Structures | Haddock Score | RMSD | $E_{inter}$ | $E_{vdw}$ | $E_{elec}$ | BSA |
|---|---|---|---|---|---|---|---|
| 1 | 82 | 61.18 ± 8.21 | 0.85 ± 0.33 | 183.35 ± 16.12 | 69.25 ± 4.30 | −10.82 ± 4.37 | 662.04 ± 36.10 |
| 2 | 30 | 69.43 ± 12.85 | 0.86 ± 0.33 | 192.31 ± 24.71 | 76.97 ± 3.86 | −6.70 ± 4.46 | 540.38 ± 28.91 |
| 3 | 29 | 76.45 ± 7.16 | 0.95 ± 0.31 | 198.22 ± 12.11 | 81.17 ± 2.32 | −3.64 ± 2.73 | 470.19 ± 34.17 |
| 4 | 67 | 81.62 ± 7.34 | 1.07 ± 0.31 | 211.25 ± 14.20 | 80.31 ± 2.20 | −2.35 ± 2.06 | 482.75 ± 30.00 |

$E_{inter}$, intermolecular binding energy; $E_{vdw}$, van der Waals energy; $E_{elec}$, electrostatic energy; BSA, buried surface area; RMSD, root mean square deviation for backbone atoms to the cluster's average structure.

Cell Culture Assay for Luciferase:

Sub-confluent cultures of HeLa cells were transfected with 4UbFL or FL plasmids using Lipofectamine 2000 reagent (Life Technologies, Carlsbad, Calif.). HeLa cells were seeded at 20,000 cells/well in a 96-well plate 48 hr post transfection and incubated with compounds or vehicle (DMSO) at the doses or time indicated for individual experiments. Luciferase activity in cell lysate was determined with a luciferase assay kit (Promega, Madison, Wis.) according to the manufacturer's instructions. Bioluminescence was measured by using a Glomax Multidetection system (Promega, Madison, Wis., USA).

Animal Studies.

All animal experiments were performed in accordance with protocols approved by the Animal Care and Use Committee of Johns Hopkins University. Nude, C57BL/6, Balb/c female mice were purchased from the National Cancer Institute (NCI) and NOG (NOD/Shi-scid/IL-2Rγnull) mice were bred in-house. DNA delivery was via a helium-driven gun (Bio-Rad) as described previously[40] or electroporation (ElectroSquarePorator 833, BTX-2 Needle array 5 mm gap, Harvard apparatus) delivered as eight pulses at 106 V for 20 ms with 200 ms intervals. Bioluminescence images were acquired for 10 min with a Xenogen IVIS 200.[25] C57BL/6 mice were challenged subcutaneously with 5×10$^4$ TC-1 cells/mice and E7-specific CD8+ T cell response and tumor size were measured as described previously (Trimble et al., 2003). Nude mice were inoculated with 1×10$^6$ EΩ-luciferase cells i.p. in 100 μl PBS. At day 3, mice were imaged for basal level luciferase activity. NOG mice (five per group) were inoculated with 1×10$^6$ NCI-H929-GFP-luc cells i.v., and imaged for basal luciferase activity after 4 weeks.

Pharmacokinetic Measurements:

Mice were humanely euthanized, and plasma was harvested as a function of time after administration of RA190. Tissue was harvested at 48 hr after single-dose intraperitoneal administration in non-tumor bearing mice. Blood was collected by cardiac puncture under anesthesia into heparinized syringes and centrifuged to obtain plasma. Tissues were rapidly dissected and snap frozen in liquid nitrogen. Samples were stored frozen at −70° C. until analysis. RA190 was extracted from mouse plasma using acetonitrile containing temazepam (100 ng/mL). Tissue homogenates were prepared at a concentration of 200 mg/mL in PBS and further diluted 1:10 in mouse plasma before extraction using acetonitrile containing temazepam (100 ng/mL). Separation was achieved on Waters X-Terra™ C$_{18}$ (50 mm×2.1 mm i.d., 3 μm) at room temperature using isocratic elution with acetonitrile/water mobile phase (70:30, v/v) containing 0.1% formic acid at a flow rate of 0.2 mL/min. Detection was performed using electrospray MS/MS operating in negative mode by monitoring the ion transitions from m/z 561.0→119.8 (RA190) and m/z 301.2→225.0 (temazepam). Samples were quantitated over the assay range of 10 to 1000 ng/mL or 0.6 to 60 μg/g. Mean plasma concentrations at each sampling point were calculated for RA190. Pharmacokinetic variables were calculated from mean RA190 concentration-time data using noncompartmental methods as implemented in WinNonlin Professional version 5.3 (Pharsight Corp., Mountain View, Calif.). Cmax and Tmax were the observed values from the mean data. The $AUC_{last}$ was calculated using the log-linear trapezoidal rule to the end of sample collection ($AUC_{last}$) and extrapolated to infinity ($AUC_{0-\infty}$) by dividing the last quantifiable concentration by the terminal disposition rate constant ($\lambda z$), which was determined from the slope of the terminal phase of the concentration-time profile. The half-life ($T_{1/2}$) was determined by dividing 0.693 by $\lambda_z$. Relative bioavailability was calculated as follows:

$$\text{Relative Bioavailability}(\%) = \left(\frac{AUC_{0-\infty,p.o.}}{AUC_{0-\infty,i.p.}}\right) * \left(\frac{Dose_{i,p}}{Dose_{p.o.}}\right)$$

Pharmacokinetic Parameters were Summarized Using Descriptive Statistics.

Complete blood count and blood chemistry analyses: After carbon dioxide euthanasia, 500 to 600 µL blood was collected from each mouse by intracardiac aspiration with a 25-gauge needle and 1-mL syringe. Blood was placed in a 600 µL centrifuge tube coated with lithium heparin to prevent clotting. A complete blood count was performed with an automated hemocytometer (Hemavet HV950FS, Drew Scientific, Oxford, Conn.). The remaining blood was centrifuged and the plasma drawn off and analyzed with an automated clinical chemistry analyzer (VeTACE, Alfa Wassermann, West Caldwell, N.J.).

In vivo DNA delivery: Gene gun particle-mediated DNA delivery was performed using a helium-driven gene gun (Bio-Rad, Hercules, Calif.) as described previously (Trimble et al., 2003). For electroporation, a patch of the mouse leg was shaved and 10 µg 4UbFL or FL DNA plasmid in 20 µL of PBS was injected into the quadriceps femoralis muscle followed immediately by injection of the 2 Needle Array to 5 mm depth encompassing the injection site and square wave electroporation (ElectroSquarePorator 833, BTX-2 Needle array 5 mm gap, Harvard apparatus) delivered as eight pulses at 106 V for 20 ms with 200 ms intervals.

In Vivo Mouse Imaging:

Two hours after gene gun delivery of the plasmid or one day post electroporation, mice were injected i.p. with 100 uL of luciferin (3 mg/mL) and anesthetized with isoflurane and optical imaging was performed for basal level luciferase expression. Images were acquired for 10 min with a Xenogen IVIS 200 (Caliper, Hopkinton, Mass.). Equally sized areas were analyzed using Living Image 2.20 software. Mice were again imaged at 4 hr and 24 hr post treatment.

In Vivo Tumor Treatment:

For TC-1 tumors, C57BL/6 mice (8/group) were challenged subcutaneously with 5×104 TC-1 cells/mice. Tumors grew for approximately 7 days until they were palpable, whereupon the mice were weighed and treatment was initiated. Tumor size was measured with a digital caliper and calculated based on the formula: [largest diameter×(perpendicular diameter)2]π/6. Nude mice (8 per group) were inoculated with 1×106 EΩ-Luciferase cells i.p. in 100 µL PBS. At day 3 mice were imaged for basal level luminescence expression. Mice were divided into two groups and treated daily i.p. with RA190 (10 mg/kg) or vehicle, and imaged again on day 7 and day 14. NOG mice (5 per group) were inoculated with 1×106 NCI-H929-GFP-Luc cells i.v., and after 4 weeks, mice were imaged for their luciferase activity and divided into two groups. Mice were treated i.p. with RA190 (20 mg/kg) or vehicle as indicated, and imaged again at the end of the treatment for their luciferase activity.

E7-Specific CD8+ T Cell Response:

Splenocytes were prepared and stimulated with HPV16 E7aa49-57 peptide (1 µg/mL) at the presence of GolgiPlug (BD Pharmingen) overnight at 37° C. The cells were first stained with PE-conjugated anti-mouse CD 8α (BD Pharmingen), then permeabilized, fixed and intracellularly stained with FITC-conjugated anti-mouse IFN-γ (BD Pharmingen). The data were acquired with FACS Calibur and analyzed with CellQuest software.

Statistical Analysis:

Results are reported as mean±standard deviation (s.d.). Statistical significance of differences was assessed by two-tailed Student's t using Prism (V.5 Graphpad, San Diego, Calif.) and Excel. The level of significance was set at p≤0.05.

Preparation of RA Series Candidate Inhibitors:

Reagents and conditions: (a) AcOH, dry HCl gas, room temperature, overnight (b) Boc or Fmoc protected amino acid, HOBt, HBTU, DMF, DIPEA, room temperature, 3 hr (c) 20% piperidine in DMF (d) 4 M HCl in dioxane.

Figure 31:
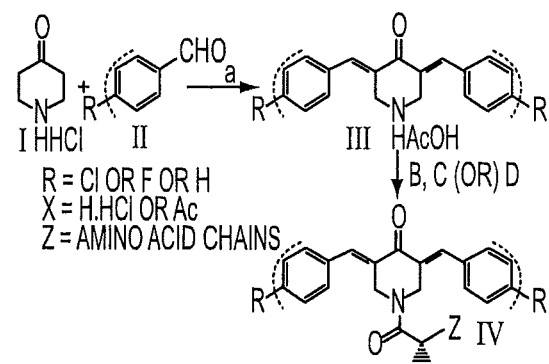
FIG. 31 shows a classical solution phase reaction used to generate various compounds.

Compounds in Tables 6 and 7 were synthesized utilizing classical solution phase reactions as seen in FIG. 31. In FIG. 31, substituted benzaldehyde (s) II (2.0 mmol) was added to a suspension of 4-piperidone hydrochloride monohydrate I (1.0 mmol) in glacial acetic acid (15 mL). Dry hydrogen chloride gas was passed through this mixture for 0.5 hr during which time a clear solution was obtained. After standing at room temperature for 24 hr, the precipitate (AcOH salt of benzylidine piperidone) Ill was collected and dried under the vacuum. Target compound (s) IV were synthesized by reacting corresponding compound (s) III and corresponding amino acids in the presence of peptide coupling agents. All the compounds were purified by HPLC and characterized by MS and NMR. For the deprotection of Boc functionality, 4M HCl in dioxane solution was used.

The general chemical structure of effective molecules is the following:

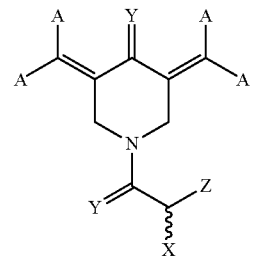

The pair of A groups represents a phenyl substituted with 1-5 substituents selected from the group consisting of R1, OR1, NR1R2, S(O)$_q$R1, SO$_2$NR1R2, NR1SO$_2$R2, C(O)R1, C(O)OR1, C(O)NR1R2, NR1C(O)R2, NR1C(O)OR2, halogen, CF$_3$, OCF$_3$, cyano, and nitro where R1 and R2 represent hydrogen, nitro, hydroxyl, carboxy, amino, halogen, and cyano or C$_1$-C$_{14}$ linear or branched alkyl groups, that are optionally substituted with 1-3 substituents selected from the group consisting of C$_1$-C$_{14}$ linear or branched alkyl, up to perhalo substituted C$_1$-C$_{15}$ linear or branched alkyl, C$_1$-C$_{14}$ alkoxy, hydrogen, nitro, hydroxyl, carboxy, amino, C$_1$-C$_{14}$ alkylamino, C$_1$-C$_{14}$ dialkylamino, halogen, and cyano.

The phenyl ring can also be replaced with a naphtha group optionally having 1-5 substituents chosen from the same list as the phenyl substituents or a 5 or 6 membered monocyclic heteroaryl group, having 1-3 heteroatoms selected from the group consisting of O, N, and S, optionally substituted with 1-3 substituents chosen from the same list as the phenyl substituents or an 8 to 10 membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of R1, OR1, NR1R2, S(O)$_q$R1, SO$_2$NR1R2, NR1SO$_2$R2, C(O)R1, C(O)OR1, C(O)NR1R2, NR1C(O)R2, NR1C(O)OR2, CF$_3$, and OCF$_3$.

X is OR1, NP, wherein P is selected from the group consisting of H, R1, C(O)R1, C(O)OR1, C(O)NR1R2, S—N(R1)COOR1, and S—N(R1). Y, NR1 or CR1R2. Y is selected from the group consisting of O, S, NR1, CR1R2. Z is selected from the group consisting of hydrogen; C$_1$ to C$_{14}$ linear, branched, or cyclic alkyls; phenyl; benzyl, 1-5 substituted benzyl, C$_1$ to C$_3$ alkyl-phenyl, wherein the alkyl moiety is optionally substituted with halogen up to perhalo; up to perhalo substituted C$_1$ to C$_{14}$ linear or branched alkyls; —(CH$_2$)$_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N and S, wherein said alkyl moiety is optionally substituted with halogen up to perhalo, and wherein the variable q is an integer ranging from 0 to 4

An embodiment with phenyl groups in place of each A pair is as follows:

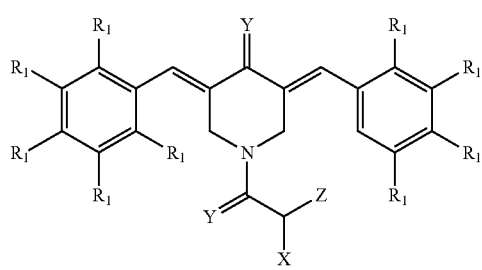

To understand the possible variations of the R1 and R2 chains, the following examples are provided:

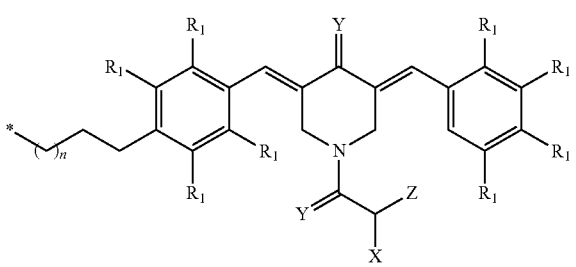

The structure above represents an R1 which is a linear alkyl chain of n repeating units.

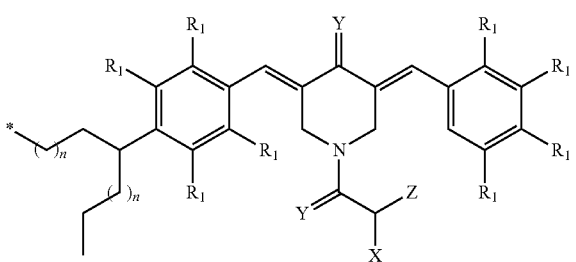

Above, R1 is a branched alkyl chain.

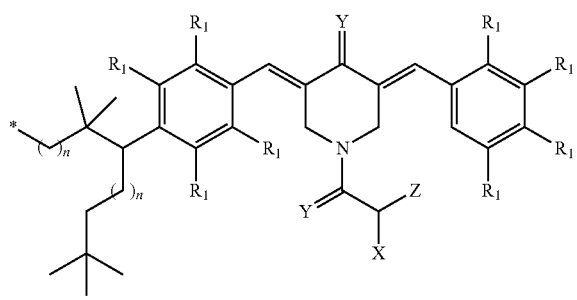

Above, R1 is a branched alkyl chain with additional substituents.

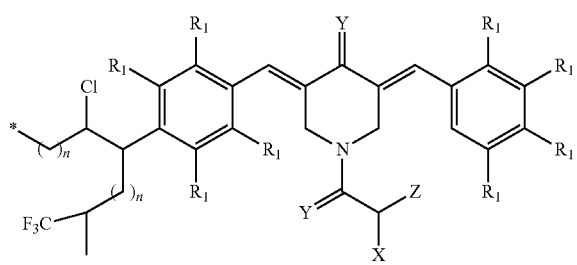

Above, R1 is a branched perhalo substituted alkyl chain.

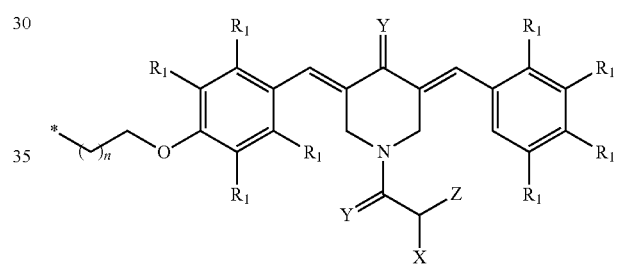

Above, R1 is an alkoxy chain (with oxygen at any position)

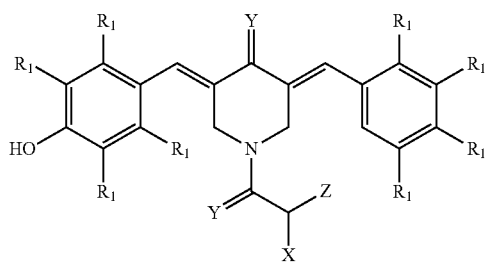

Above, R1 is hydroxy.

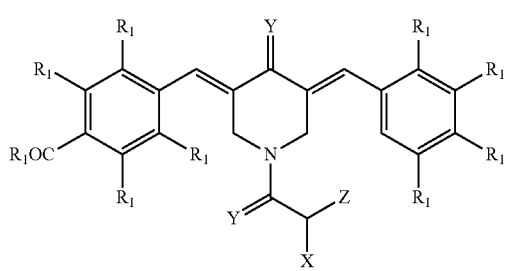

-continued
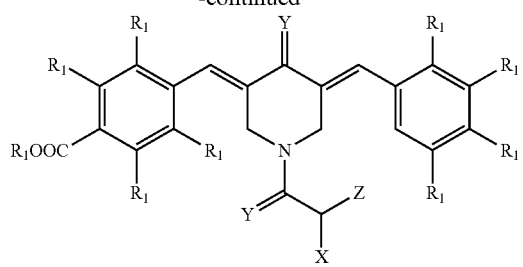
Above, R1 is Carboxy and COR1.
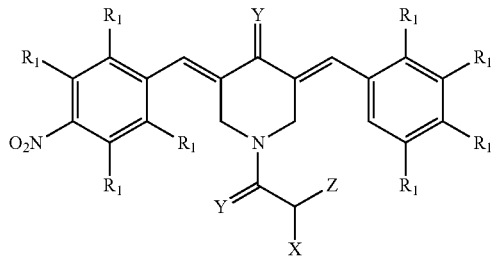
Above, R1 is Nitro.
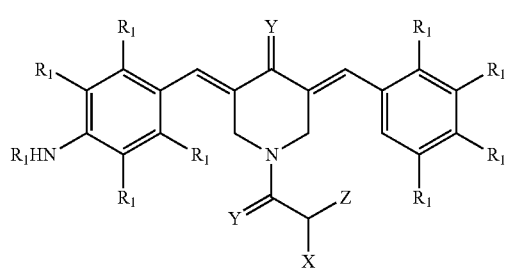
Above, R1 is $C_1$-$C_{14}$ Alkyl Amino
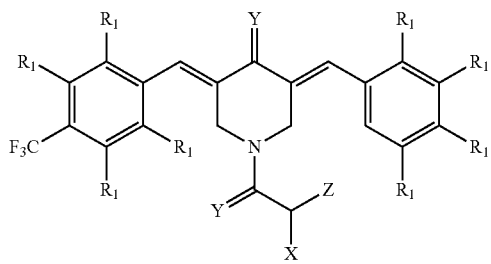
Above, R1 is $CF_3$(perfluoro).
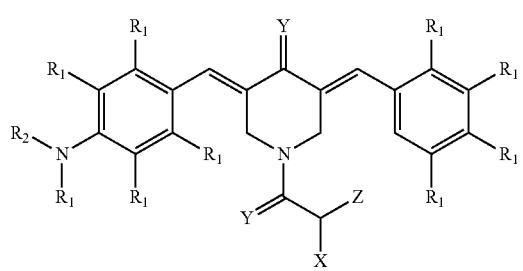
Above, R1 is $C_1$-$C_{14}$ Di Alkyl amino
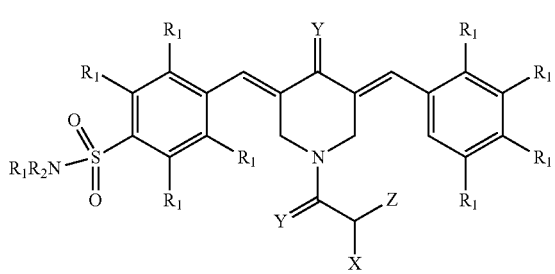
Above, R1 is SO2NR1R2
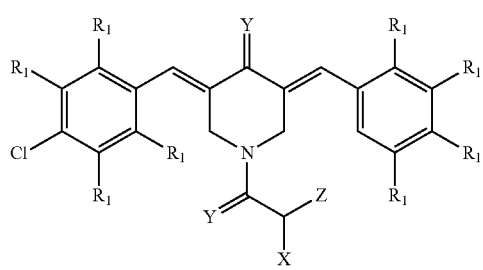
Above, R1 is any halogens (Cl, F, Br, I)
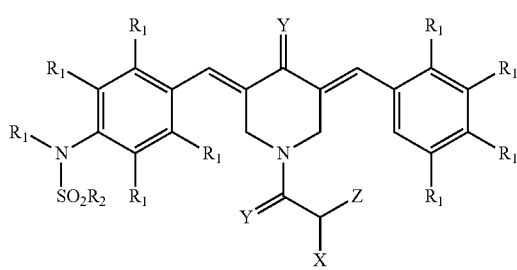
Above, R1 is NR1SO2R2
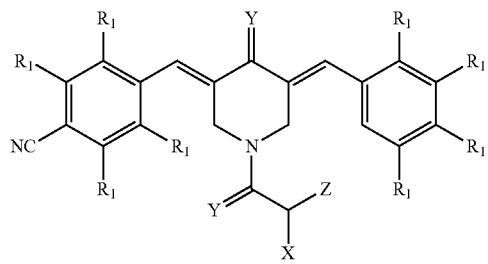
Above, R1 is Cyano.
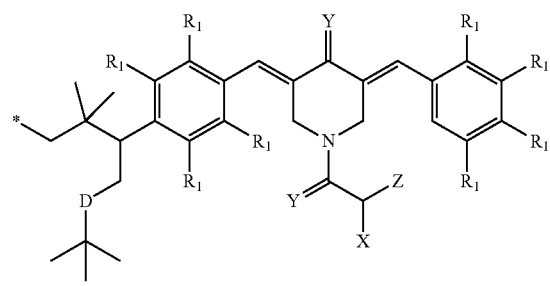
In this embodiment "D" Can be Oxygen, Nitrogen, Sulfur located anywhere in $C_1$-$C_{14}$ carbon chain

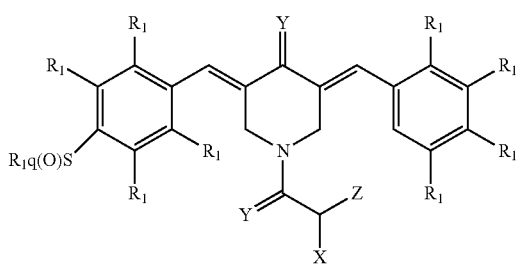

Here R1 is S(O)qR1 (Wherein the variable q is an integer selected from 0,1,2,3, or 4).

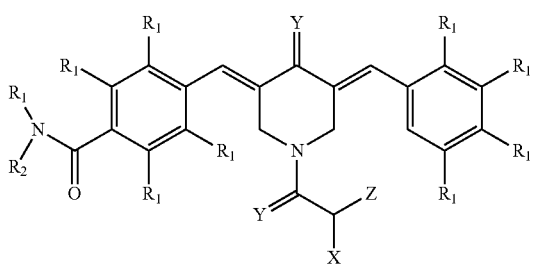

Here R1 is CONR1R2

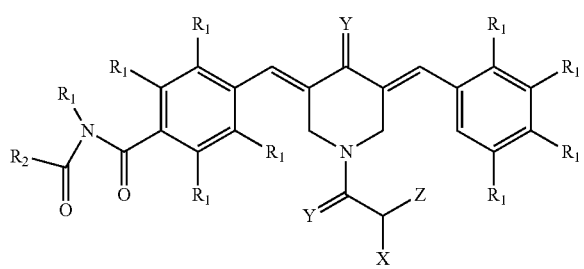

Here R1 is NR1COR2

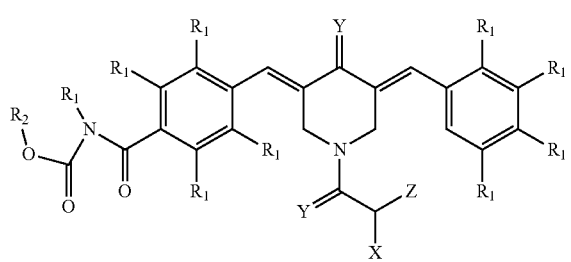

Here R1 is NR1COOR2.

Chemical Structures of RA Compounds.

Chalcones are Michael acceptors and thus their activity is modulated by electron withdrawing/donating character of substituents at the ortho and para positions of the aromatic ring. Therefore in the present study the chalcone functionality has been attached to a piperidone nucleus. We generated a new bis-benzylidine piperidone scaffold that incorporates two Michael enones in a single molecule and introduced different substituents in the aromatic ring to modulate the acceptor character of the enone system of chalcones. Using this strategy, a series of compounds was synthesized by incorporating halogens at ortho and para positions and different amino acids at the amine functionality of 4-piperidone. Since our previous work suggested the importance of phenylalanine at the amine functionality of 4-piperidone for proteasome inhibitory activity,[5] we derived a majority of RA compounds by incorporating phenylalanine and/or substituted phenylalanine at the same position along with the halogen substituents in the aromatic rings. To overcome the poor solubility and pharmacokinetics of our previous generation molecules, we employed an amide in lieu of a urea linkage between amino acids and 4-piperidone. We synthesized RA166 and RA201 with halogens chlorine and fluorine at the ortho position of aromatic rings and phenylalanine attached to the 4-piperidone. Our prior molecular modeling studies suggested the importance of having two chlorine atoms on one phenyl moiety and thus we synthesized RA190, RA190Ac which possess differences in the phenylalanine and amide conjugation as opposed to the urea conjugation of our first generation molecule RA1.[5] To gain insight into the importance of phenylalanine, we synthesized compounds RA196 and RA213 in which histidine and tyrosine are substituted for phenylalanine, and RA181, which has no substituent. Structures for RA190B and RA190ME are also provided.

Rationale for Designing Molecules:

As electrophilic agents, Michael acceptors may form covalent bonds to nucleophilic sites of proteins of biological organisms. In general, Michael acceptors (these are also called α, β-unsaturated esters, unsaturated ketones, etc.) are alkenes attached to electron-withdrawing groups (esters, ketones, nitriles, etc.). The electrophilic reactivity of Michael acceptors is an important determinant of their biological activity. In our bis-benzylidine piperidone pharmacophore, a typical Michael acceptor (in which, only one carbonyl moiety shares with two alkenes) is attached to two substituted aromatic rings at their β-carbon. Because of this arrangements aromatic ring electrons can resonate with carbonyl moiety in the Michael acceptor and ring substituents play an important role in acceptor activity.

We hypothesized that the electron withdrawing effects, number of substituents and their positions on the aromatic ring would facilitate the nucleophilic addition on the Michael acceptor in the binding site on RPN13. In our previous work we demonstrated that amino acid substituents at the secondary amine of the piperidone moiety showed greater efficacy towards the proteasome inhibition as compared to the free amine. Keeping all these criteria in view we synthesized several analogs of bis-benzylidine piperidone moiety through rational drug design.

We used Chloro and Nitro functional groups as substituent's on the aromatic ring due to their greater electron withdrawing effect at ortho (or) para (or) meta (or) both positions along with different amino acid linkages on bis-benzylidine piperidone moiety. Amino acids were chosen based in their physical characteristics like very hydrophobic (phenylalanine), strongly basic and hydrophilic (lysine), basic and hydrophilic (histidine) and amphiphilic (glycine). Commercially available Fmoc and Boc protected amino acids were used in the synthesis, and they were evaluated for their antiproliferatory activity against cancer cells. Molecules with Fmoc groups showed some impact on cancer cell proliferation but they were not soluble and potent because of the large size of the Fmoc group and possible steric hindrance. Hence, we deprotected the Fmoc group and the free amine analogs were tested for their efficacy. These new analogs with free amine showed greater anti proliferative efficacy against cancer cells but lack the solubility. To overcome this limitation, next we synthesized HCl salts of bis-benzylidine piperidones and they were more potent and solved the solubility issues associated with free amines.

Among all the analogs, Phenylalanine (RA183 and RA190) and lysine (RA195) containing molecules showed higher potency toward antiproliferative activity and accumulated Poly-ubiquitinated proteins in cancer cells. Next we synthesized another set of compounds by converting free amine functionality to its Acetate (Ac), Acrolyl (Acr) and Benzoyl (Bn) analogs as these units are part of many anticancer drugs because of their smaller size and feasibility to form inter molecular hydrogen bonds with proteins. Even though these new analogs were highly potent, HCl salts were chosen for further studies because of their better solubility.

Figure 25:
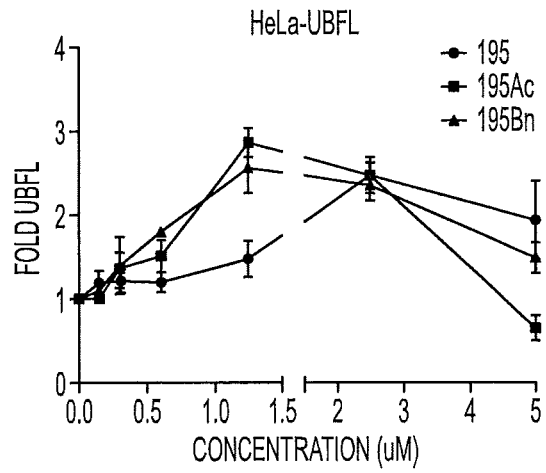
FIG. 25 shows a data graph showing that RA195 and analogs stabilize 4UBFL(tetraubiquitin firefly luciferase). HeLa cells transfected with an expression vector for 4UBFL were then treated with RA195 or its analogs RA195Ac and RA195Bn for 4 hours and Firefly Luciferase activity measured.

Many cancer cells were highly sensitive to RA190, hence we synthesized other analogs of RA190 which includes RA190P (amine functionality is converted to picolinic acid), RA190D (D-phenylalanine was used instead of L-Phenylalanine). Neither of these compounds was as good as RA190. In the RA195 molecule two amino functionalities of lysine can provide more flexibility to make better analogs. Hence, we synthesized three RA195 analogs with different functional groups at δ-amine which includes RA195F (Fmoc HCl salt), RA195Ac (Acetate HCl salt) and RA195Bn (Benzoyl HCl salt). FIG. 25 suggests that Acetate and Benzoyl versions of RA195 are more potent than the parent molecule RA195.

Rationale for RA190-Folate and RA190-Biotin:

Targeted delivery of high doses of chemotherapeutics using ligands highly needed for cancer cell survival may be an attractive alternative approach for the successful treatment of cancer. Such important ligands investigated for targeted drug delivery in recent years are folic acid and biotin.

Many cancer cells have a high requirement for folic acid and overexpress the folic acid receptor. This finding has led to the development of anti-cancer drugs that target the folic acid receptor. Folate is important for cells and tissues that rapidly divide. Cancer cells divide rapidly, and drugs that interfere with folate metabolism are used to treat cancer. The anti-folate methotrexate is a drug often used to treat cancer because it inhibits the production of the active tetrahydrofolate (THF), which is required to synthesize nucleic acids, from the inactive dihydrofolate (DHF). However, methotrexate can be toxic, producing side effects, such as inflammation in the digestive tract that make it difficult to eat normally. We use folate drug delivery approach for RA190 to target cancer cells. In this method we introduce folic acid into RA190 directly or through a spacer to make folate-RA190 (RA190-F) synthetically. RA190-Folate should have more specificity towards cancer cells as these cells are highly dependent on Folic acid and RA190-Folate and its analogs can compete with Folic acid.

Biotin is essential for cell growth, the production of fatty acids, the metabolism of fats and amino acids, and growth and development. Humans can't synthesize biotin and it is generally available from exogenous dietary sources and from intestinal bacteria. The high metabolisms of cancer cells make them depend on vitamins such as biotin (vitamin B7). Biotin levels were found to be significantly higher in many cancers especially colon and ovarian cancer tissues compared to normal tissue. At the same time these tumor cells over express biotin receptors along with folate receptors. Several research groups are pursuing biotinylated prodrugs that target biotin receptors. For example, biotinylated conjugates of camptothecin have been shown to be more cytotoxic and induce apoptosis by activation of the caspase-dependent cell death signaling pathway and were effective against multidrug resistant ovarian carcinoma cells. High availability and flexible syntheses makes biotinylated prodrugs open up a new avenue in targeted drug delivery for overcoming resistance to chemotherapy.

Following are examples of biotin and folate versions of the inventive molecules. As an overall framework the molecules can be envisioned as being based on the following generalized structure where the "ball"

represents Biotin, Folic acid, Methotrexate (MTX), or Pteroic acid.

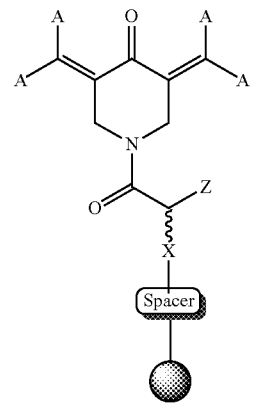

A number of molecules constructed on the same basic structure follow:

TABLE 6

Molecular formulae

|  | $D_1$ | $D_2$ | $D_3$ | E |
|---|---|---|---|---|
| RA166 | Cl | H | H | —C(=O)—CH(NH$_2$HCl)—CH$_2$—Ph |
| RA181 | H | H | H | —C(=O)—CH(NH$_2$HCl)—CH$_2$—Ph |
| RA190 | H | Cl | Cl | —C(=O)—CH(NH$_2$HCl)—CH$_2$—Ph |

TABLE 6-continued
Molecular formulae
|  | $D_1$ | $D_2$ | $D_3$ | E |
|---|---|---|---|---|
| RA190Ac | H | Cl | Cl | (S)-2-NHAc-3-phenylpropanoyl |
| RA196 | H | Cl | Cl | (S)-2-NH₂HCl-3-(pyrazol-4-yl·HCl)propanoyl |
TABLE 6-continued
Molecular formulae
|  | $D_1$ | $D_2$ | $D_3$ | E |
|---|---|---|---|---|
| RA201 | F | H | H | (S)-2-NH₂HCl-3-phenylpropanoyl |
| RA213 | H | Cl | Cl | (S)-2-NH₂HCl-3-(4-hydroxyphenyl)propanoyl |
TABLE 7
Additional Molecular Formulae:
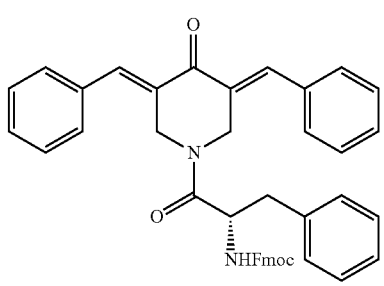
RA181F
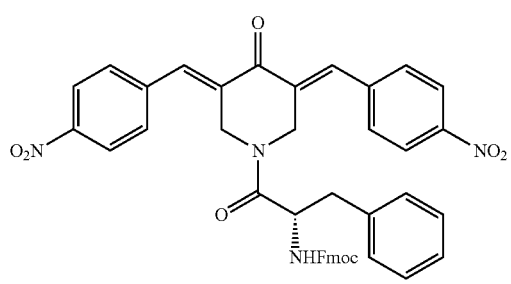
RA182
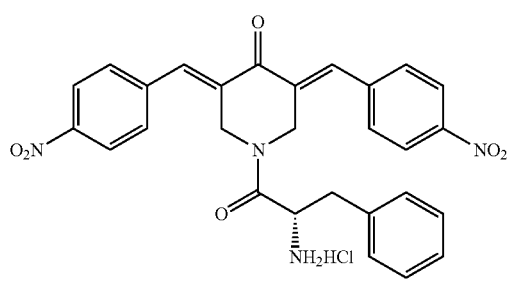
RA183

TABLE 7-continued
Additional Molecular Formulae:
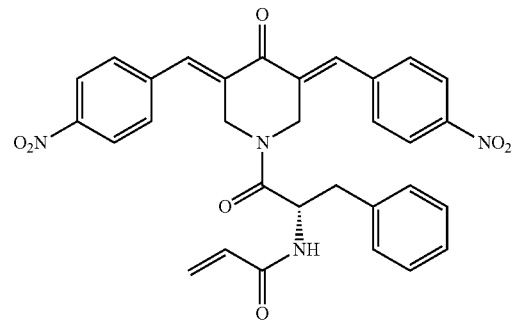 [SMILES: C=CC(=O)N[C@@H](Cc1ccccc1)C(=O)N1C/C(=C\c2ccc([N+](=O)[O-])cc2)C(=O)/C(=C/c2ccc([N+](=O)[O-])cc2)C1]
RA183Acr
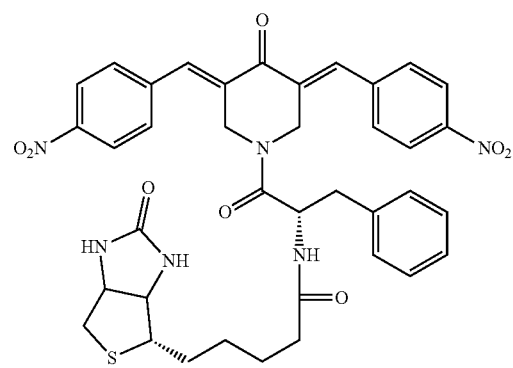 [SMILES: O=C(CCCC[C@@H]1SCC2NC(=O)NC21)N[C@@H](Cc1ccccc1)C(=O)N1C/C(=C\c2ccc([N+](=O)[O-])cc2)C(=O)/C(=C/c2ccc([N+](=O)[O-])cc2)C1]
RA183Biotin
(RA183B)
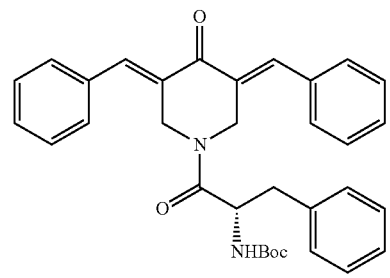 [SMILES: CC(C)(C)OC(=O)N[C@@H](Cc1ccccc1)C(=O)N1C/C(=C\c2ccccc2)C(=O)/C(=C/c2ccccc2)C1]
RA184
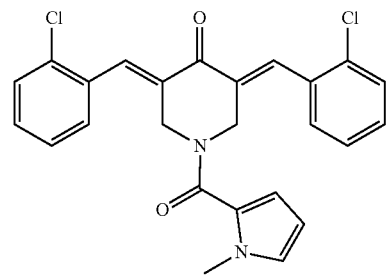 [SMILES: Cn1cccc1C(=O)N1C/C(=C\c2ccccc2Cl)C(=O)/C(=C/c2ccccc2Cl)C1]
RA186
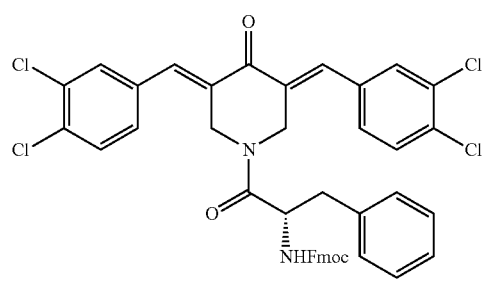
RA190F TABLE 7-continued
Additional Molecular Formulae:
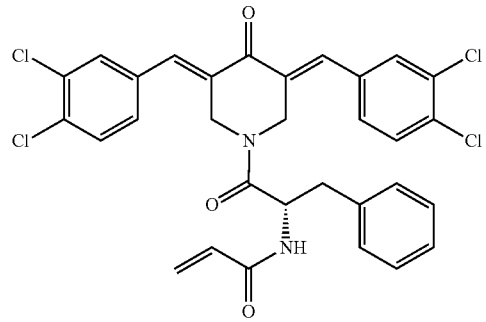 [SMILES: C=CC(=O)N[C@@H](Cc1ccccc1)C(=O)N1C/C(=C\c2ccc(Cl)c(Cl)c2)C(=O)/C(=C/c2ccc(Cl)c(Cl)c2)C1]
RA190Acr
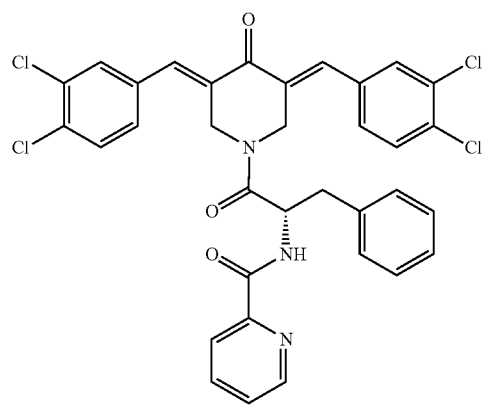 [SMILES: O=C1/C(=C/c2ccc(Cl)c(Cl)c2)CN(C(=O)[C@H](Cc2ccccc2)NC(=O)c2ccccn2)C/C1=C\c1ccc(Cl)c(Cl)c1]
RA190P
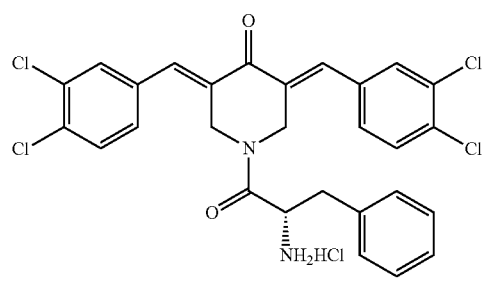
RA190D
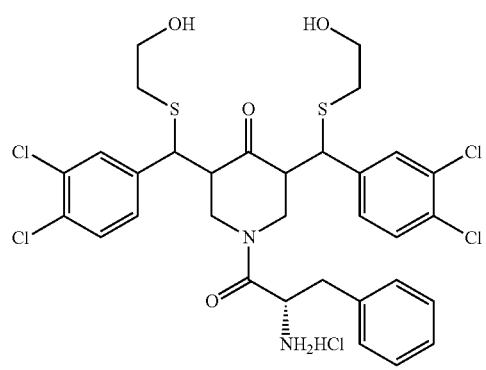
RA190ME TABLE 7-continued
Additional Molecular Formulae:
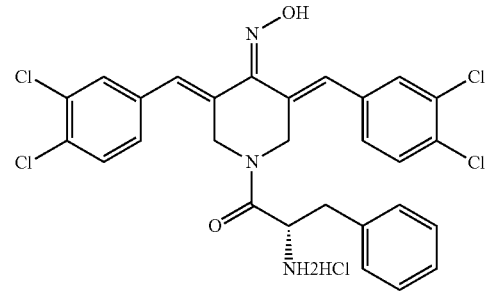
RA190O
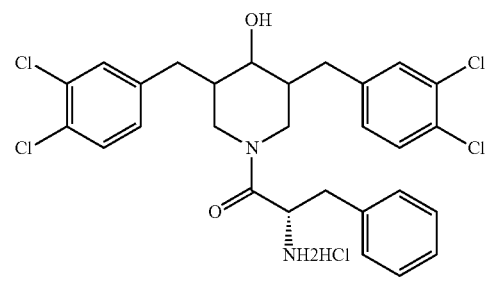
RA190R
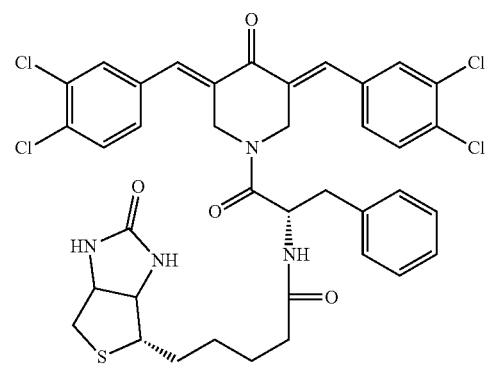 [SMILES: O=C(CCCC[C@@H]1SCC2NC(=O)NC21)N[C@@H](Cc1ccccc1)C(=O)N1C/C(=C\c2ccc(Cl)c(Cl)c2)C(=O)/C(=C/c2ccc(Cl)c(Cl)c2)C1]
RA190Biotin (RA190B)
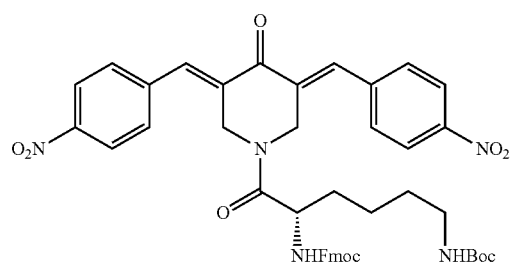
RA191
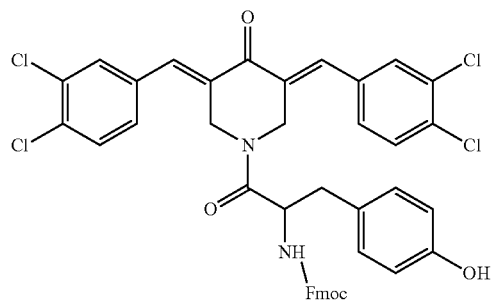
RA193

TABLE 7-continued
Additional Molecular Formulae:
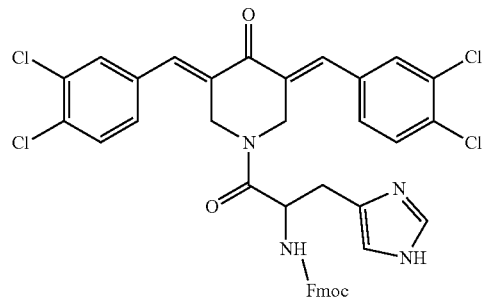
RA194
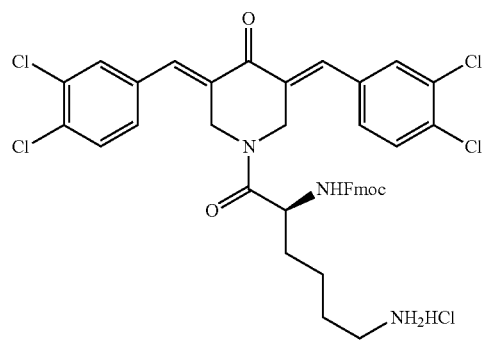
RA195
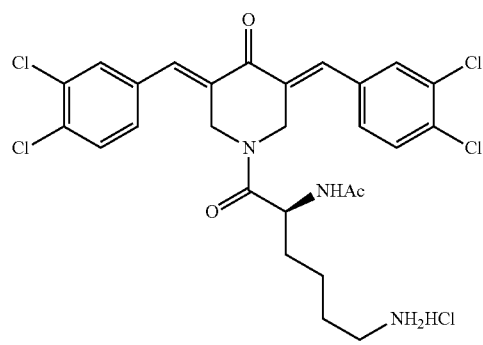
RA195Ac
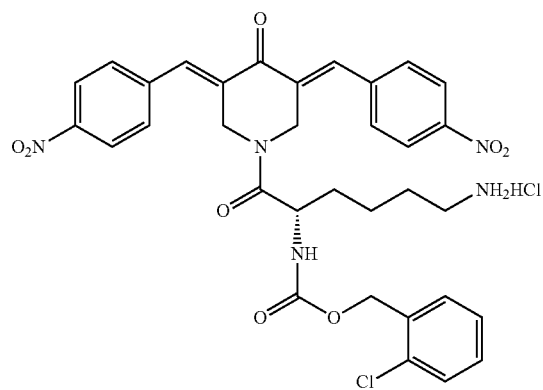
RA195Bn TABLE 7-continued
Additional Molecular Formulae:
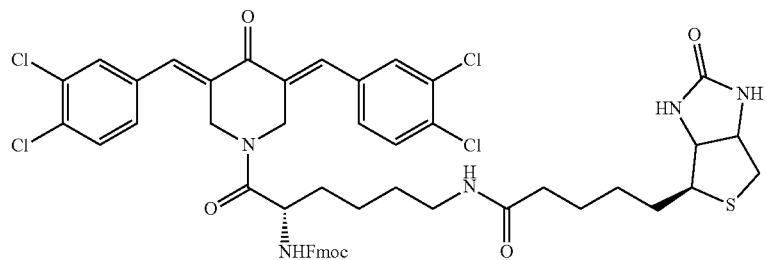
RA195Biotin
(RA195B)
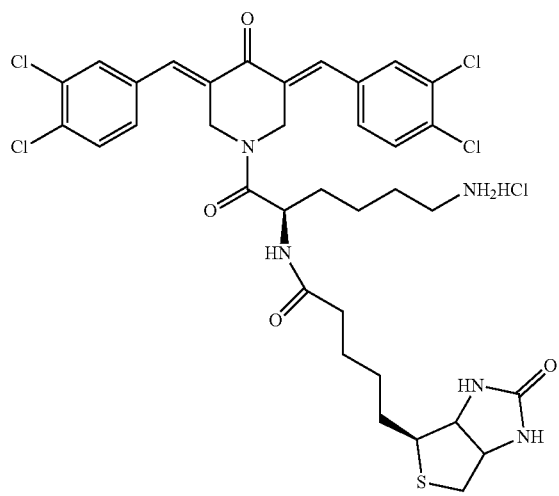
RA 195B (a)
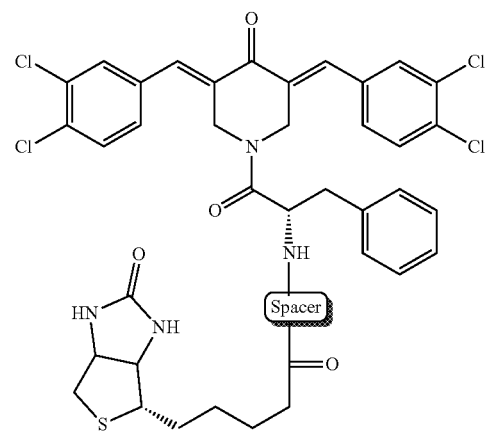
RA190-
spacer-B
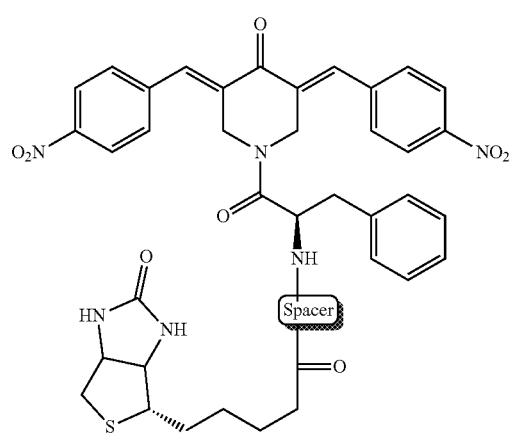
RA183-
spacer-B 51
52
TABLE 7-continued
Additional Molecular Formulae:
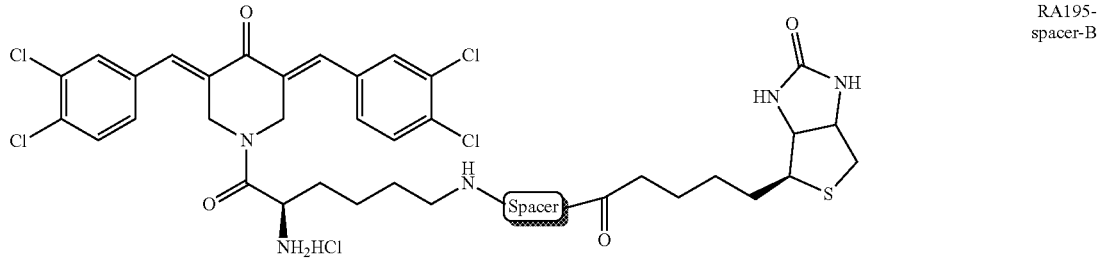
RA195-spacer-B
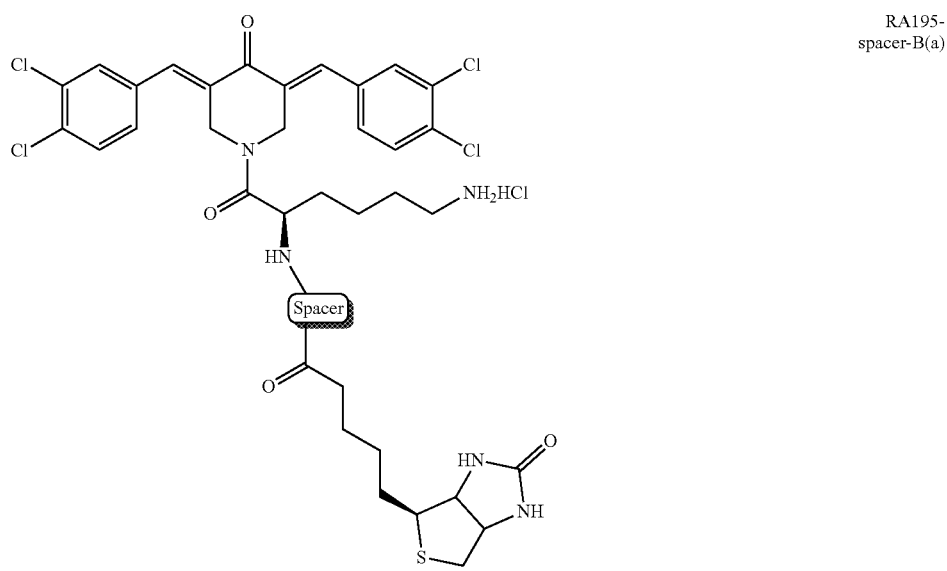
RA195-spacer-B(a)
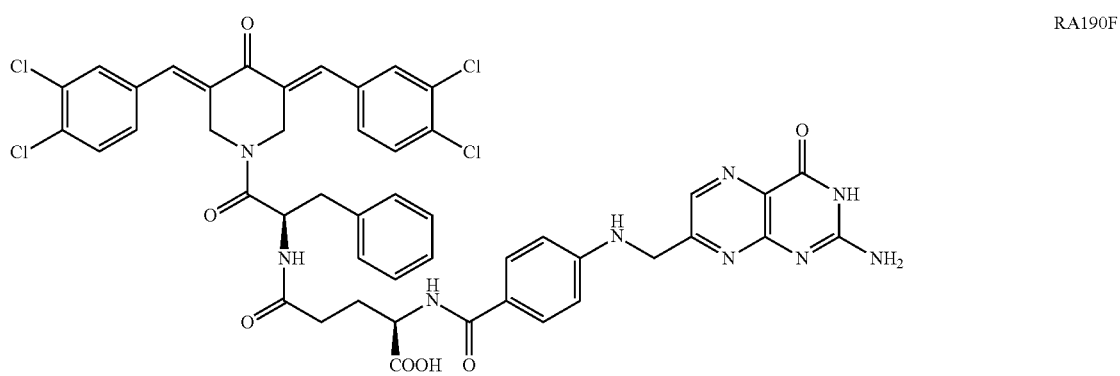
RA190F
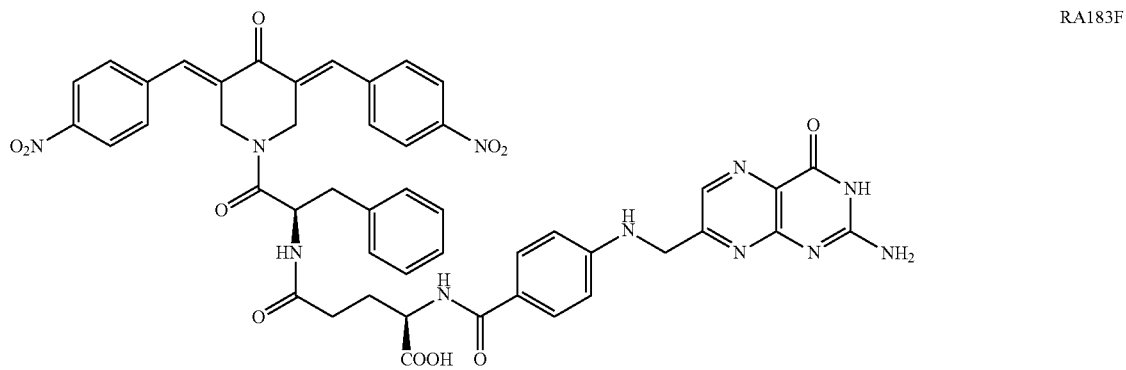
RA183F TABLE 7-continued
Additional Molecular Formulae:
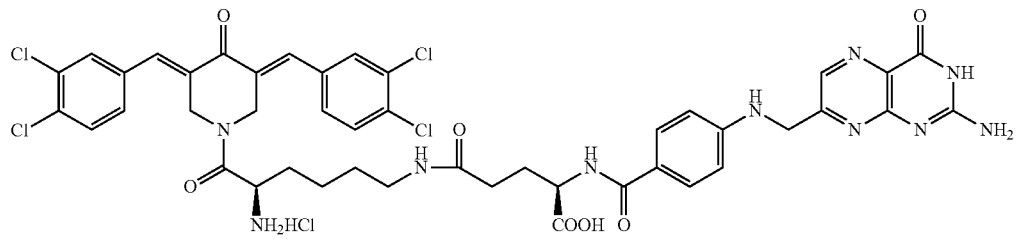
RA195F
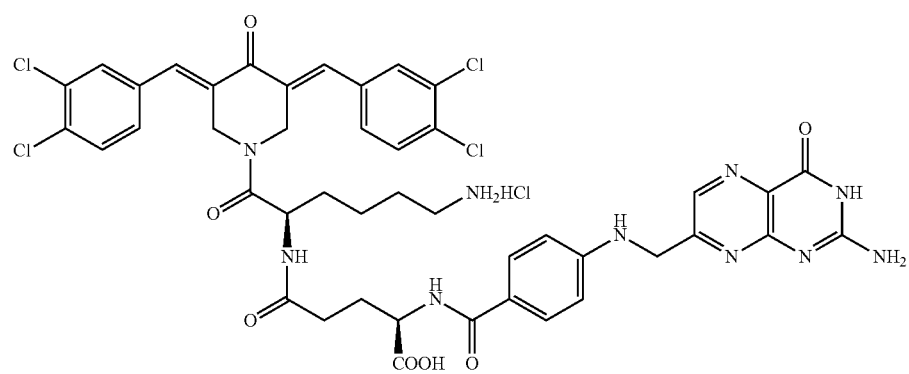
RA195F(a)
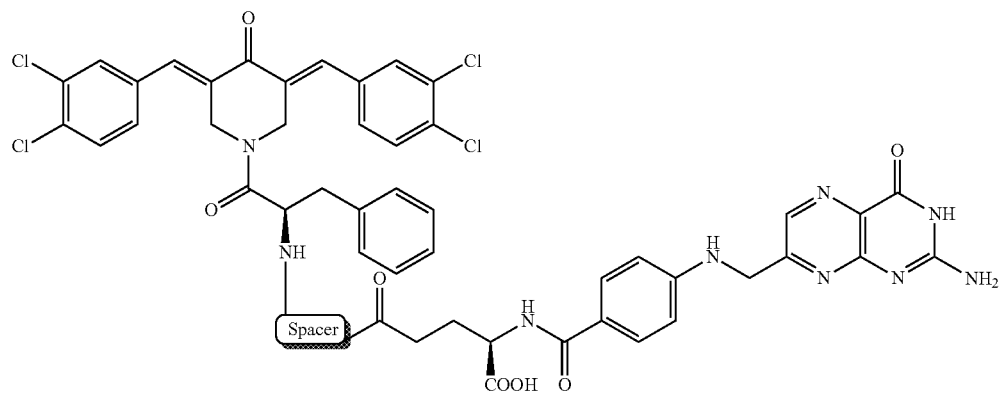
RA190-spacer-F
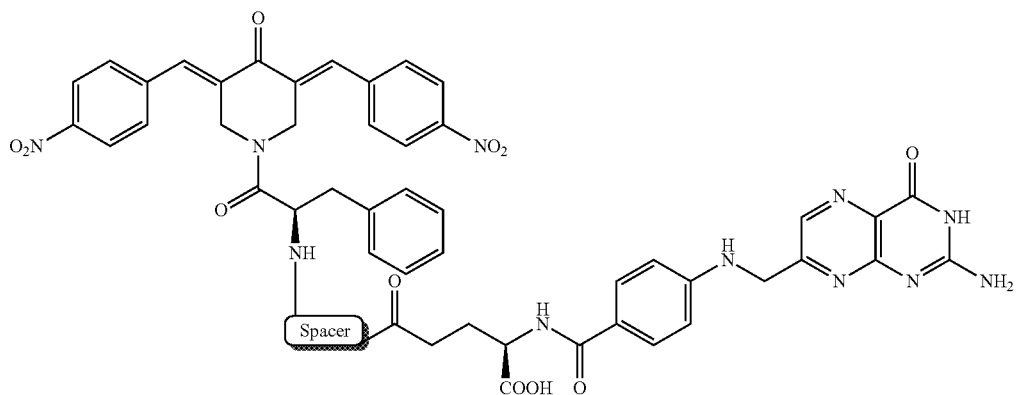
RA183-spacer-F TABLE 7-continued
Additional Molecular Formulae:
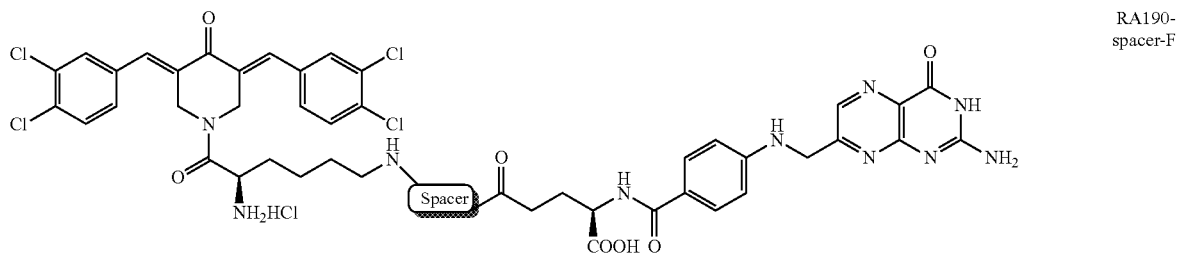
RA190-spacer-F
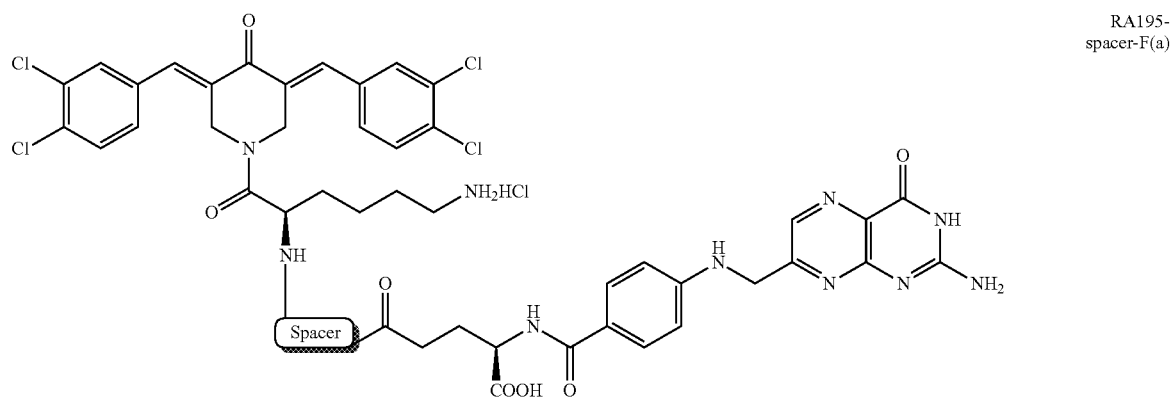
RA195-spacer-F(a)
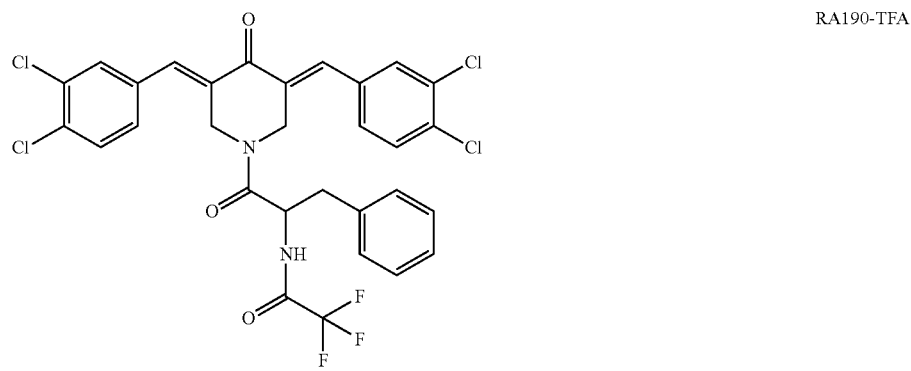
RA190-TFA
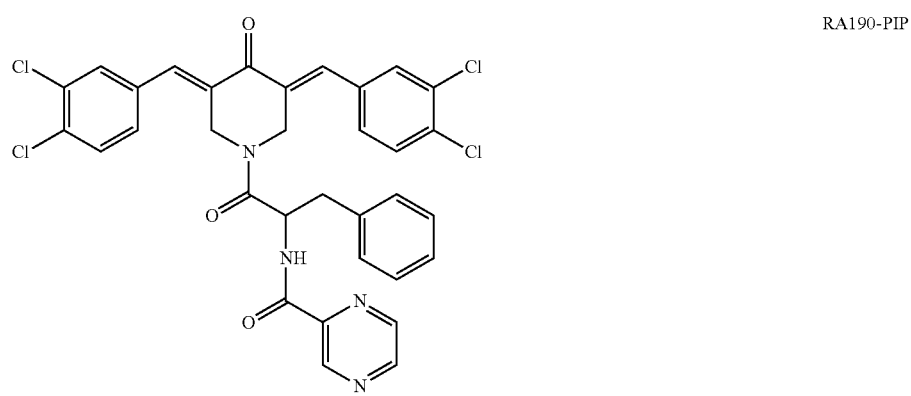
RA190-PIP TABLE 8
Chemical structures of a few related analogs of bis-Benzylidine Piperdone
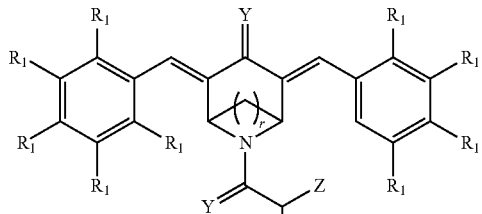
R = 0 to 14
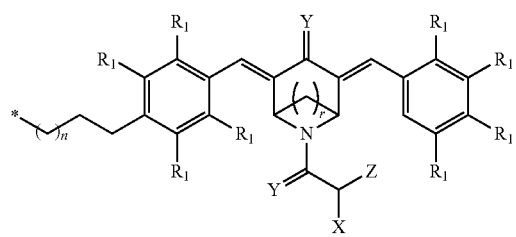
r, n = 0 to 14
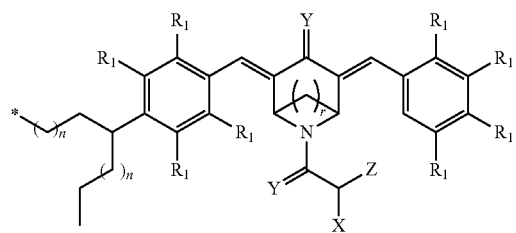
r, n = 0 to 14
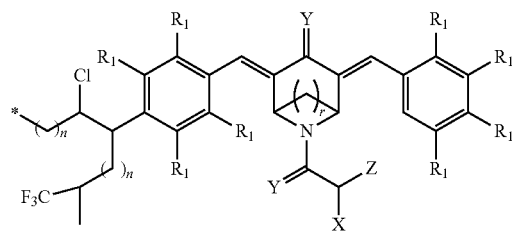
r, n = 0 to 14
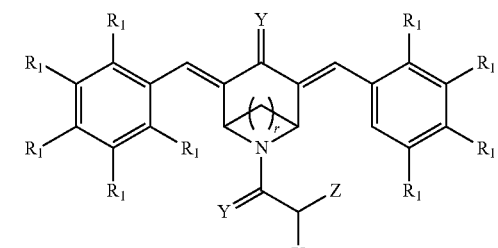
r, n = 0 to 14
TABLE 8-continued
Chemical structures of a few related analogs of bis-Benzylidine Piperdone
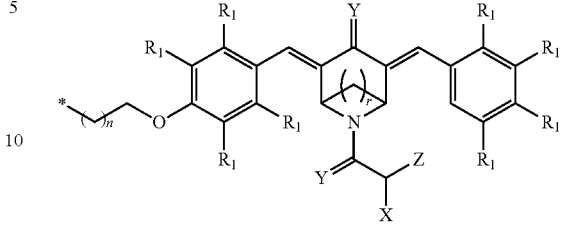
r, n = 0 to 14
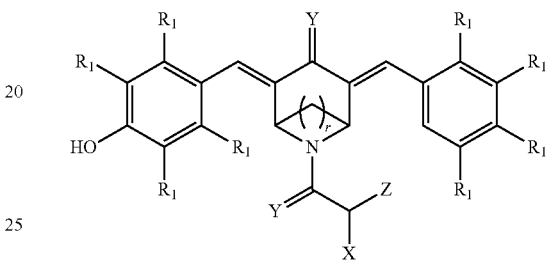
r, n = 0 to 14
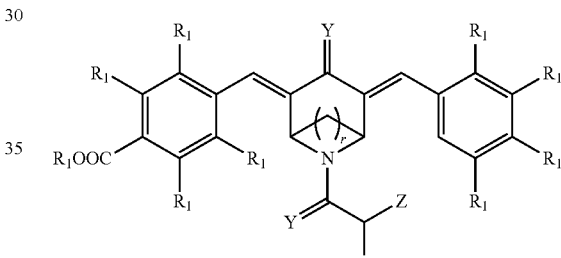
r, n = 0 to 14
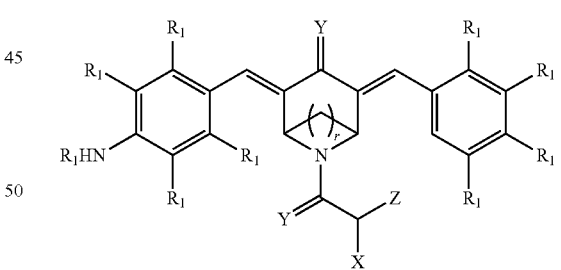
r, n = 0 to 14
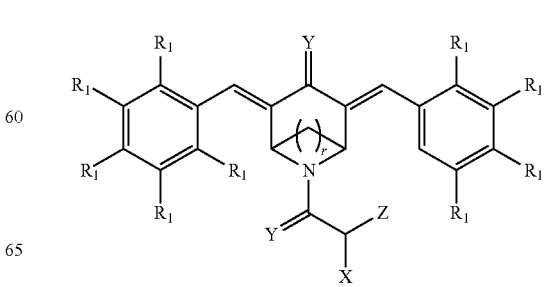

TABLE 8-continued
Chemical structures of a few related analogs of bis-Benzylidine Piperdone
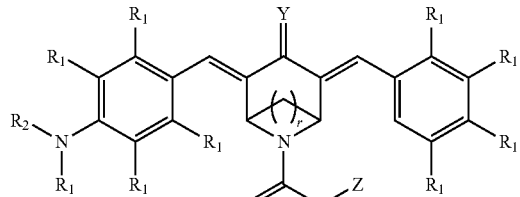
r = 0 to 14
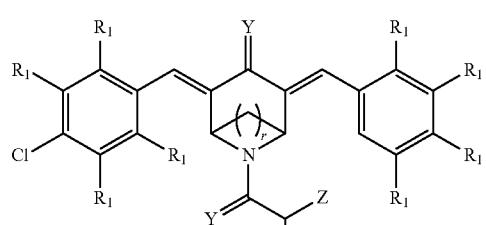
r = 0 to 14
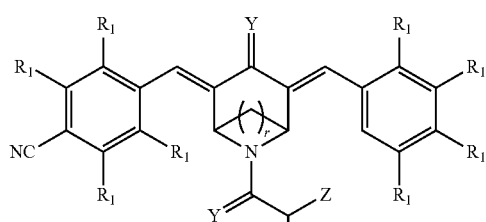
r = 0 to 14
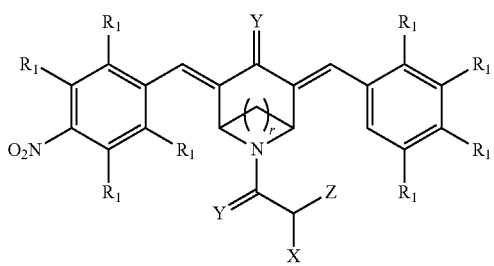
r = 0 to 14
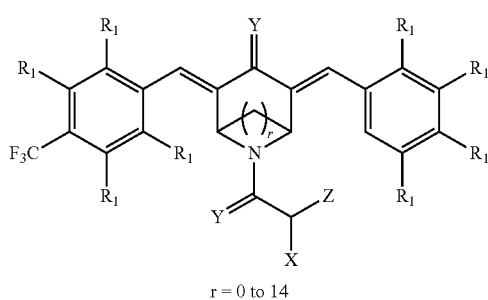
r = 0 to 14
TABLE 8-continued
Chemical structures of a few related analogs of bis-Benzylidine Piperdone
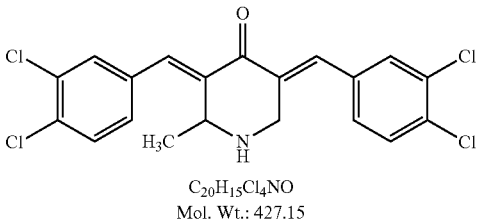 [SMILES: CC1NC/C(=C\c2ccc(Cl)c(Cl)c2)C(=O)/C1=C/c1ccc(Cl)c(Cl)c1]
C$_{20}$H$_{15}$Cl$_4$NO
Mol. Wt.: 427.15
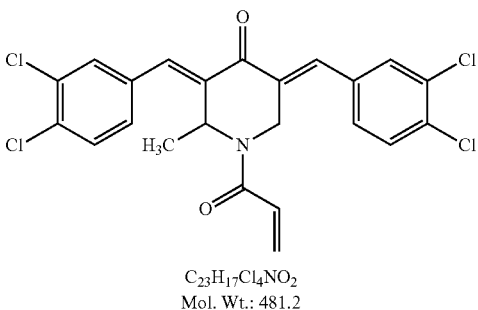 [SMILES: C=CC(=O)N1C/C(=C\c2ccc(Cl)c(Cl)c2)C(=O)/C(=C/c2ccc(Cl)c(Cl)c2)C1C]
C$_{23}$H$_{17}$Cl$_4$NO$_2$
Mol. Wt.: 481.2
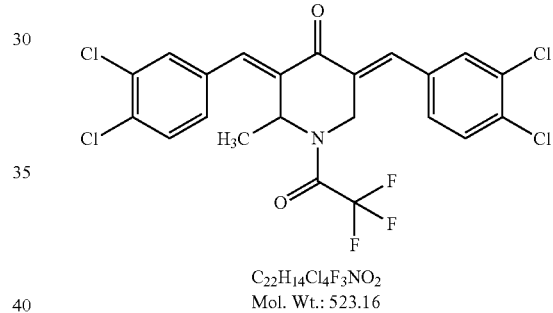
C$_{22}$H$_{14}$Cl$_4$F$_3$NO$_2$
Mol. Wt.: 523.16
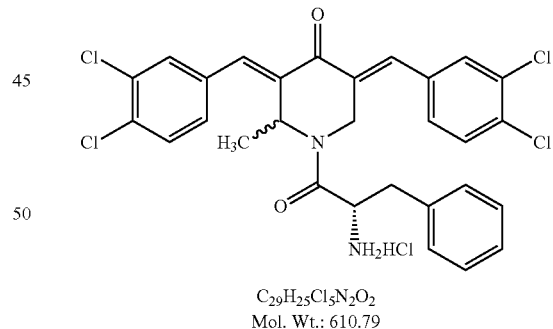
C$_{29}$H$_{25}$Cl$_5$N$_2$O$_2$
Mol. Wt.: 610.79
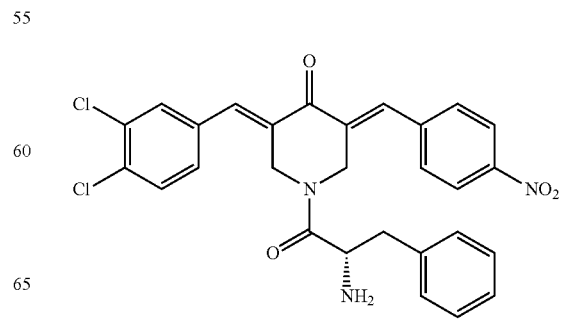

TABLE 8-continued
Chemical structures of a few related analogs of bis-Benzylidine Piperdone
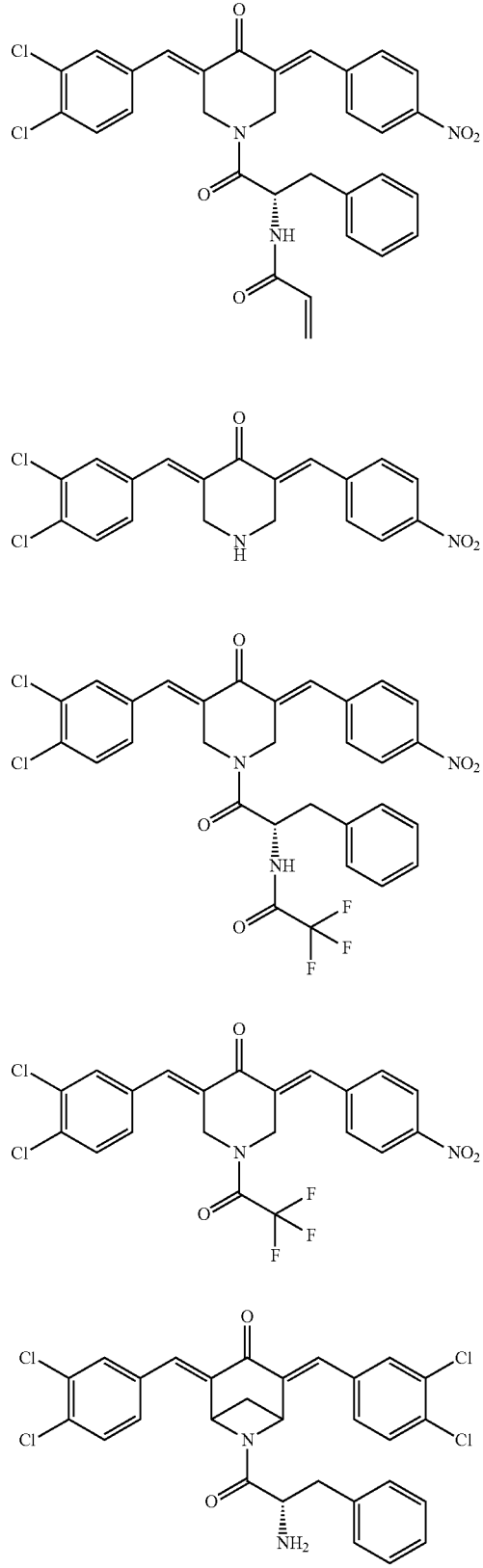
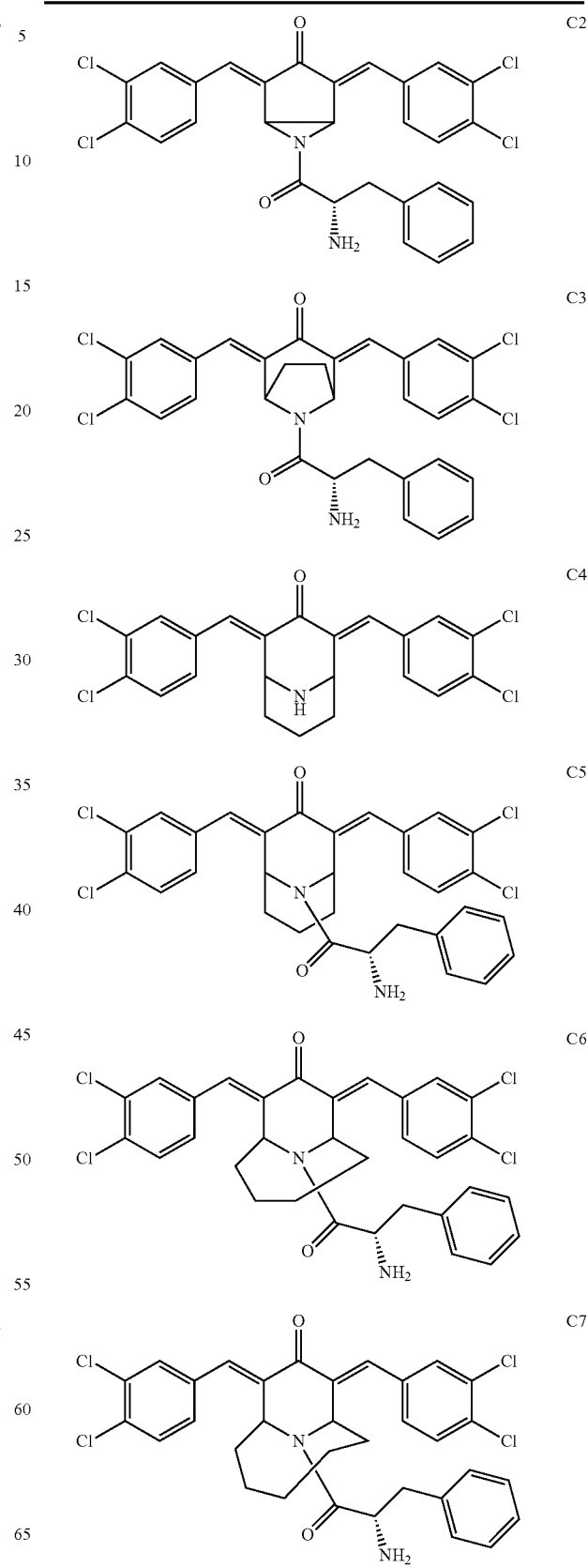

TABLE 8-continued

Chemical structures of a few related analogs of bis-Benzylidine Piperdone

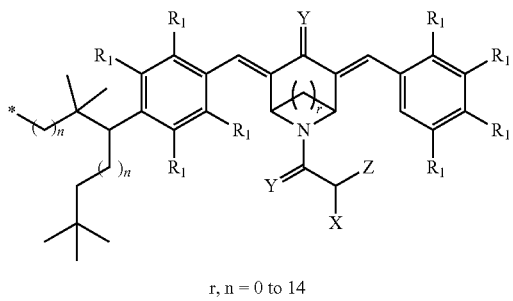

r, n = 0 to 14

Analytical Data for RA compounds:

3,5-bis(2-chlorobenzylidene)-1-(S-2-amino-3-phenyl)-piperidin-4-one-HCl salt (RA166): $^1$H NMR (DMSO-d6): δ 7.90 (d, 2H, J=8 Hz), 7.11-7.53 (m, 11H), 6.78-6.91 (m, 2H), 5.21-5.41 (m, 1H), 4.87 (d, 1H, J=16.0 Hz), 4.51 (d, 1H, J=18.0 Hz), 4.39 (d, 1H, J=18.0 Hz), 4.20 (d, 1H, J=16.0 Hz), 2.78-2.93 (m, 2H); EIMS: m/z: 493 (M+-HCl); HPLC purity: >95%

3,5-dibenzylidene-1-(S-2-amino-3-phenyl)-piperidin-4-one-HCl salt (RA181):$^1$H NMR (DMSO-d6): δ 7.82 (d, 2H, J=16.0 Hz), 7.17-7.75 (m, 15H), 4.91-4.95 (m, 1H), 4.67 (d, 1H, J=16.0 Hz), 4.29-4.51 (m, 3H), 3.21-3.38 (m, 2H); EIMS: m/z: 422 (M+-HCl); HPLC purity: >95%

3,5-bis(3,4-dichlorobenzylidene)-1-(S-2-amino-3-phenyl)-piperidin-4-one-HCl salt (RA190): $^1$H NMR (DMSO-d6): δ 8.02 (s, 1H), 7.11-7.27 (m, 11H), 6.98 (s, 2H), 4.95 (d, 1H, J=16.0 Hz), 4.68 (d, 1H, J=18.0 Hz), 4.51-4.68 (m, 2H), 4.14 (d, 1H, J=18.0 Hz), 2.95 (dd, 1H, J=14.0 Hz), 2.80 (dd, 1H, J=14.0 Hz); 13C (DMSO-d6): 185.4, 174.9, 143.7, 141.5, 139.2, 138.3, 135.6, 131.7, 129.9, 128.6, 127.1, 125.3, 54.7, 46.9, 42.1; EIMS: m/z: 562 (M+-HCl); HPLC purity: 99% (21.7 min)

3,5-bis(3,4-dichlorobenzylidene)-1-(N-(1-oxo-S-3-phenyl-1-propan-2-yl) acetamide)-piperidin-4-one-HCl salt (RA190Ac): $^1$H NMR (CDCl3): δ 8.12 (s, 1H), 7.57 (s, 2H), 7.11-7.27 (m, 11H), 4.97 (dd, 1H, J=16.0 Hz), 4.83 (d, 1H, J=18.0 Hz), 4.74 (d, 1H, J=18.0 Hz), 4.41 (d, 1H, J=16.0 Hz), 4.12-4.19 (m, 1H), 3.19 (d, 1H, J=14.0 Hz), 3.08 (d, 1H, J=14.0 Hz), 2.13 (s, 3H); EIMS: m/z: 603 (M+); Log P: 5.91, C Log P: 7.33; HPLC purity: 99%

3,5-bis(3,4-dichlorobenzylidene)-1-(S-1H-imidazol-4-yl) piperidin-4-one di HCl salt (RA196): $^1$H NMR (DMSO-d6): δ 12.2 (s, 1H), 6.98-7.89 (m, 10H), 4.96 (d, 1H, J=16.0 Hz), 4.74 (d, 1H, J=18.0 Hz), 4.39-4.41 (m, 2H), 4.27 (d, 1H, J=18.0 Hz), 2.89-3.16 (m, 2H); EIMS: m/z: 551 (M+-HCl); HPLC purity: >95%

3,5-bis(2-fluorobenzylidene)-1-(S-2-amino-3-phenyl)-piperidin-4-one-HCl salt (RA201): $^1$H NMR (DMSO-d6): δ 7.96 (d, 2H, J=8.0 Hz), 7.21-7.58 (m, 13H), 4.94-5.09 (m, 1H), 4.89 (d, 1H, J=16.0 Hz), 4.55 (d, 1H, J=18.0 Hz), 4.43 (d, 1H, J=18.0 Hz), 4.260 (d, 1H, J=16.0 Hz), 2.76-2.97 (m, 2H); EIMS: m/z: 458 (M+-HCl); HPLC purity: >95%.

3,5-bis(3,4-dichlorobenzylidene)-1-(S-2-amino-3-(4-hydroxy)-phenyl)-piperidin-4-one HCl salt (RA213): $^1$H NMR (DMSO-d6): δ 7.62 (s, 2H), 6.98-7.25 (m, 10H), 4.99 (d, 1H, J=16.0 Hz), 4.75 (d, 1H, J=18.0 Hz), 4.59-4.72 (m, 2H), 4.29 (d, 1H, J=18.0 Hz), 2.89-3.17 (m, 2H); EIMS: m/z: 474 (M+-HCl); HPLC purity: >95%

3,5-bis((2-hydroxyethylthio)(3,4-dichlorophenyl) methyl)-1-(S-2-amino-3-phenyl)-piperidin-4-one-HCl salt (RA190ME): $^1$H NMR (CDCl3): 7.01-7.58 (m, 11H), 4.09- 4.95 (m, 11H), 3.17-3.98 (m, 4H), 2.23-2.87 (m, 4H); EIMS: m/z: 716 (M+-HCl); HPLC purity: 95%.

HPLC Conditions for RA190 Purification.

TABLE 9

| HPLC conditions for RA190 purification: | | | |
|---|---|---|---|
| Time (min) | Flow (mL) | % A (water/5% acetonitrile, 0.1% TFA) | % B (Acetonitrile-0.1% TFA) |
| 0.01 | 1.00 | 80.0 | 20.0 |
| 5.00 | 6.00 | 80.0 | 20.0 |
| 20.00 | 6.00 | 5.0 | 95.0 |
| 30.00 | 6.00 | 95.0 | 5.0 |
| 30.01 | 0.00 | 95.0 | 5.0 |

Figure 17:
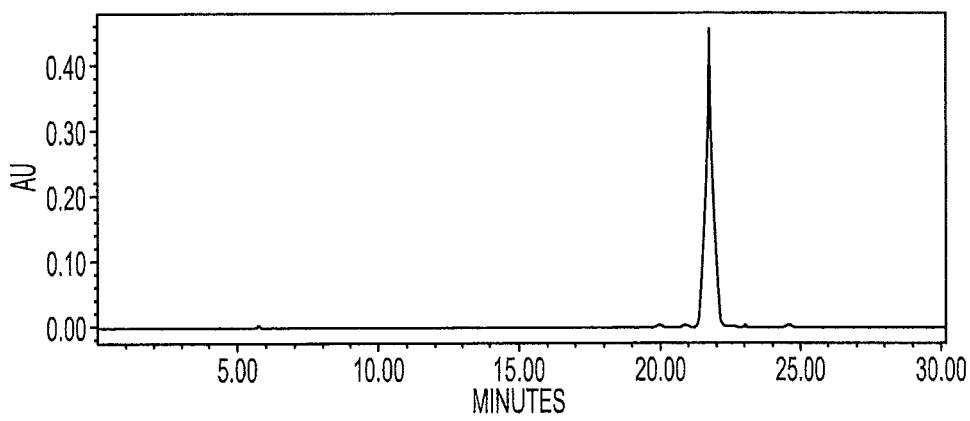
FIG. 17 shows a representative HPLC trace for RA190 purification.

FIG. 17 shows a representative HPLC trace for RA190 purification, with a peak appearing after 21 minutes. High-performance liquid chromatography (HPLC), is a technique in analytic chemistry used to separate the components in a mixture, to identify each component, and to quantify each component and to analyze the purity of given compound. Single peak at 21 minutes indicates RA190 eluting time is 21 minutes at given HPLC method and indicates the presence of single compound without impurities.

Additional Experiments

HeLa cells were treated with RA190, RA190B(RA190-Biotin) at various concentrations for the period of 12 h and cell lysate was subjected to western blot analysis using anti Ubiquitin and PARP antibodies. A build-up of poly-ubiquitinated proteins in response to the inhibition of the proteasome by the treatments was observed. In addition, a western blot analysis using anti-Ubiquitin and anti-PARP antibodies was conducted and the RA190 treatments stimulated cleavage of PARP which lead to cell death.

FIG. 18 shows the results of HeLa cells that were treated with RA190, RA190B (RA190-Biotin) and RA190R for the period of 48 h. Cell viability was measured using MTT reagent. Significantly, the RA190 treatment resulted in significant loss of cell viability.

20S Proteasome Chymotryptic Activity Assay:

FIG. 19 shows the results of a RA183, RA190 and RA195 20S proteasome inhibition assay. All tested compounds were observed to inhibit proteasome activity. Purified 20S proteasome (500 ng) was incubated with different RA compounds (1 µM) along with bortezomib (Bz, 1 uM) for 30 min and 75 µM substrate (Suc-LLVY-AMC) was added and read the AMC release by measuring the fluorescence using fluorometer. 20S proteasome cleaves the chymotryptic substrate and releases fluorescent AMC. Whereas bortezomib inhibits this chymotryptic activity of the 20S proteasome, RA190, RA183, and RA195 do not at a concentration of 1 µM.

RA190 Inhibits TNFα-Induced NFκB Activation 293 cells transiently transfected with either NFκB/FL (firefly luciferase reporter construct under control of an NFκB-driven promoter) or control CMV promoter-driven FL reporter construct were treated with compounds and TNFα (10 ng/ml) for 7 h. Upon the addition of luciferin, bioluminescence was measured in cell lysates using a luminometer. Results can be seen in FIG. 20.

RA190 Effect on Pancreatic Cancer

Figure 21A:
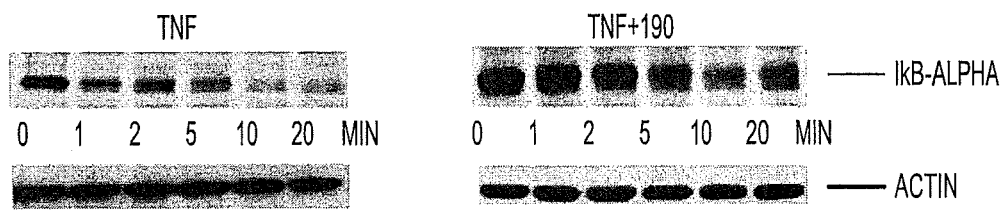
FIG. 21A shows an immunoblot of PAO3C cell lysates.
Figure 21B:
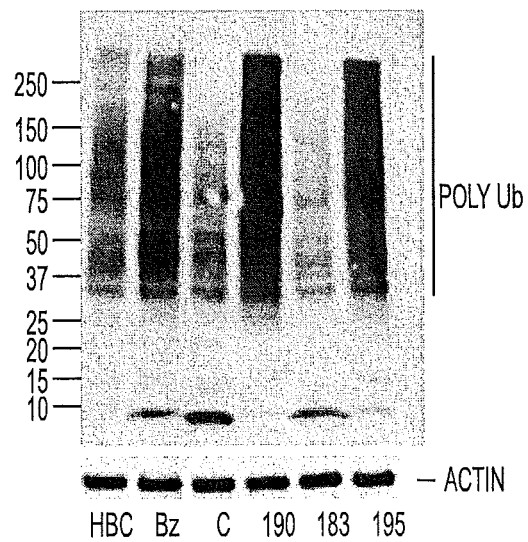
FIG. 21B shows an immunoblot showing the effect of RA190 on the poly-ubiquitinated protein levels.

FIGS. 21A-21F show a series of immunoblots and data graphs on the effect of various compounds on pancreatic cancer cells. 21A shows an immunoblot of PAO3C cell lysates. 21B shows an immunoblot showing the effect of RA190 on the poly-ubiquitinated protein levels. 21C shows an immunoblot showing the effect of RA190 on the levels of apoptotic proteins and activated caspase-3. 21D shows an immunoblot showing the effect of RA190 on CDK inhibitor p27. 21E shows a data graph showing the effect of RA190 on Annexin V positive cells. 21F shows a data graph showing the effect of RA190 on active-caspase-3. FIG. 21B shows PAO3C cells treated with compounds (1 μM) for the period of 12 h. Lysate was Subjected to western blot and probed with Ubiquitin antibody. Actin used as reference control, Bz=Bortezomib. Note: High molecular weight poly ubiquitinated proteins in RA190 and RA195 lanes indicate inhibition of 19S proteasome.

FIG. 21B shows PAO3C cells treated with compounds (1 uM) for the period of 12 h. Lysate was Subjected to western blot and probed with Ubiquitin antibody. Actin used as reference control, Bz=Bortezomib. Note: High molecular weight poly ubiquitinated proteins in RA190 and RA195 lanes indicate inhibition of 19S proteasome.

Figure 21C:
FIG. 21C shows an immunoblot showing the effect of RA190 on the levels of apoptotic proteins and activated caspase-3.

FIG. 21C shows PAO3C cells treated for the period of 24 h with corresponding compounds (1 μM). Lysate subjected to western blot and probed with Bax (A) and PARP (B) antibodies. Up regulation of both proteins in the presence of compounds indicates apoptosis.

Figure 21D:
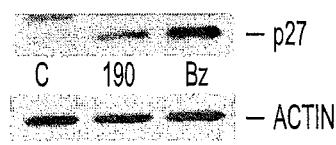
FIG. 21D shows an immunoblot showing the effect of RA190 on CDK inhibitor p27.
Figure 21E:
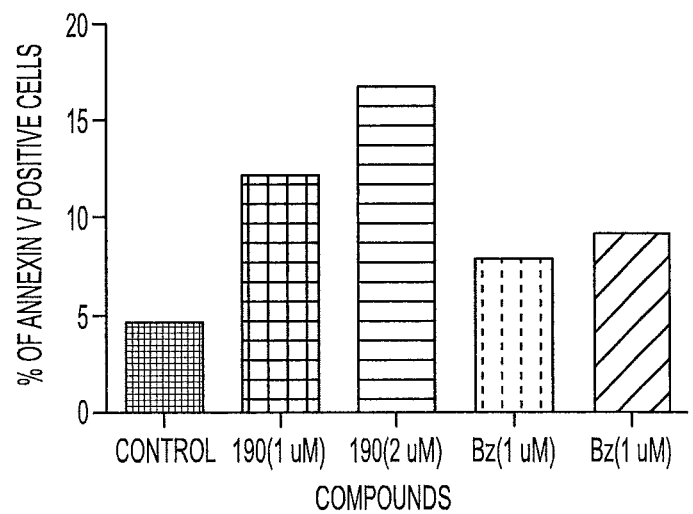
FIG. 21E shows a data graph showing the effect of RA190 on Annexin V positive cells.

FIG. 21D shows PAO3C cells treated with compounds (1 μM) for the period of 12 h. Lysate was subjected to western blot and probed with CDK inhibitor p27. Up regulation is seen with both compounds compared to the control. Actin used as reference control. FIG. 21E shows PAO3C cells treated with compounds for the period of 12 h and stained with PE-Annexin. Annexin V +ve cells were analyzed by FACS.

Figure 21F:
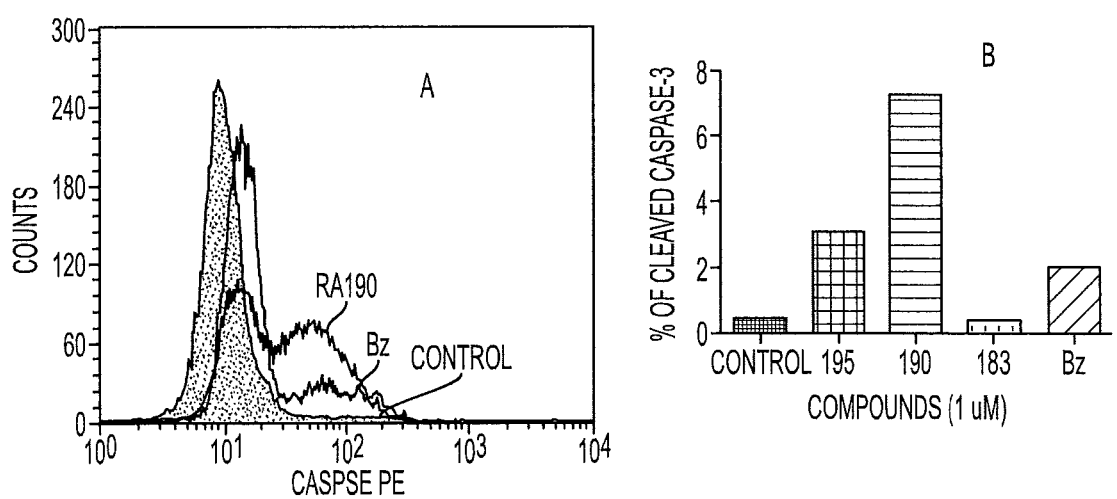
FIG. 21F shows a data graph showing the effect of RA190 on active-caspase-3.

FIG. 21F shows BxPC-3 (left) and PAO3C (right) cells treated with compounds for the period of 12 h and analyzed for active caspase-3 positive cells by FACS.

Studies on RA195 and Analogs
Cell Viability Assay

Multiple Myeloma and isogenic Colon Cancer cells (HCT116) were treated with corresponding compounds for the period of 48 h and cell viability was measured using XTT assay. IC50 values were determined in triplicate and are presented in μM. As seen in FIGS. 22A-D, compounds affect the viability of NCI-H929 (FIG. 22A), U266 (FIG. 22B) and HCT116 cells (FIGS. 22C and 22D). FIGS. 22A-22D show a series of data graphs showing the effect of indicated compounds on the viability of various cancer cell lines. 22A shows a data graph showing the effect of indicated compounds on NCI-H929 cell viability. 22B shows a data graph showing the effect of indicated compounds on U266 cell viability. 22C and 22D show data graphs showing the effect of indicated compounds on HCT116 cell viability.

RA195 Binds Covalently to Rpn13

Figure 23:
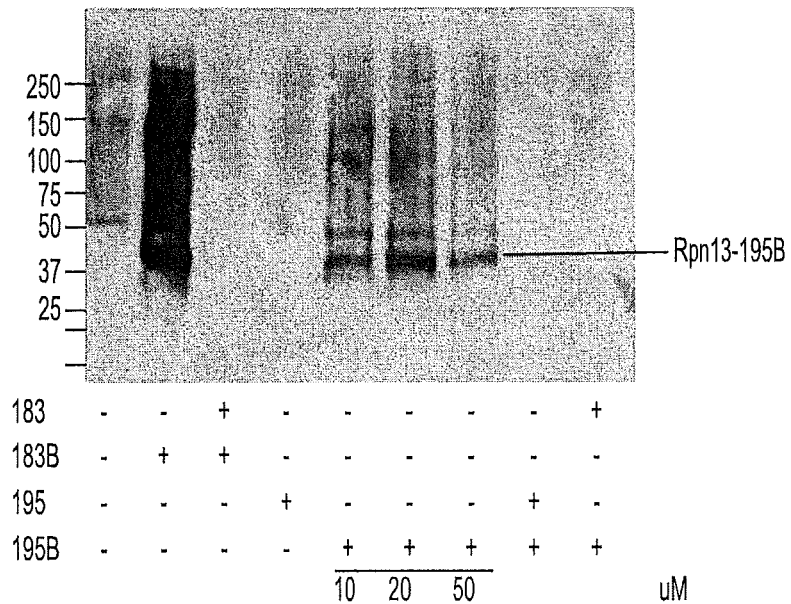
FIG. 23 shows streptavidin peroxidase-probed blot showing that RA195 binds covalently to RPN13. HeLa cell lysate was incubated with corresponding compounds (RA183 and RA183 B=20 μM; RA195=20 μM; RA195B=10, 20, 50 μM) for 1 hour at 4° C. and subjected to SDS-PAGE, transfer to a PVDF membrane and probed using HRP-Streptavidin peroxidase. RA195B labels HeLa cell lysate at 42 KDa which disappears with the pretreatment of RA195 indicates that RA195 also binds to RPN13.

Purified 19S proteasome (500 ng) was incubated with corresponding compounds for 30 min and subjected to immunoblot and probed with HRP-conjugated streptavidin. In FIG. 23, the single band at 42 KDa indicates Rpn13 binding to 195. RA183B (20 μM) is used as positive control for Rpn13 binding. Competition experiments were done with RA183 (100 μM) and RA195 (100 μM) along with RA195B (20 μM). No binding was observed in the lanes of RA183 (20 μM) and RA195 (20 μM) alone and in competition experiments.

Figure 24:
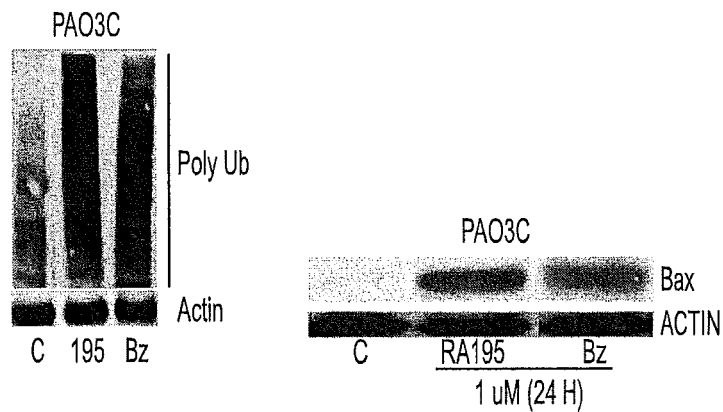
FIG. 24 shows an immunoblot showing that RA195 causes accumulation of Poly-Ubiquitinated proteins (left) and elevation of apoptotic protein Bax (right)

RA195 Caused Accumulation of Poly Ubiquitinated Proteins and Elevation of Apoptotic Protein Bax in Pancreatic Cell Line In FIG. 24, PAO3C cells were treated with RA195(195, 1 uM), Bortezomib (Bz, 1 μM) and DMSO (C) for the period of 12 h. Cell lysate was subjected to immunoblot and probed for anti UB antibody. For Bax proteins levels cells were treated for 24 hr. Actin used as positive control. The results show that RA195 causes accumulation of Poly Ubiquitinated proteins (left) and elevation of apoptotic protein Bax (right).

RA195 and Analogs Stabilized UBFL In Vitro

HeLa cells were transiently transfected with tetra ubiquitin-fused firefly luciferase (4UB-FL) plasmid. After 48 h, the transfected cells were treated with titrations of the indicated compounds for 4 h, and luciferase activity was measured. Data is expressed as a 4UB-FL fold change compared to untreated cells. As seen in FIG. 25, the RA compounds stabilize UBFL.

RA195 Induced Active Caspase-3 in HeLa Cells

Figure 26:
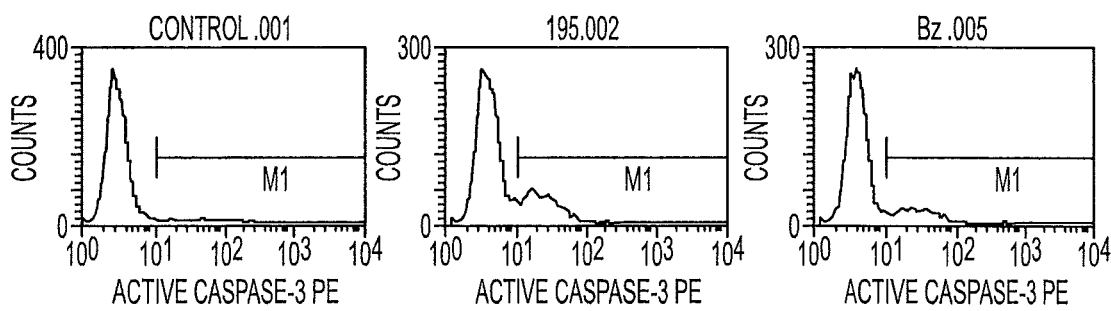
FIG. 26 shows a series of data graphs showing the effect of RA195 on the expression of active caspase-3 as determined by flow cytometry using a PE-labeled monoclonal antibody specific for the active form of caspase-3.

HeLa cells were treated with RA195 (1 μM) and Bz(1 μM) for the period of 8 h. Cells were stained for PE-conjugated Caspase-3 antibody and measured active caspase-3 by FACS. As seen in FIG. 26, cells treated with RA195 (middle panel) have induced active capase expression compared to those treated with Bortezomib (right panel) or control cells (left panel).

RA195 Induced Active Caspase-3 in Multiple Myeloma NCI-H929 Cells

Figure 27:
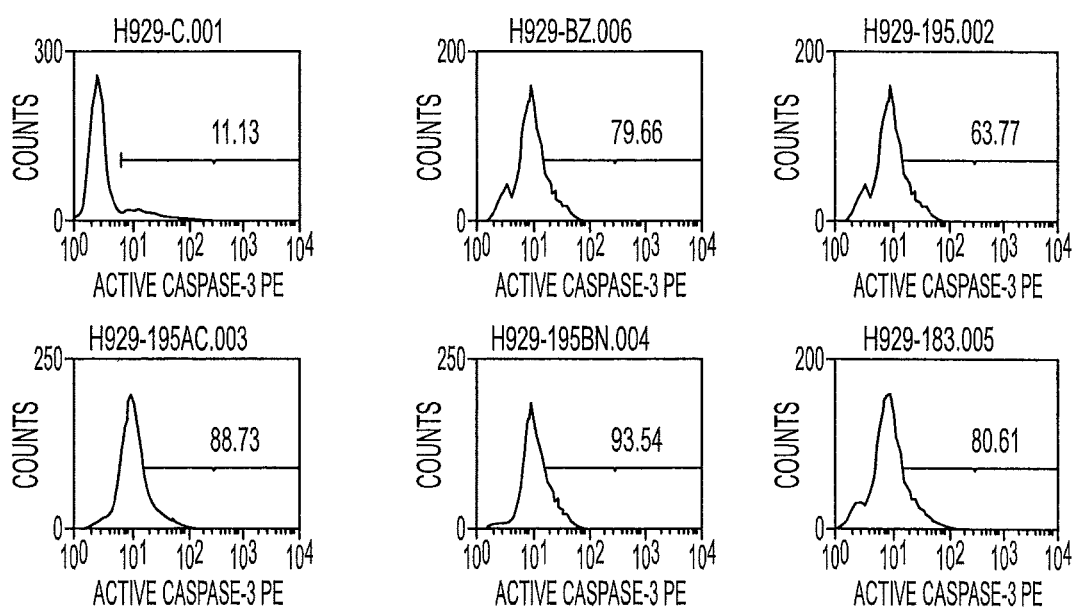
FIG. 27 shows a series of data graphs showing that treatment of NCIH929 cells with RA195, RA195AC, 195BN and RA183 caused an increase in caspase-3 expression as determined by flow cytometry using a PE-labeled monoclonal antibody specific for the active form of caspase-3.

NCI-H929 cells were treated with RA195 (0.5 μM) and Bz(0.5 μM) for the period of 8 h. Cells were stained for PE-conjugated Caspase-3 antibody and measured active caspase-3 by FACS. As seen in FIG. 27, treatment of NCI H929 cells with RA195, RA195AC, RA195BN and RA183 caused an increase in caspase-3 expression.

RA195 Induced Active Caspase-3 in Multiple Myeloma 0266 Cells

Figure 28:
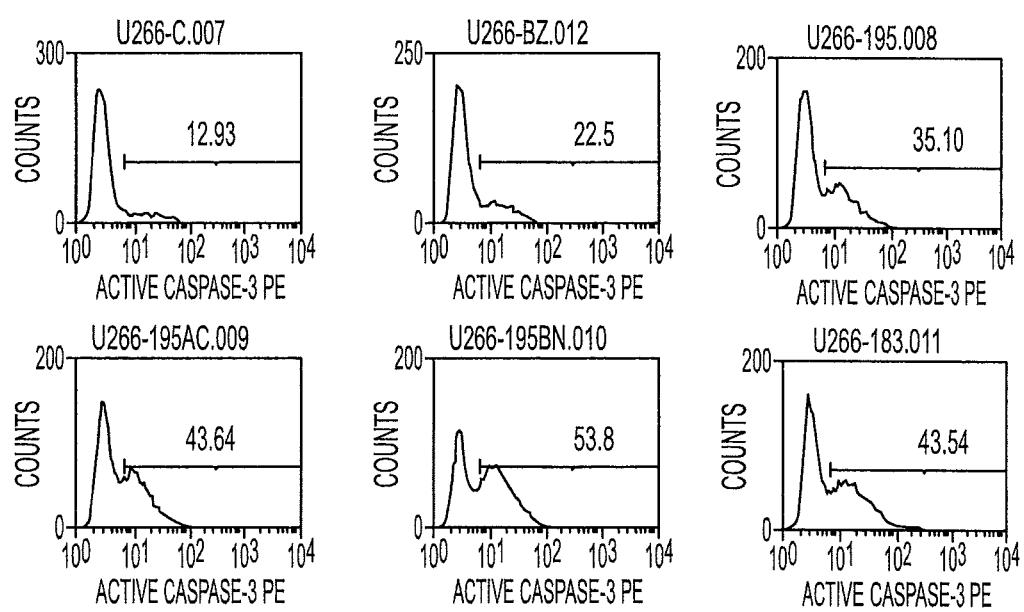
FIG. 28 shows a series of data graphs showing that treatment of U266 cells with RA195, RA195AC, 195BN and RA183 caused an increase in active caspase-3 expression as determined by flow cytometry using a PE-labeled monoclonal antibody specific for the active form of caspase-3.

U266 cells were treated with RA195 (0.5 μM) and Bz(0.5 μM) for the period of 8 h. Cells were stained for PE-conjugated Caspase-3 antibody and measured active caspase-3 by FACS. As seen in FIG. 28, treatment of U266 cells with RA195, RA195AC, 195BN and RA183 caused an increase in caspase-3 expression.

Figure 29:
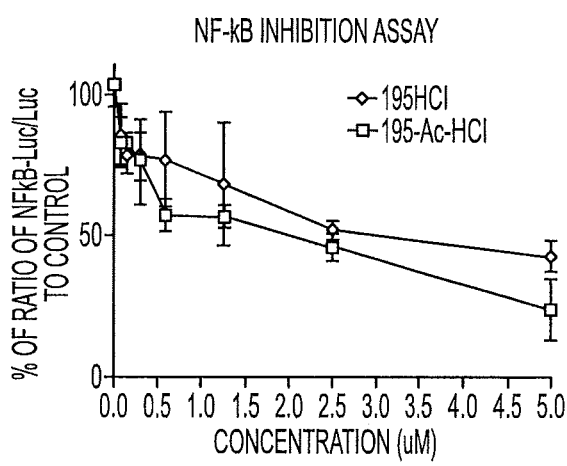
FIG. 29 shows a data graph showing that RA195 and its analog 195Ac inhibit TNFα-induced NFκB activation. HEK293 cells transiently transfected with either NFκB/FL (firefly luciferase reporter construct under control of an NFκB-driven promotor) or control CMV promotor-driven FL reporter construct were treated with compounds and TNFα (10 ng/ml) for 7 h. Upon the addition of luciferin, bioluminescence was measured in cell lysates using a luminometer. HEK293 cells showed dose dependent decrease in NF-κB associated promoter activity after RA195 and RA195Ac treatment.

RA195 and its Analog RA195Ac Inhibit TNFα-Induced NFκB Activation 293 cells transiently transfected with either NFκB/FL or control FL reporter genes were treated with compounds and TNFα (10 ng/ml) for 7 h. Upon the addition of luciferin, bioluminescence was measured in cell lysates using a luminometer. As seen in FIG. 29, RA195 and its analog RA195Ac inhibited TNFα-induced NFκB activation.

Figure 30:
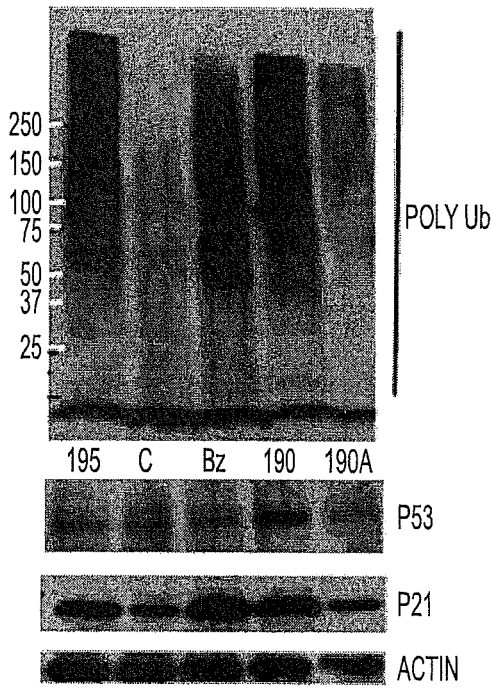
FIG. 30 shows an immunoblot showing that poly-ubiquitinated proteins (poly-UB) accumulated and p53 and p21 protein levels are increased in cells treated with RA190 and RA195.

RA195 Accumulated Poly UB Proteins and Elevated the Levels of p53 and p21 Proteins in HeLa Cells HeLa cells were treated with corresponding compounds (1 μM) for 12 h and the lysate was subjected to immunoblot and probed with anti-ubiquitin (UB), anti-p53, anti-p21 and anti-actin antibodies. As seen in FIG. 30, RA195 treatment caused the accumulation of poly-ubiqutinated (Poly UB) proteins and elevated the levels of p53 and p21 proteins in HeLa cells.

REFERENCES

1 Adams, J. (2004). The proteasome: a suitable antineoplastic target. Nat Rev Cancer 4, 349-360.
2 Al-Shami, A., Jhaver, K. G., Vogel, P., Wilkins, C., Humphries, J., Davis, J. J., Xu, N., Potter, D. G., Gerhardt, B., Mullinax, R., et al. (2010). Regulators of the proteasome pathway, Uch37 and Rpn13, play distinct roles in mouse development. PLoS ONE 5, e13654.
3 Anchoori, R. K., Khan, S. R., Sueblinvong, T., Felthauser, A., Iizuka, Y., Gavioli, R., Destro, F., Isaksson Vogel, R., Peng, S., Roden, R. B., and Bazzaro, M. (2011). Stressing the ubiquitin-proteasome system without 20S proteolytic inhibition selectively kills cervical cancer cells. PLoS ONE 6, e23888.
4 Arastu-Kapur, S., Anderl, J. L., Kraus, M., Parlati, F., Shenk, K. D., Lee, S. J., Muchamuel, T., Bennett, M. K., Driessen, C., Ball, A. J., et al. (2011). Nonproteasomal targets of the proteasome inhibitors bortezomib and carfilzomib: a link to clinical adverse events. Clin. Cancer Res. 17, 2734-2743.
5 Bazzaro, M., Anchoori, R. K., Mudiam, M. K., Issaenko, O., Kumar, S., Karanam, B., Lin, Z., Isaksson Vogel, R., Gavioli, R., Destro, F., et al. (2011). a,b-Unsaturated carbonyl system of chalcone-based derivatives is responsible for broad inhibition of proteasomal activity and preferential killing of human papilloma virus (HPV) positive cervical cancer cells. J. Med. Chem. 54, 449-456.
6 Bazzaro, M., Lee, M. K., Zoso, A., Stirling, W. L., Santillan, A., Shih le, M., and Roden, R. B. (2006). Ubiquitin-proteasome system stress sensitizes ovarian cancer to proteasome inhibitor-induced apoptosis. Cancer Res 66, 3754-3763.
7 Bedford, L., Lowe, J., Dick, L. R., Mayer, R. J., and Brownell, J. E. (2011). Ubiquitin-like protein conjugation and the ubiquitin-proteasome system as drug targets. Nat Rev Drug Discov 10, 29-46.
8 Best, S. R., Peng, S., Juang, C. M., Hung, C. F., Hannaman, D., Saunders, J. R., Wu, T. C., and Pai, S. I. (2009). Administration of HPV DNA vaccine via electroporation elicits the strongest CD8+ T cell immune responses compared to intramuscular injection and intradermal gene gun delivery. Vaccine 27, 5450-5459.
9 Chauhan, D., Catley, L., Li, G., Podar, K., Hideshima, T., Velankar, M., Mitsiades, C., Mitsiades, N., Yasui, H., Letai, A., et al. (2005). A novel orally active proteasome inhibitor induces apoptosis in multiple myeloma cells with mechanisms distinct from Bortezomib. Cancer Cell 8, 407-419.
10 Chen, S., Blank, J. L., Peters, T., Liu, X. J., Rappoli, D. M., Pickard, M. D., Menon, S., Yu, J., Driscoll, D. L., Lingaraj, T., et al. (2010a). Genome-wide siRNA screen for modulators of cell death induced by proteasome inhibitor bortezomib. Cancer Res 70, 4318-4326.
11 Chen, X., Lee, B. H., Finley, D., and Walters, K. J. (2010b). Structure of proteasome ubiquitin receptor hRpn13 and its activation by the scaffolding protein hRpn2. Mol Cell 38, 404-415.
12 Ciechanover, A. (1998). The ubiquitin-proteasome pathway: on protein death and cell life. Embo J 17, 7151-7160.
13 Delaglio, F., Grzesiek, S., Vuister, G. W., Zhu, G., Pfeifer, J., and Bax, A. (1995). NMRPipe: a multidimensional spectral processing system based on UNIX pipes. J Biomol NMR 6, 277-293.
14 Deveraux, Q., Ustrell, V., Pickart, C., and Rechsteiner, M. (1994). A 26 S protease subunit that binds ubiquitin conjugates. J. Biol. Chem. 269, 7059-7061.
15 Dominguez, C., Boelens, R., and Bonvin, A. M. (2003). HADDOCK: a protein-protein docking approach based on biochemical or biophysical information. J Am Chem Soc 125, 1731-1737.
16 Gandhi, T. K., Zhong, J., Mathivanan, S., Karthick, L., Chandrika, K. N., Mohan, S. S., Sharma, S., Pinkert, S., Nagaraju, S., Periaswamy, B., et al. (2006). Analysis of the human protein interactome and comparison with yeast, worm and fly interaction datasets. Nat. Genet. 38, 285-293.
17 Hamazaki, J., Iemura, S., Natsume, T., Yashiroda, H., Tanaka, K., and Murata, S. (2006). A novel proteasome interacting protein recruits the deubiquitinating enzyme UCH37 to 26S proteasomes. Embo J 25, 4524-4536.
18 Howie, H. L., Katzenellenbogen, R. A., and Galloway, D. A. (2009). Papillomavirus E6 proteins. Virology 384, 324-334.
19 Husnjak, K., Elsasser, S., Zhang, N., Chen, X., Randles, L., Shi, Y., Hofmann, K., Walters, K. J., Finley, D., and Dikic, I. (2008). Proteasome subunit Rpn13 is a novel ubiquitin receptor. Nature 453, 481-488.
20 Ito, T., Chiba, T., Ozawa, R., Yoshida, M., Hattori, M., and Sakaki, Y. (2001). A comprehensive two-hybrid analysis to explore the yeast protein interactome. Proc. Natl. Acad. Sci. USA 98, 4569-4574.
21 Koulich, E., Li, X., and DeMartino, G. N. (2008). Relative structural and functional roles of multiple deubiquitylating proteins associated with mammalian 26S proteasome. Mol. Biol. Cell 19, 1072-1082.
22 Kuhn, D. J., Berkova, Z., Jones, R. J., Woessner, R., Bjorklund, C. C., Ma, W., Davis, R. E., Lin, P., Wang, H., Madden, T. L., et al. (2012). Targeting the insulin-like growth factor-1 receptor to overcome bortezomib resistance in preclinical models of multiple myeloma. Blood 120, 3260-3270.
23 Lin, Z., Bazzaro, M., Wang, M. C., Chan, K. C., Peng, S., and Roden, R. B. (2009). Combination of Proteasome and HDAC Inhibitors for Uterine Cervical Cancer Treatment. Clin Cancer Res 15, 570-577.
24 Luker, G. D., Pica, C. M., Song, J., Luker, K. E., and Piwnica-Worms, D. (2003). Imaging 26S proteasome activity and inhibition in living mice. Nat Med 9, 969-973.
25 Maki, C. G., Huibregtse, J. M., and Howley, P. M. (1996). In vivo ubiquitination and proteasome-mediated degradation of p53(1). Cancer Res 56, 2649-2654.
26 Moody, C. A., and Laimins, L. A. (2010). Human papillomavirus oncoproteins: pathways to transformation. Nat Rev Cancer 10, 550-560.
27 Qiu, X. B., Ouyang, S. Y., Li, C. J., Miao, S., Wang, L., and Goldberg, A. L. (2006). hRpn13/ADRM1/GP110 is a novel proteasome subunit that binds the deubiquitinating enzyme, UCH37. EMBO J. 25, 5742-5753.
28 Ri, M., Iida, S., Nakashima, T., Miyazaki, H., Mori, F., Ito, A., Inagaki, A., Kusumoto, S., Ishida, T., Komatsu, H., et al. (2010). Bortezomib-resistant myeloma cell lines: a role for mutated PSMB5 in preventing the accumulation of unfolded proteins and fatal ER stress. Leukemia 24, 1506-1512.
29 Ruschak, A. M., Slassi, M., Kay, L. E., and Schimmer, A. D. (2011). Novel proteasome inhibitors to overcome bortezomib resistance. J Natl Cancer Inst 103, 1007-1017.
30 Sakata, E., Bohn, S., Mihalache, O., Kiss, P., Beck, F., Nagy, I., Nickell, S., Tanaka, K., Saeki, Y., Forster, F., et al. (2012). Localization of the proteasomal ubiquitin receptors Rpn10 and Rpn13 by electron cryomicroscopy. Proc Natl Acad Sci USA 109, 1479-1484.
31 Schreiner, P., Chen, X., Husnjak, K., Randles, L., Zhang, N., Elsasser, S., Finley, D., Dikic, I., Walters, K. J., and Groll, M. (2008). Ubiquitin docking at the proteasome through a novel pleckstrin-homology domain interaction. Nature 453, 548-552.
32 Schwartz, A. L., and Ciechanover, A. (2009). Targeting proteins for destruction by the ubiquitin system: implications for human pathobiology. Annu Rev Pharmacol Toxicol 49, 73-96.
33 Spisek, R., and Dhodapkar, M. V. (2007). Towards a better way to die with chemotherapy: role of heat shock protein exposure on dying tumor cells. Cell Cycle 6, 1962-1965.
34 Trimble, C., Lin, C. T., Hung, C. F., Pai, S., Juang, J., He, L., Gillison, M., Pardoll, D., Wu, L., and Wu, T. C. (2003). Comparison of the CD8+ T cell responses and antitumor effects generated by DNA vaccine administered through gene gun, biojector, and syringe. Vaccine 21, 4036-4042.
35 Vousden, K. H., and Lu, X. (2002). Live or let die: the cell's response to p53. Nat Rev Cancer 2, 594-604.
36 Welters, M. J., Kenter, G. G., Piersma, S. J., Vloon, A. P., Lowik, M. J., Berends-van der Meer, D. M., Drijfhout, J.

W., Valentijn, A. R., Wafelman, A. R., Oostendorp, J., et al. (2008). Induction of tumor-specific CD4+ and CD8+ T-cell immunity in cervical cancer patients by a human papillomavirus type 16 E6 and E7 long peptides vaccine. Clin Cancer Res 14, 178-187.

37 Yao, T., Song, L., Xu, W., DeMartino, G. N., Florens, L., Swanson, S. K., Washburn, M. P., Conaway, R. C., Conaway, J. W., and Cohen, R. E. (2006) Proteosome Recruitment and activation of the Uch37 debiquitinating enzyme by Adrm1. Nat. Cell Biol. 8, 994-1002

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method of inhibiting proteasomes in a mammal by administering to the mammal an effective amount of a compound of formula I,

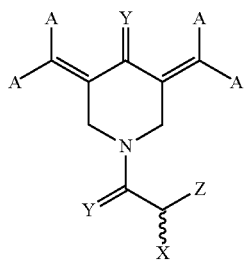

(I)

wherein each pair of As is one of:
(i) phenyl, optionally substituted with 1-5 substituents selected from the group consisting of R1, OR1, NR1R2, S(O)$_q$A1, SO$_2$NR1R2, NR1SO$_2$R2, C(O)R1, C(O)OR1, C(O)NR1R2, NR1C(O)R2, NR1C(O)OR2, CF$_3$, and OCF$_3$;
(ii) naphthyl, optionally substituted with 1-5 substituents selected from the consisting of R1, OR1, NR1R2, S(O)$_q$A1, SO$_2$NR1R2, NR1SO$_2$R2, C(O)R1, C(O)OR1, C(O)NR1R2, NR1C(O)R2, NR1C(O)OR2, CF$_3$, and OCF$_3$;
(iii) a 5 or 6 membered monocyclic heteroaryl group, having 1-3 heteroatoms selected from the group consisting of O, N, and S, optionally substituted with 1-3 substituents selected from the group consisting of R1, OR1, NR1R2, S(O)$_q$A1, SO$_2$NR1R2, NR1SO$_2$R2, C(O)R1, C(O)OR1, C(O)NR1R2, NR1C(O)R2, NR1C(O)OR2, CF$_3$, and OCF$_3$; and
(iv) an 8 to 10 membered bicyclic heteroaaryl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of R1, OR1, NR1R2, S(O)$_q$A1, SO$_2$NR1R2, NR1SO$_2$R2, C(O)R1, C(O)OR1, C(O)NR1R2, NR1C(O)R2, NR1C(O)OR2, CF$_3$, and OCF$_3$;
wherein X is OR1 or NP, wherein P is selected from the group consisting of R1, C(O)R1, C(O)OR1, C(O)NR1R2, S—N(R1)COOR1, and S—N(R1),
wherein Y is selected from the group consisting of O, S, NR1 and CR1R2,
wherein R1 and R2 are selected from the group consisting of hydrogen, nitro; hydroxyl; carboxy; amino; halogen; cyano; and C$_1$-C$_{14}$ linear or branched alkyl groups, that are optionally substituted with 1-3 substituents selected from the group consisting of C$_1$-C$_{14}$ linear or branched alkyl, up to perhalo substituted C$_1$-C$_{14}$ linear or branched alkyl, C$_1$-C$_{14}$ alkoxy, hydrogen, nitro, hydroxyl, carboxy, amino, C$_1$-C$_{14}$ alkylamino, C$_1$-C$_{14}$ dialkylamino, halogen, and cyano; and
wherein Z is selected from the group consisting of hydrogen; C$_1$ to C$_{14}$ linear, branched, or cyclic alkyls; phenyl; benzyl; 1-5 substituted benzyl; C$_1$ to C$_3$ alkyl-phenyl, wherein the alkyl moiety is optionally substituted with halogen up to perhalo; up to perhalo substituted C$_1$ to C$_{14}$ linear or branched alkyls; and —(CH$_2$)$_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N and S, wherein said alkyl moiety is optionally substituted with halogen up to perhalo; and wherein the variable q is an integer ranging from 0 to 4; and
wherein inhibiting the proteasomes comprises inhibiting a ubiquitin proteasome system.

2. The method of claim 1, wherein the mammal is a human.

3. The method of claim 1, wherein the method treats a condition or a disease in the mammal.

4. The method of claim 3, wherein the mammal is a human.

5. The method of claim 3, wherein the condition or disease is a type of cancer.

6. The method of claim 5, wherein the type of cancer is selected from the group consisting of breast cancer, cervical cancer, ovarian cancer, multiple myeloma, breast cancer and pancreatic cancer.

7. The method of claim 5, wherein the type of cancer is associated with Human Papilloma Virus (HPV).

8. The method of claim 1, wherein the compound is administered in combination with at least one other therapeutic agent.

9. The method of claim 8, wherein the at least one other therapeutic agent is a proteasome inhibitor.

10. The method of claim 8, wherein the at least one other therapeutic agent is bortezomib.

11. The method of claim 1, wherein the compound binds to RPN13.

12. The method of claim 1, wherein the compound is orally administered.

13. The method of claim 1, wherein the compound is intraperitoneally administered.

14. The method compound of claim 1, wherein the compound is topically applied.

15. The method of claim 1, wherein the compound has the structure:

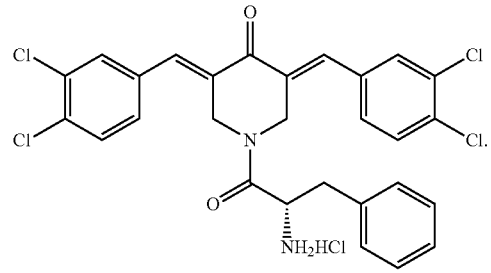

16. A method of inhibiting proteasomes in a mammal by administering to the mammal an effective amount of a compound having the structure:
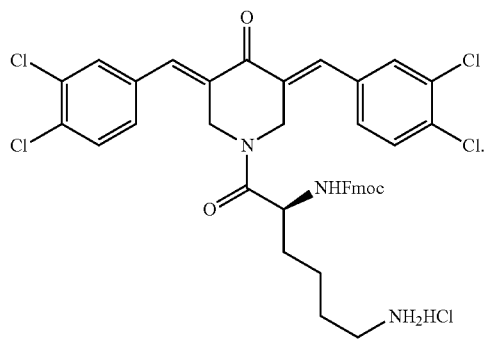
17. The method of claim 1, wherein the compound has the structure:
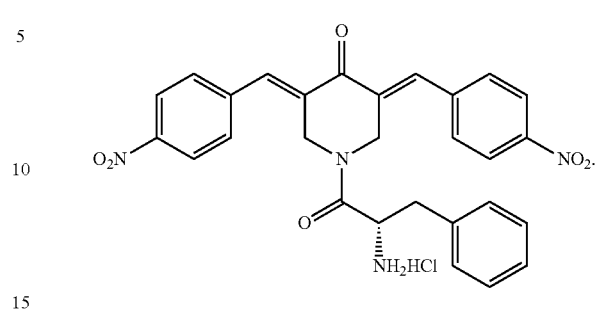
* * * * *